United States Patent
Guerry et al.

(10) Patent No.: US 10,500,262 B2
(45) Date of Patent: *Dec. 10, 2019

(54) **SYNTHETIC ANTIGEN CONSTRUCTS AGAINST *CAMPYLOBACTER JEJUNI***

(71) Applicant: United States of America as Represented by the Secretary of the Navy, Washington, DC (US)

(72) Inventors: Patricia Guerry, Silver Spring, MD (US); Mario Artur Monteiro, Guelph (CA); Yuening Jiao, Etobicoke (CA)

(73) Assignee: The United States of America as Represented by the Secretary of the Navy, Arlington, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/891,426

(22) Filed: Feb. 8, 2018

(65) Prior Publication Data

US 2018/0177857 A1    Jun. 28, 2018

Related U.S. Application Data

(63) Continuation of application No. 14/933,793, filed on Nov. 5, 2015, now Pat. No. 9,925,254.

(60) Provisional application No. 62/075,399, filed on Nov. 5, 2014, provisional application No. 62/127,935, filed on Mar. 4, 2015.

(51) Int. Cl.
| | |
|---|---|
| *A61K 39/02* | (2006.01) |
| *C07H 11/04* | (2006.01) |
| *C07H 13/00* | (2006.01) |
| *A61K 39/00* | (2006.01) |

(52) U.S. Cl.
CPC ............ *A61K 39/105* (2013.01); *C07H 11/04* (2013.01); *C07H 13/00* (2013.01); *A61K 2039/6037* (2013.01); *Y02A 50/47* (2018.01)

(58) Field of Classification Search
None
See application file for complete search history.

(56) References Cited

U.S. PATENT DOCUMENTS

| | | |
|---|---|---|
| 2005/0106159 A1 | 5/2005 | Thompson |
| 2015/0258201 A1 | 9/2015 | Guerry et al. |

FOREIGN PATENT DOCUMENTS

| | | |
|---|---|---|
| WO | 2005/020964 A1 | 3/2005 |
| WO | 2009/017666 A1 | 2/2009 |

OTHER PUBLICATIONS

Supplementary European Search Report in EP15856653 dated Apr. 26, 2018.
Ashmus, R. et al. Organic Letters, vol. 16, No. 9, Apr. 16, 2014, pp. 2518-2521.
Poly, F. et al. J. Clinical Microbiology, vol. 49, No. 5, Mar. 16, 2011, pp. 1750-1757.
Redkyna, O. "A Vaccine against Campylobacter jejuni Serotype HS:5", Thesis presented to the University of Guelph (Canada) for Master of Science in Chemistry, Dec. 2013.
Pequegnat, B. et al., Journal of Bacteriology, vol. 199, Issue 14, Jul. 1, 2017, e00027-17.
Pequegnat, B., "Polysaccharide Vaccines for Enteric Pathogens: The Next Generation Multivalent Diarrhea Vaccine" Thesis presented to the University of Guelph (Canada) for degree of Philosophical Doctorate in Chemistry, May 2016.
International Search Report in PCT/US2016/060361 dated Jan. 9, 2017.
Written Opinion of the International Searching Authority in PCT/US2016/060361 dated Jan. 9, 2017.
Riazi et al., PLoS One, vol. 8, No. 12, pp. e83928. Dec. 31, 2013.
Tsubokure et al., Clin. Exp. Immunol. vol. 108, pp. 451-455, Jun. 1, 1997.

*Primary Examiner* — Dale R Miller
(74) *Attorney, Agent, or Firm* — Diane P. Tso; Ning Yang; Albert M. Churilla

(57) ABSTRACT

The invention relates to immunogenic synthetic constructs capable of inducing an immune response against *Campylobacter jejuni* (*C. jejuni*) in a subject comprising one or more monosaccharides comprising one or more MeOPN moieties. Specifically, the invention relates to immunogenic synthetic constructs capable of inducing an immune response against *Campylobacter jejuni* (*C. jejuni*) in a subject comprising one or more MeOPN→6 Gal monosaccharides. The invention also relates to compositions comprising the immunogenic synthetic constructs and methods of inducing an immune response against *C. jejuni* in a subject comprising administering the immunogenic synthetic constructs, and/or compositions comprising the immunogenic synthetic construct, to the subject.

36 Claims, 27 Drawing Sheets

Specification includes a Sequence Listing.

Figure 1

Serotype

HS1

→4)-α-D-Gal*p*-(1→2)-Gro-(1→P→
　　　　3　2
　　　／　＼
　　　2　　2
　　Fru*f*　Fru*f*
　　　3　　3
　　　｜　　｜
　MeOPN*　MeOPN*

---

HS4

MeOPN*
　　　　　　｜
　　　　　　7
→3)-α-D-6d-*ido*-Hep*p*-(1→4)-D-Glc*p*NAc-(1→
　　　　　　2
　　　　　　｜
　　　　　MeOPN*

---

HS3

→3)-β-D-6d-*ido*-Hep*p*-(1→4)-α-D-Gal*p*-(1→3)-β-D-*ido*-Hep*p*-(1→4)-α-D-Gal*p*-(1→
　　　　　　2　　　　　　　　　　　　　　　　　　　　2
　　　　　　｜　　　　　　　　　　　　　　　　　　　　｜
　　　　　MeOPN*　　　　　　　　　　　　　　　　　MeOPN*

---

HS23/36

MeOPN*
　　　　｜
　　　　6
→3)-α-D-Gal*p*-(1→2)-3-*O*-Me-D-6d-*altro*-Hep*p*-(1→3)-D-Glc*p*NAc-(1→3)-α-D-Gal*p*-(1→
　　　　　　　　　　　　　　　　　　　　　　　　　　　　　　　　　　　　　　　　　2
　　　　　　　　　　　　　　　　　　　　　　　　　　　　　　　　　　　　　　　　　｜
　　　　　　　　　　　　　　　　　　　　　　　　　　　　　　　　　　　　　　　MeOPN*

Scheme 1

Scheme 2

3 R¹= H, R²= OMP, R³= All, R⁴= Tr
7 R¹, R²= H, OTCA, R³= All, R⁴= Tr
8 R¹= O(CH₂)₅NPhth, R²= H, R³= All, R⁴= Tr
9 R¹= O(CH₂)₅NPhth, R²= H, R³= All, R⁴= H 10 R¹= (CH₂)₅NPhth, R²= All
11 R¹= (CH₂)₅NPhth, R²= H
12 R¹= (CH₂)₅NH₂, R²= H Scheme 2a (A)

(B)

Scheme 4

(A)

(B)

(A)

(B)

SEQUENCE LISTING

<160> NUMBER OF SEQ ID NOS: 20

<210> SEQ ID NO 1
<211> LENGTH: 41
<212> TYPE: DNA
<213> ORGANISM: Artificial Sequence
<220> FEATURE:
<223> OTHER INFORMATION: C. Jejuni

<400> SEQUENCE: 1
ggaattcgat gattatttta tagatattgg tgtgcctgag g                41

<210> SEQ ID NO 2
<211> LENGTH: 46
<212> TYPE: DNA
<213> ORGANISM: Artificial Sequence
<220> FEATURE:
<223> OTHER INFORMATION: C. jejuni

<400> SEQUENCE: 2
ccctcgaggg gatattacta tcgactatat cgtaactatt acaacc           46

<210> SEQ ID NO 3
<211> LENGTH: 24
<212> TYPE: DNA
<213> ORGANISM: Artificial Sequence
<220> FEATURE:
<223> OTHER INFORMATION: C. jejuni

<400> SEQUENCE: 3

```
ccagctgaac ttgcttggga gatg                                            24

<210> SEQ ID NO 4
<211> LENGTH: 38
<212> TYPE: DNA
<213> ORGANISM: Artificial Sequence
<220> FEATURE:
<223> OTHER INFORMATION: C. jejuni

<400> SEQUENCE: 4
gggatattac tatcgactat atcgtaacta ttacaacc                             38

<210> SEQ ID NO 5
<211> LENGTH: 30
<212> TYPE: DNA
<213> ORGANISM: Artificial Sequence
<220> FEATURE:
<223> OTHER INFORMATION: C. jejuni

<400> SEQUENCE: 5
gtgtgatgtg gtggttacgt tgaattcggg                                      30

<210> SEQ ID NO 6
<211> LENGTH: 39
<212> TYPE: DNA
<213> ORGANISM: Artificial Sequence
<220> FEATURE:
<223> OTHER INFORMATION: C. jejuni

<400> SEQUENCE: 6
ctcaaatcta tagtaagtgg catgattaac atgccaagc                            39

<210> SEQ ID NO 7
<211> LENGTH: 26
<212> TYPE: DNA
<213> ORGANISM: Artificial Sequence
<220> FEATURE:
<223> OTHER INFORMATION: C. jejuni

<400> SEQUENCE: 7
catccttatc cttcattact tgatcc                                          26

<210> SEQ ID NO 8
<211> LENGTH: 27
<212> TYPE: DNA
<213> ORGANISM: Artificial Sequence
<220> FEATURE:
<223> OTHER INFORMATION: C. jejuni

<400> SEQUENCE: 8
cgtggaacat gtttatttat catatgc                                         27

<210> SEQ ID NO 9
<211> LENGTH: 28
<212> TYPE: DNA
<213> ORGANISM: Artificial Sequence
<220> FEATURE:
<223> OTHER INFORMATION: C. jejuni

<400> SEQUENCE: 9
catgaaaatc ctgagcttgg ttttgatg                                        28

<210> SEQ ID NO 10
<211> LENGTH: 29
<212> TYPE: DNA
<213> ORGANISM: Artificial Sequence
```

```
<220> FEATURE:
<223> OTHER INFORMATION: C. jejuni

<400> SEQUENCE: 10
gtattttaaa actagcttcg cataataac                                      29

<210> SEQ ID NO 11
<211> LENGTH: 42
<212> TYPE: DNA
<213> ORGANISM: Artificial Sequence
<220> FEATURE:
<223> OTHER INFORMATION: C. jejuni

<400> SEQUENCE: 11
gcgcccatgg gttaacggag cacttccatg accacctctt cc                       42

<210> SEQ ID NO 12
<211> LENGTH: 50
<212> TYPE: DNA
<213> ORGANISM: Artificial Sequence
<220> FEATURE:
<223> OTHER INFORMATION: C. jejuni

<400> SEQUENCE: 12
gcgcccatgg tctagaagat ctcctattta tgctgcttct ttgcttctgg               50

<210> SEQ ID NO 13
<211> LENGTH: 42
<212> TYPE: DNA
<213> ORGANISM: Artificial Sequence
<220> FEATURE:
<223> OTHER INFORMATION: C. jejuni

<400> SEQUENCE: 13
cgggatccaa aggagaaacc ctatgtataa cccaaactca gc                       42

<210> SEQ ID NO 14
<211> LENGTH: 55
<212> TYPE: DNA
<213> ORGANISM: Artificial Sequence
<220> FEATURE:
<223> OTHER INFORMATION: C. jejuni

<400> SEQUENCE: 14
ggaattcgta aaatcccctt gtttcatatt gattcctttc tctaatttta aacac         55

<210> SEQ ID NO 15
<211> LENGTH: 57
<212> TYPE: DNA
<213> ORGANISM: Artificial Sequence
<220> FEATURE:
<223> OTHER INFORMATION: C. jejuni

<400> SEQUENCE: 15
gctatgattg agtttacaaa caatggagga ggatatatag cattatttaa aaaactc       57

<210> SEQ ID NO 16
<211> LENGTH: 57
<212> TYPE: DNA
<213> ORGANISM: Artificial Sequence
<220> FEATURE:
<223> OTHER INFORMATION: C. jejuni

<400> SEQUENCE: 16
gagtttttta aataatgcta tatatcctcc tccattgttt gtaaactcaa tcatagc       57
```

```
<210> SEQ ID NO 17
<211> LENGTH: 44
<212> TYPE: DNA
<213> ORGANISM: Artificial Sequence
<220> FEATURE:
<223> OTHER INFORMATION: C. jejuni

<400> SEQUENCE: 17
ggaattccta tattataaga taataacaca attcgcctcc tatg                    44

<210> SEQ ID NO 18
<211> LENGTH: 40
<212> TYPE: DNA
<213> ORGANISM: Artificial Sequence
<220> FEATURE:
<223> OTHER INFORMATION: C. jejuni

<400> SEQUENCE: 18
cgggatccag gagaaaccct atgtataacc caaactcagc                         40

<210> SEQ ID NO 19
<211> LENGTH: 57
<212> TYPE: DNA
<213> ORGANISM: Artificial Sequence
<220> FEATURE:
<223> OTHER INFORMATION: C. jejuni

<400> SEQUENCE: 19
gctatgattg agtttacaaa caatggagga ggatatatag cattatttaa aaaactc      57

<210> SEQ ID NO 20
<211> LENGTH: 55
<212> TYPE: DNA
<213> ORGANISM: Artificial Sequence
<220> FEATURE:
<223> OTHER INFORMATION: C. jejuni

<400> SEQUENCE: 20
agttttttaa ataatgctat atacctcctc ctttgtttgt aaactcaatc atagc        55
```

SYNTHETIC ANTIGEN CONSTRUCTS AGAINST *CAMPYLOBACTER JEJUNI*

CROSS REFERENCE TO RELATED APPLICATIONS

The present application is a continuation application which claims the benefit of U.S. Non-Provisional patent application Ser. No. 14/933,793 filed Nov. 5, 2015, which claims the benefit of U.S. Provisional Patent Application No. 62/075,399 filed Nov. 5, 2014, and the benefit of U.S. Provisional Patent Application No. 62/127,935 filed Mar. 4, 2015, the disclosures of which are incorporated by reference herein.

SEQUENCE LISTING

The instant application contains a Sequence Listing which has been submitted in ASCII format via EFS-Web and is hereby incorporated by reference in its entirety. Said ASCII copy, created on Jan. 11, 2016 is named "103281nonprov_ST25.txt" and is 3.99 kilobytes in size.

FIELD OF THE INVENTION

The inventive subject matter of the instant invention relates to immunogenic synthetic constructs capable of inducing an immune response against *Campylobacter jejuni* (*C. jejuni*) in a subject. The inventive subject matter of the instant invention also relates to compositions comprising the immunogenic synthetic constructs as well as methods of inducing an immune response against *C. jejuni* in a subject.

BACKGROUND OF THE INVENTION

Diarrheal diseases are a major cause of morbidity and mortality in the developing world. Among the most frequent bacterial causes of diarrhea are enterotoxigenic. *Escherichia coli* (ETEC), *Shigella* species, and *C. jejuni*. Indeed, *C. jejuni* is estimated to cause 2.5 million cases of gastroenteritis annually in the United States and greater than 400 million cases worldwide. In developing countries, *C. jejuni* gastroenteritis is primarily a pediatric disease. The symptoms of *C. jejuni* gastroenteritis include diarrhea, abdominal pain, fever and sometimes vomiting. Stools usually contain mucus, fecal leukocytes and blood, although watery diarrhea is also observed. The disease is zoonotic, and wild and domesticated birds represent a major reservoir. *C. jejuni* is a major foodborne infection, most often being associated with contaminated poultry, but major outbreaks have been associated with water or raw milk contamination.

In addition to causing gastroenteritis, *C. jejuni* can also cause several undesirable post-infectious conditions, including inflammatory bowel syndrome, and a spondyloarthropathy known as Reiter's Syndrome. Moreover, recent studies have indicated an association between *C. jejuni* infections and malnutrition and growth stunting in young children in resource-limited settings.

Another possible debilitating complication of *C. jejuni* infection is the development of Guillain-Barré Syndrome (GBS), a post-infectious polyneuropathy that can result in paralysis (Allos, B. M., J. Infect. Dis 176 (Suppl 2):S125-128 (1997).) *C. jejuni* is one of a limited number of bacteria that can endogenously synthesize sialic acid, a nine carbon sugar that is found in mammalian cells. The association between *C. jejuni* and GBS is reportedly due to molecular mimicry between the sialic acid containing-outer core of the lipooligosaccharide (LOS) present in *C. jejuni* and human gangliosides (Moran, et al., J. Endotox. Res. 3: 521 (1996).) It is believed that antibodies generated by a human subject against the LOS cores of *C. jejuni* may cause an undesirable autoimmune response to neural tissue in the subject. Indeed, studies suggest that LOS synthesis in *Campylobacter* is controlled by a number of genes, including genes encoding enzymes involved in the biosynthesis of sialic acid. The sialic acid is then incorporated into LOS. This is consistent with the observed molecular mimicry of LOS and human gangliosides in GBS. (Aspinall, et al., Eur. J. Biochem., 213: 1029 (1993); Aspinall, et al., Infect. Immun. 62: 2122-2125 (1994); Aspinall, et al., Biochem 33: 241 (1994); Salloway et al., Infect. Immun., 64: 2945 (1996).)

*C. jejuni* is a Gram-negative bacterium, having surface capsular polysaccharides (CPSs) that are involved in colonization and invasion and against which serum antibodies are generated. Recent analysis of the *Campylobacter* genome sequence has resulted in the identification of a complete set of capsule transport genes similar to those seen in type II/III capsule loci in the Enterobactericeae (Parkhill et al., Nature, 403: 665 (2000); Karlyshev et al., Mol. Microbiol., 35: 529 (2000).) Subsequent genetic studies in which site-specific mutations were made in several capsule transport genes indicate that the capsule is the major serodeterminant of the Penner serotyping scheme (Karlyshev et al., Mol. Microbiol., 35: 529 (2000).) The Penner scheme is one of two major serotyping schemes of *campylobacters* and was originally thought to be based on lipopolysaccharide O side chains (Moran and Penner, J. Appl. Microbiol., 86:361 (1999).) It is now believed that the structures previously described as O side chains are, in fact, polysaccharide capsules. Interestingly, although *C. jejuni* capsular moieties are important in serodetermination, and despite over 47 Penner serotypes of *C. jejuni* having been identified, it is believed that most *Campylobacter* diarrheal disease is caused by only a limited number of these serotypes. Therefore, only selected strains of *C. jejuni*, predicated on epidemiological studies, may provide suitable candidate strains for development of potential vaccine compositions.

Several immunogenic CPS-CRM$_{197}$ conjugates associated with prevalent *C. jejuni* serotypes have been created. (Monteiro et al., (2009) Infect. Immun. 77, 1128-1136; Bertolo, L, et al. (2012) Carbohy Res 366:45-49.) An immunogenic *C. jejuni* CPS conjugate vaccine capable of protecting non-human primates against *C. jejuni* diarrhea has been developed. (Monteiro et al., (2009) Infect. Immun. 77, 1128-1136, U.S. Pat. No. 9,084,809.) U.S. Pat. No. 9,084,809 describes, inter alia, an anti-*C. jejuni* immunogenic composition composed of a capsule polysaccharide polymer of *C. jejuni* strain 81-176 (also referred to herein as serotype HS23/36) that is capable of inducing an immune response in BALB/c mice. This reference teaches that the HS23/36 capsule polysaccharide comprises trisaccharides of galactose, 3-O-methyl-6-deoxy-altro-heptose and N-acetyl glucosamine; specifically, the immunogenic polysaccharide polymer comprises a repeating trisaccharide structure having the formula [→3)-α-D-Gal-(1→2)-6d-3-O-Me-α-D-altro-Hep-(1→3)-β-D-GlcNAc-(1→] containing an O-methyl-phosphoramidate at the O-2 position of Gal. Notwithstanding the promise of prototype vaccines, and despite the importance of this organism to human disease, there are yet no licensed, commercially available vaccines against *C. jejuni*. Thus, there currently remains a need for improved immunogenic compositions and methods for preventing or ameliorating diseases associated with *C. jejuni* infection.

BRIEF SUMMARY OF THE INVENTION

In a first aspect, the present invention relates to an immunogenic synthetic construct capable of inducing an immune response against *Campylobacter jejuni* (*C. jejuni*) in a subject, wherein said immunogenic synthetic construct comprises one or more monosaccharides comprising one or more MeOPN moieties. In a particular embodiment, the immunogenic synthetic constructs comprise one or more MeOPN→6 Gal monosaccharides.

In yet another aspect, the invention relates to compositions comprising an immunogenic synthetic construct capable of inducing an immune response against *C. jejuni* in a subject, wherein said immunogenic synthetic construct comprises one or more monosaccharides comprising one or more MeOPN moieties. In a particular embodiment, the immunogenic synthetic construct comprises one or more MeOPN→6 Gal monosaccharides.

In a further aspect, the invention relates to methods of inducing an immune response against *C. jejuni* in a subject comprising administering to the subject an effective amount of an immunogenic synthetic construct, wherein said immunogenic synthetic construct comprises one or more monosaccharides comprising one or more MeOPN moieties. In a particular embodiment, the immunogenic synthetic construct comprises one or more MeOPN→6 Gal monosaccharides. In a particular embodiment, the methods may further comprise administering one or more boosting doses of the immunogenic synthetic construct. In particular embodiments, the effective amount is an amount from about 0.1 µg to about 10 mg of immunogenic synthetic construct.

In a further aspect, the invention relates to methods of inducing an immune response against *C. jejuni* in a subject comprising administering to the subject an effective amount of a composition comprising an immunogenic synthetic construct, wherein the immunogenic synthetic construct comprises one or more monosaccharides comprising one or more MeOPN moieties. In a particular embodiment, the immunogenic synthetic construct comprises one or more MeOPN→6 Gal monosaccharides. In a particular embodiment, the methods may further comprise administering one or more boosting doses of the immunogenic synthetic construct. In particular embodiments, the effective amount is an amount from about 0.1 µg to about 10 mg of immunogenic synthetic construct.

In various additional aspects, the invention relates to an immunogenic synthetic construct for use in inducing an immune response against *C. jejuni* in a subject, wherein said immunogenic synthetic construct comprises one or more monosaccharides comprising one or more MeOPN moieties. In a particular embodiment, the immunogenic synthetic construct comprises one or more MeOPN→6 Gal monosaccharides. In another aspect, the invention relates to use of an immunogenic synthetic construct for inducing an immune response against *C. jejuni* in a subject wherein said immunogenic synthetic construct comprises one or more monosaccharides comprising one or more MeOPN moieties. In a particular embodiment, the immunogenic synthetic construct comprises one or more MeOPN→6 Gal monosaccharides. In another aspect, the invention relates to use of an immunogenic synthetic construct in the manufacture of a medicament for inducing an immune response against *C. jejuni* in a subject, wherein said immunogenic synthetic construct comprises one or more monosaccharides comprising one or more MeOPN moieties. In a particular embodiment, the immunogenic synthetic construct comprises one or more MeOPN→6 Gal monosaccharides.

In an additional aspect, the invention relates to a composition comprising an immunogenic synthetic construct for use in inducing an immune response against *C. jejuni* in a subject, wherein the immunogenic synthetic construct comprises one or more monosaccharides comprising one or more MeOPN moieties. In a particular embodiment, the immunogenic synthetic construct comprises one or more MeOPN→6 Gal monosaccharides. In another aspect, the invention relates to use of a composition comprising an immunogenic synthetic construct for inducing an immune response against *C. jejuni* in a subject, wherein the immunogenic synthetic construct comprises one or more monosaccharides comprising one or more MeOPN moieties. In a particular embodiment, the immunogenic synthetic construct comprises one or more MeOPN→6 Gal monosaccharides. In another aspect, the invention relates to use of a composition comprising an immunogenic synthetic construct in the manufacture of a medicament for inducing an immune response against *C. jejuni* in a subject, wherein the immunogenic synthetic construct comprises one or more monosaccharides comprising one or more MeOPN moieties. In a particular embodiment, the immunogenic synthetic construct comprises one or more MeOPN→6 Gal monosaccharides.

In an additional aspect, the invention relates to a pharmaceutical composition comprising an immunogenic synthetic construct for use in inducing an immune response against *C. jejuni* in a subject, wherein the immunogenic synthetic construct comprises one or more monosaccharides comprising one or more MeOPN moieties. In a particular embodiment, the immunogenic synthetic construct comprises one or more MeOPN→6 Gal monosaccharides. In another aspect, the invention relates to use of a pharmaceutical composition comprising an immunogenic synthetic construct for inducing an immune response against *C. jejuni* in a subject, wherein the immunogenic synthetic construct comprises one or more monosaccharides comprising one or more MeOPN moieties. In a particular embodiment, the immunogenic synthetic construct comprises one or more MeOPN→6 Gal monosaccharides. In another aspect, the invention relates to use of a pharmaceutical composition comprising an immunogenic synthetic construct in the manufacture of a medicament for inducing an immune response against *C. jejuni* in a subject, wherein the immunogenic synthetic construct comprises one or more monosaccharides comprising one or more MeOPN moieties. In a particular embodiment, the immunogenic synthetic construct comprises one or more MeOPN→6 Gal monosaccharides.

In an additional aspect, the present invention is directed to methods of synthesizing the immunogenic synthetic constructs of the instant invention.

In various embodiments of the aforementioned aspects, the immunogenic synthetic construct may be conjugated to a carrier compound, e.g., a carrier protein. In a particular embodiment, the carrier protein contains at least one T-cell epitope. In a particular embodiment, the carrier protein is $CRM_{197}$.

In additional embodiments of the aforementioned aspects, the composition is a pharmaceutical composition. In a particular embodiment, the pharmaceutical composition is a vaccine formulation.

In particular embodiments, the pharmaceutical compositions and the vaccine formulations may comprise one or more adjuvants. In particular embodiments, the adjuvant is selected from the group consisting of toll-like receptor ligands, aluminum phosphate, aluminum hydroxide, monophosphoryl lipid A, liposomes, and derivatives and combinations thereof. In further embodiments, the pharmaceutical compositions and vaccine formulations comprise one or more additional immunoregulatory agents. In a particular embodiment, the immunoregulatory agent is a substance selected from the group consisting of antigens of one or more strains of C. jejuni, antigens of ETEC, Shigella lipopolysaccharide structures, and unconjugated carrier proteins.

In particular embodiments, the methods of inducing an immune response against C. jejuni in a subject comprise administering the construct conjugated to a protein carrier. In a particular embodiment, the protein carrier is $CRM_{197}$. In another particular embodiment, the method further comprises administering the construct or conjugate with one or more adjuvants. In a particular embodiment, the adjuvant is selected from the group consisting of toll-like receptor ligands, aluminum phosphate, aluminum hydroxide, monophosphoryl lipid A, liposomes, and derivatives and combinations thereof. In particular embodiments of the aforementioned aspects, the subject is a human.

BRIEF DESCRIPTION OF THE DRAWINGS

FIG. 1 depicts the CPS repeating blocks of serotype complexes HS1, HS3, HS4, and HS23/36 and the strain specific heptose units and O-methyl phosphoramidate (MeOPN) linkages. Abbreviations: "±", MeOPN moieties in non-stoichiometric amounts; Gal, galactose; Gro, glycerol; Fru, fructose; Hep, heptose; GlcpNAc, N-acetyl-D-glucosamine. The existence of MeOPN-6-Gal in strain HS23/36 is based on the discovery reported herein.

FIG. 6(A) depicts the structure of possible MeOPN modified monosaccharides on MeOPN-6 Gal in the CPS of the HS 23/36 serotype of C. jejuni. All "R" groups present can stand for either H or MeOPN, i.e., each site of modification (Gal-2 or Gal-6) can be substituted with either H or MeOPN. FIG. 6(B) depicts the structure of MeOPN modified monosaccharide in the CPSs of the indicated serotypes of C. jejuni, HS:4, HS:1, and HS:3. In order to test for capsule cross-reactivity, a spot of MeOPN-6-Gal was combined with the indicated detecting anti-$CRM_{197}$ conjugate antiserum (indicated on the right side of the blot). Data indicate that antibodies to HS23/36, HS4 and HS1 serotypes of C. jejuni can react with the synthetic MeOPN-6-Gal construct.

FIG. 16(B) provides the blot of the construct. The gel and blot were prepared using conventional methods as described in Example 7.

FIG. 19(B) depicts a cartoon of genes in the variable CPS locus of 81-176. The variable CPS locus of 81-176 maps between kpsC (CJJ81176_1413c) and kpsF (CJJ181176_1437c) shown in grey and encompasses 22 genes. Genes of known function are labeled. Those genes that involved in synthesis of MeOPN are labeled as mpnA-D ([21]) and the remaining genes are involved in heptose synthesis. Genes in black represent the two putative MeOPN transferases, CJJ81176_1420 and CJJ81176_1435.

DETAILED DESCRIPTION

Figure 2:
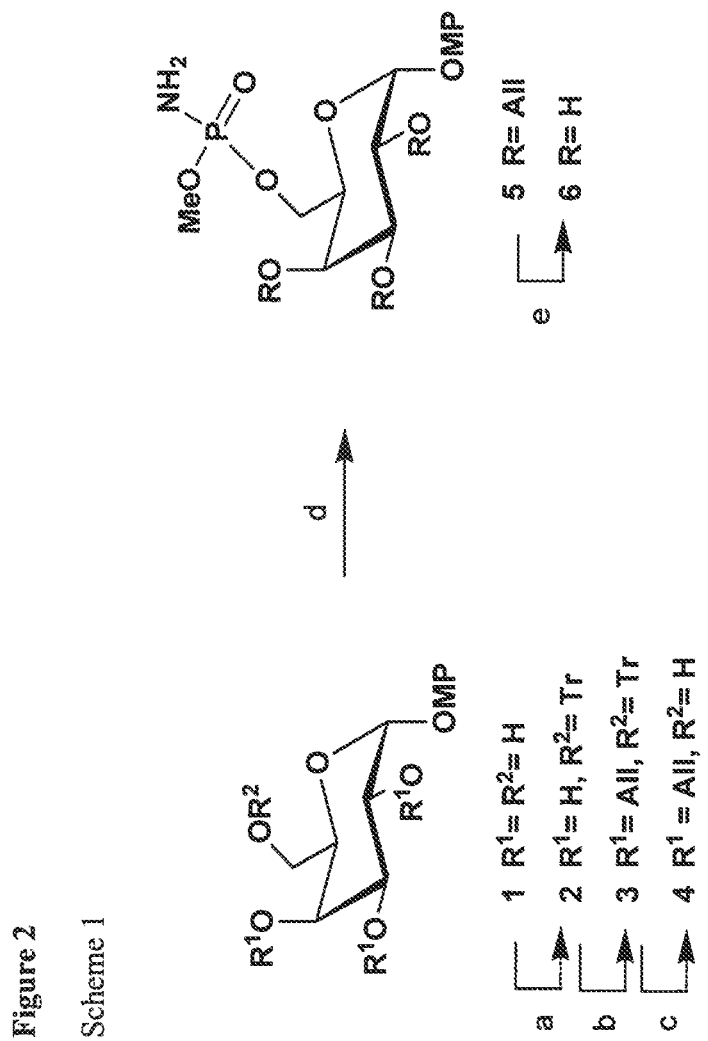
FIG. 2 depicts synthesis of the p-methoxyphenyl glycoside of the MeOPN→6-Gal construct (O-Me-phosphoramidate galactoside), MeOPN→6-α-D-Galp-(1→OMP ("Scheme 1".) The reagents and conditions employed in the steps indicated therein are as follows: (a) TrCl, pyridine, 95%; (b) AllBr, NaH, DMF, 0° C., 89%; (c) 80% AcOH, 80° C., 78%; (d) $PCl_2(O)OMe$, $Et_3N$, $CH_2Cl_2$, then $NH_3$ (g), 19%; (e) $PdCl_2$, MeOH, 39%. Tr, trityl; All, allyl; DMF, dimethyl formamide; OMP, 4-methoxyphenyl group.

While the specification concludes with the claims particularly pointing out and distinctly claiming the invention, it is believed that the present invention will be better understood from the following description.

All percentages and ratios used herein are by weight of the total composition unless otherwise indicated herein. All temperatures are in degrees Celsius unless specified otherwise. All measurements made are at 25° C. and normal pressure unless otherwise designated. The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention.

All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value. Unless otherwise indicated, as used herein, "a" and "an" include the plural, such that, e.g., "a MeOPN-6-Gal monosaccharide" can mean at least one MeOPN-6-Gal monosaccharide, as well as a plurality of MeOPN-6-Gal monosaccharides, i.e., more than one MeOPN-6-Gal monosaccharide.

Where used herein, the term "and/or" when used in a list of two or more items means that any one of the listed characteristics can be present, or any combination of two or more of the listed characteristics can be present. For example, if a vaccine formulation against *C. jejuni* is described as containing characteristics A, B, and/or C, the vaccine formulation against *C. jejuni* can contain A feature alone; B alone; C alone; A and B in combination; A and C in combination; B and C in combination; or A, B, and C in combination. The entire teachings of any patents, patent applications or other publications referred to herein are incorporated by reference herein as if fully set forth herein.

Until recently, MeOPN-2-Gal was thought to be the only MeOPN moiety on CPS Gal in *C. jejuni* strain 81476 (otherwise referred to herein as serotype HS23/26.) (Kanipes et al., (2006) *J Bacteriol.* 188, 3273-3279.) By performing genetic and structural analyses of *C. jejuni* strain HS23/36, however, the inventors have surprisingly discovered a second distinct MeOPN at the O-6-position of the CPS Gal. As reported herein, the inventors have discovered that although present in non-stoichiometric amounts, CPS epitopes containing MeOPN units are key *C. jejuni* immunogenic markers. Moreover, by performing comprehensive immunological analyses of multivalent conjugate vaccines using native CPSs of *C. jejuni* HS23/36, the inventors have discovered that the MeOPN-6-Gal monosaccharide is immunogenic and immunodominant over MeOPN-2-Gal and unmodified polysaccharide.

In view of the foregoing, the present invention is directed to an immunogenic synthetic construct capable of inducing an immune response against *C. jejuni* in a subject. Specifically, in contrast to previous anti-*C. jejuni* immunogenic polysaccharide constructs or CPS conjugate vaccines, the instant invention is directed to an immunogenic synthetic construct against *C. jejuni* comprising one or more methyl phosphoramidyl monosaccharides, i.e., an immunogenic synthetic construct comprising one or more O-methyl phosphoramidate (MeOPN) moieties, including but not limited to, MeOPN at the 6 position of galactose.

In a particular embodiment, as specifically described in detail herein, the enhanced immunogenicity and efficacy of a synthetic MeOPN→6 Gal construct against *C. jejuni* has surprisingly been discovered. Thus, in various aspects, the invention includes a synthetic saccharide construct that comprises one or more synthetic MeOPN→6 Gal monosaccharides, compositions comprising these synthetic saccharide constructs, and methods of using these synthetic saccharide constructs. In a particular embodiment, the synthetic saccharide construct is conjugated to a carrier protein. Compositions, e.g., pharmaceutical anti-*C. jejuni* formulations, including vaccine formulations, comprising the synthetic construct (unconjugated or conjugated to a carrier protein) are contemplated herein. Also contemplated herein are methods of inducing an immune response against *C. jejuni* in a subject comprising administering to the subject an effective amount of the synthetic construct and/or a composition of the instant invention, e.g., a vaccine formulation, comprising the synthetic construct in conjugated and/or unconjugated forms.

The immunogenic synthetic constructs and conjugates of the instant invention are believed to offer multiple advantages over previous conjugate vaccines made from purified *C. jejuni* capsule polysaccharides. For example, data indicate that MeOPN moieties are phase variable in *C. jejuni*, thus the level of this epitope normally present in vaccine formulations obtained from purified capsules can vary. As a result of this natural variability, different preparations from the same strain of *C. jejuni* may have different levels of this MeOPN epitope, and thus different immunogenicity. In contrast, by using a synthetic approach, a pharmaceutical formulation (e.g., a vaccine formulation) comprising a desired level of MeOPN epitopes can be obtained, and provides the advantage that the potential immunogenicity of the vaccine may be controlled. In addition, as evident from the examples provided herein, the synthetic *C. jejuni* monosaccharide construct antigen of the instant invention appears to have broader coverage than polysaccharides, thus potentially reducing the valency required for a vaccine against *C. jejuni*. Thus, it is contemplated herein that the synthetic constructs disclosed herein are antigenic determinants that can be used as effective antigens in a vaccine formulation in which a single epitope could cross-protect across more than one *C. jejuni* serotype. Moreover, since the use of the synthetic construct of the instant invention eliminates the need to grow *C. jejuni* (a fastidious organism) and to purify the capsule, the synthetic construct is more cost-effective and thus provides a commercial advantage compared to other vaccines which use purified CPS.

In addition to the foregoing, the synthetic construct of the instant invention is not only immunogenic, but also provides the advantage that the synthetic approach precludes concerns about development of autoimmunity because the method does not require purification of capsules away from *C. jejuni* lipooligosaccharides (LOS) which often contains structures that mimic human gangliosides structurally and can induce an autoimmune response that results in Guillain Barré Syndrome.

As understood by one of skill in the art, "MeOPN→6 Gal", "MeOPN-6-Gal", "MeOPN-6-Gal construct" and like terms refer to a galactose monosaccharide which is modified to include an O-methyl phosphoramidate moiety at the O-6 position of the galactose monosaccharide. As understood herein, the synthetic MeOPN-6-Gal construct may comprise various other "R" groups in addition to the MeOPN moiety. The term encompasses constructs of various modified forms, e.g., MeOPN→6-α-D-Galp-(1→OMP, i.e., 4-Methoxyphenyl 6-O-methyl-phosphoramidate-α-D-galactopyranoside; as well as activated forms including a linker, e.g., as MeOPN→6-β-D-Galp-(1→O(CH$_2$)$_5$NH$_2$, i.e., 5-Aminopentanyl 6-O-methylphosphoramidate-β-D-galactopyranoside. Similarly, "MeOPN-2-Gal" and like terms refers to an O-methyl phosphoramidate moiety at the O-2 position of the galactose monosaccharide.

As understood herein, an "immunogenic synthetic construct" or more simply "synthetic construct", and like terms, refer to an in vitro, i.e., chemically produced, non-naturally occurring ("man-made") compound comprising one or more monosaccharides comprising one or more MeOPN moieties capable of inducing an immune response against *Campylobacter jejuni* (*C. jejuni*) in a subject. In a particular embodiment, the immunogenic synthetic construct comprises one or more MeOPN→6 Gal monosaccharides which can elicit an immune response to *C. jejuni* in a subject. The MeOPN→6 Gal monosaccharide may also comprise various other "R" groups in addition to the MeOPN moiety. As contemplated herein, in a particular embodiment, the immunogenic synthetic construct of the instant invention comprises one or more synthetic MeOPN→6 Gal monosaccharides, alone or chemically associated in combination with one or more other saccharides, and/or chemical linkers. For example, it is contemplated herein that the synthetic construct of the present invention can comprise one or more additional monosaccharides in combination with one or more MeOPN-6-Gal monosaccharides. Monosaccharides found in the CPS of *C. jejuni* are particularly contemplated herein, e.g., one or more of fructose, galactose, glucose, or heptose monosaccharides, and optionally substituted with one or more additional MeOPN moieties, including but not limited to, MeOPN-2-Gal, or other antigens against *C. jejuni*.

As discussed below in detail, it is contemplated herein that the synthetic constructs of the instant invention, including synthetic constructs comprising one or more MeOPN→6 Gal monosaccharides, may be activated and conjugated to a carrier protein or may be used in an unconjugated form. When conjugated to a carrier protein, the synthetic construct may be referred to herein as a "conjugate vaccine" or as a "conjugate."

As used herein, "a subject" includes an animal, including but not limited to birds and mammals. Human beings are also encompassed in this term. As particularly contemplated herein, subjects include, e.g., any animal or human that has been infected with, or is at risk of being infected with, *C. jejuni*. A subject may be nave, or non-naive with regard to *C. jejuni* exposure. In particular, suitable subjects (patients) include, but are not limited to, farm animals (e.g., chickens) as well as non-human primates and human patients.

As understood herein, the synthetic construct of the instant invention may be administered to a subject in order to induce an immune response in the subject and thus prevent and/or ameliorate one or more pathological conditions associated with *C. jejuni* in the subject. As understood herein, the concept of "inducing" an immune response in a subject refers to triggering a humoral and/or cellular immune response in the subject.

The concept of "preventing and/or ameliorating" one or more pathological conditions associated with *C. jejuni* encompasses, e.g., averting or hindering the onset or development of a pathological condition associated with *C. jejuni* infection, as well as treating, curing, retarding, and/or reducing the severity of one or more pathological conditions associated with *C. jejuni*.

As used herein, the term "one or more pathological conditions associated with *C. jejuni*" refers to an undesirable condition in a subject caused by infection with *C. jejuni* ("campylobacteriosis".) As contemplated herein, such pathological conditions include clinical conditions and diseases which may arise in a subject upon infection with *C. jejuni*, as well as conditions which may develop in a subject as a consequence of a previous instance of campylobacteriosis. These conditions are familiar to one of skill in the art and include, but are not limited, to *campylobacter* gastroenteritis, Reiter's Syndrome, inflammatory bowel syndrome, and Guillain-Barré Syndrome (GBS.)

Synthesis of the synthetic constructs of the instant invention, including the controlled synthesis and introduction of MeOPN to a simple sugar, activation of the resulting synthetic construct, addition of a chemical linker, and conjugation of a carrier protein may be performed using commercially available materials and methodologies familiar to a carbohydrate chemist. Particular methods of synthesis (synthesis schemes) are described in detail in the below examples. It is contemplated herein that the methods of synthesizing the compounds disclosed in the below examples and "schemes" are included among the aspects of the instant invention.

As understood by one of skill in the art, the chemical synthesis of a monosaccharide may be achieved using well-established procedures in carbohydrate chemistry; however, monosaccharides for use as starting compounds in the disclosed synthesis schemes may be obtained from a variety of commercial vendors and chemically modified by one of skill in the art to arrive at the immunogenic synthetic construct of the instant invention, e.g., according to the synthesis schemes disclosed herein. Published chemical modifications include, but are not limited to, the method for the synthesis of 4-methoxyphenyl-α-D-galactopyranoside proposed in Comfort, et al., Biochem. 46: 3319-3330 (2007.) Briefly, 4-methoxyphenyl-α-D-galactopyranoside may be synthesized from D-galactose by acetylation, glycosidation with 4-methoxyphenol, followed by Zemplén deacetylation according to published methods. (Montgomery et al. (1942) *J. Am. Chem. Soc.* 64, 690-694.)

Similarly, various strategies for the synthesis and introduction of MeOPN to a monosaccharide are familiar to one of skill in the art. A particular method is described in C. Mara et al, *Bioorg. Med. Chem. Lett.* 6180-6183 (2011.) This reference describes the reaction with ethyl dichlorophosphate followed by reaction with protected amines.

As discussed above, the synthetic construct of the instant invention may be chemically activated in order to add one or more chemical linking group(s) capable of reacting with a carrier protein. As contemplated herein, the activation of a construct of the instant invention may be performed according to conventional methods familiar to one of skill in the art. Such methods include, e.g., the use of cyanylating reagents such as 1-cyano-4-dimethylamino pyridinium tetrafluoroborate (CDAP); carbodiimides, hydrazides, active esters, p-nitrobenzoic acid, N-hydroxysuccinimide, and trimethylsilyl trifluoromethanesulfonate (TMSOTf.) Activating the construct may also be achieved by reacting the saccharide with 2,2,6,6-tetramethylpiperidin-1-oxyl (TEMPO.) See, e.g., US Pub. No. 2014/0141032.

While the immunogenic synthetic constructs of the instant invention may be administered to a subject in an unconjugated form, it is contemplated herein that upon synthesis, the construct may be chemically activated and chemically conjugated in vitro to one or more carrier molecules, e.g., one or more T cell-dependent carrier proteins prior to administration in order to provide an enhanced immune response. Indeed, as appreciated by one of skill in the art, children are only capable of mounting an IgM response in the face of polysaccharide antigens; adults are capable of generating an IgG, IgA and IgM response. Thus, by linking a carrier protein to the synthetic construct, the immune response triggered in vivo by the construct will change from a T-cell independent response to one which is T-cell dependent. As such, the immune response that is triggered is enhanced and thus markedly different than what might otherwise be produced in vivo by an unconjugated construct.

In a particular embodiment, the carrier molecule is a carrier protein. As used herein, a "carrier protein" refers to a protein, or an analog or fragment thereof, which ideally contains at least one T-cell epitope. Suitable carrier proteins for use with the instant invention are familiar to one of skill in the art and are commercially available and/or may be created and purified by one of skill in the art using conventional methods. For example, carrier proteins for use with the instant invention include bacterial toxins that are immunologically effective carriers and that have been rendered safe by chemical or genetic means for administration to a subject. Examples include, but are not limited to, inactivated bacterial toxins such as diphtheria toxoid, $CRM_{197}$, tetanus toxoid, pertussis toxoid, *E. coli* heat labile enterotoxin (LT), the binding component of *E. coli* heat labile enterotoxin (LTB), *E. coli* adhesins and/or fimbriae, and exotoxin A from *Pseudomonas aeruginosa*. Bacterial outer membrane proteins such as, e.g., outer membrane complex c (OmpC), porins, transferrin binding proteins, pneumococcal surface protein A (PspA), pneumococcal adhesin protein (PsaA), or pneumococcal surface proteins BVH-3 and BVH-11 can also be used. Other proteins, such as protective antigen (PA) of *Bacillus anthracis*, ovalbumin, keyhole limpet hemocyanin (KLH), human serum albumin, bovine serum albumin (BSA) and purified protein derivative of tuberculin (PPD) can also be used.

In a particular embodiment, the carrier protein is selected from the group consisting of inactivated bacterial toxins, bacterial outer membrane proteins, protective antigen (PA) of *Bacillus anthracis*, ovalbumin, keyhole limpet hemocyanin (KLH), human serum albumin, bovine serum albumin (BSA) and purified protein derivative of tuberculin (PPD.) In a particular embodiment, the inactivated bacterial toxin is selected from the group consisting of diphtheria toxoid, cross-reactive material 197 ($CRM_{197}$), tetanus toxoid, pertussis toxoid, the binding component of *E. coli* heat labile enterotoxin (LTB), *E. coli* adhesins and/or fimbriae, and exotoxin A from *Pseudomonas aeruginosa*. In a particular embodiment, the carrier protein is the inactivated bacterial toxin $CRM_{197}$. In another particular embodiment, the bacterial outer membrane protein is selected from the group consisting of outer membrane complex c (OmpC), porins, transferrin binding proteins, pneumococcal surface protein A (PspA), pneumococcal adhesin protein (PsaA), pneumococcal surface protein BVH-3, and pneumococcal surface protein BVH-11. Such carrier proteins are available from a variety of commercial vendors.

It is also contemplated herein that proteins from ETEC may be used as carrier molecules. Possible ETEC protein carriers include, but are not limited to, the B subunit of the heat labile enterotoxin, and fimbrial subunits. The latter includes subunits of various ETEC colonization factors such as, e.g., CfaI (CfaE and/or CfaB), CS6 (CssB and/or CssA), CS3 (CstG and/or CstH), CS17 (CsbA and/or CsbD) and CS1 (CooA.) Further examples of ETEC proteins and details regarding the use of ETEC proteins as possible carrier molecules can be found, e.g., in US 2015/0258201 A1, the entire contents of which are incorporated by reference herein.

As contemplated herein, a carrier protein may be linked to more than one synthetic construct in order to enhance the immunogenicity of the construct against *C. jejuni*. In one embodiment, multiple synthetic MeOPN-6-Gal constructs are linked to a single carrier protein. In a particular embodiment, a conjugate vaccine of the instant invention comprising a MeOPN-6-Gal:$CRM_{197}$ ratio (w/w) of at least 8:1 or more is envisioned herein.

After conjugation, free and conjugated saccharide constructs can be separated using a variety of conventional methods. Purification methods are familiar to one of skill in the art and include, e.g., ultrafiltration, size exclusion chromatography, density gradient centrifugation, hydrophobic interaction chromatography, and/or ammonium sulfate fractionation.

Possible methods of conjugating an activated monosaccharide or saccharide construct of the instant invention to a carrier protein are familiar to one of skill in the art and include, e.g., reductive amination of a monosaccharide involving the coupling of the resulting amino group with one end of an adipic acid linker group, and then coupling a protein to the other end of the adipic acid linker group; cyanylation conjugation, wherein the saccharide construct is activated either by cyanogens bromide (CNBr) or by 1-cyano-4-dimethylammoniumpyridinium tetrafluoroborate (CDAP) to introduce a cyanate group to the hydroxyl group, which forms a covalent bond to the amino or hydrazide group upon addition of the protein component; and a carbodiimide reaction, wherein carbodiimide activates the carboxyl group on one component of the conjugation reaction, and the activated carbonyl group reacts with the amino or hydrazide group on the other component. If necessary, these reactions may also be employed to activate the components of the carrier protein prior to the conjugation reaction. As contemplated herein, in a particular embodiment, a process involving the introduction of amino groups into the monosaccharide (e.g., by replacing terminal =O groups with —$NH_2$) followed by derivatization with an adipic diester (e.g., adipic acid N-hydroxysuccinimido diester) and reaction with carrier protein may be used.

It is also contemplated herein that the synthetic construct may be linked directly to the carrier protein. Direct linkages to the protein may comprise oxidation of the monosaccharide followed by reductive amination with the protein using conventional methods.

The synthetic constructs of the instant invention, e.g., comprising one or more MeOPN-6-Gal monosaccharides, may further comprise one or more additional saccharides, as well as one or more additional chemical compounds or moieties or fragments or derivatives thereof. A variety of chemical compounds can serve as a chemical backbone to link the various components of an immunogenic synthetic construct of the instant invention, and/or to link the synthetic construct as a whole to one or more carrier proteins. Compounds that may be used to make a polymeric construct or conjugate include, e.g., modified starch moieties, cyclodextrin, and nigeran.

As particularly contemplated herein, the construct may comprise additional saccharides, moieties, or compounds which may be incorporated for a variety of reasons, e.g., to increase the chemical stability of the synthetic construct and/or to enhance the delivery or bioavailability of the construct. In a particular embodiment, it is contemplated herein that additional saccharides, moieties, and compounds may be chemically associated with one or more MeOPN-6-Gal constructs either directly or indirectly through one or more linkers or other compounds, in order to enhance the immunogenicity of the synthetic construct against *C. jejuni* in a subject. Thus, additional saccharides for use in a synthetic construct of the instant invention include, but are not limited to, monosaccharides present in the capsule of various *C. jejuni* strains, e.g., galactose or other modified forms thereof, including MeOPN-2-Gal, fructose, glucose, heptose N-acetyl galactosamine, N-acetyl glucosamine, glucitol, glucose or modified forms or derivatives thereof, including monosaccharides containing one or more MeOPN moieties, including but not limited to MeOPN-2-Gal and MeOPN-6-Gal. Such saccharides may be used in an amount and in combination with one or more MeOPN-6-Gal monosaccharides which may enhance the immunogenicity of the synthetic construct against *C. jejuni*. For example, FIG. 1 lists the CPS repeating blocks and specific heptose units and MeOPN linkages of *C. jejuni* serotype complexes HS1, HS3, HS4, and HS23/36.

Figure 15:
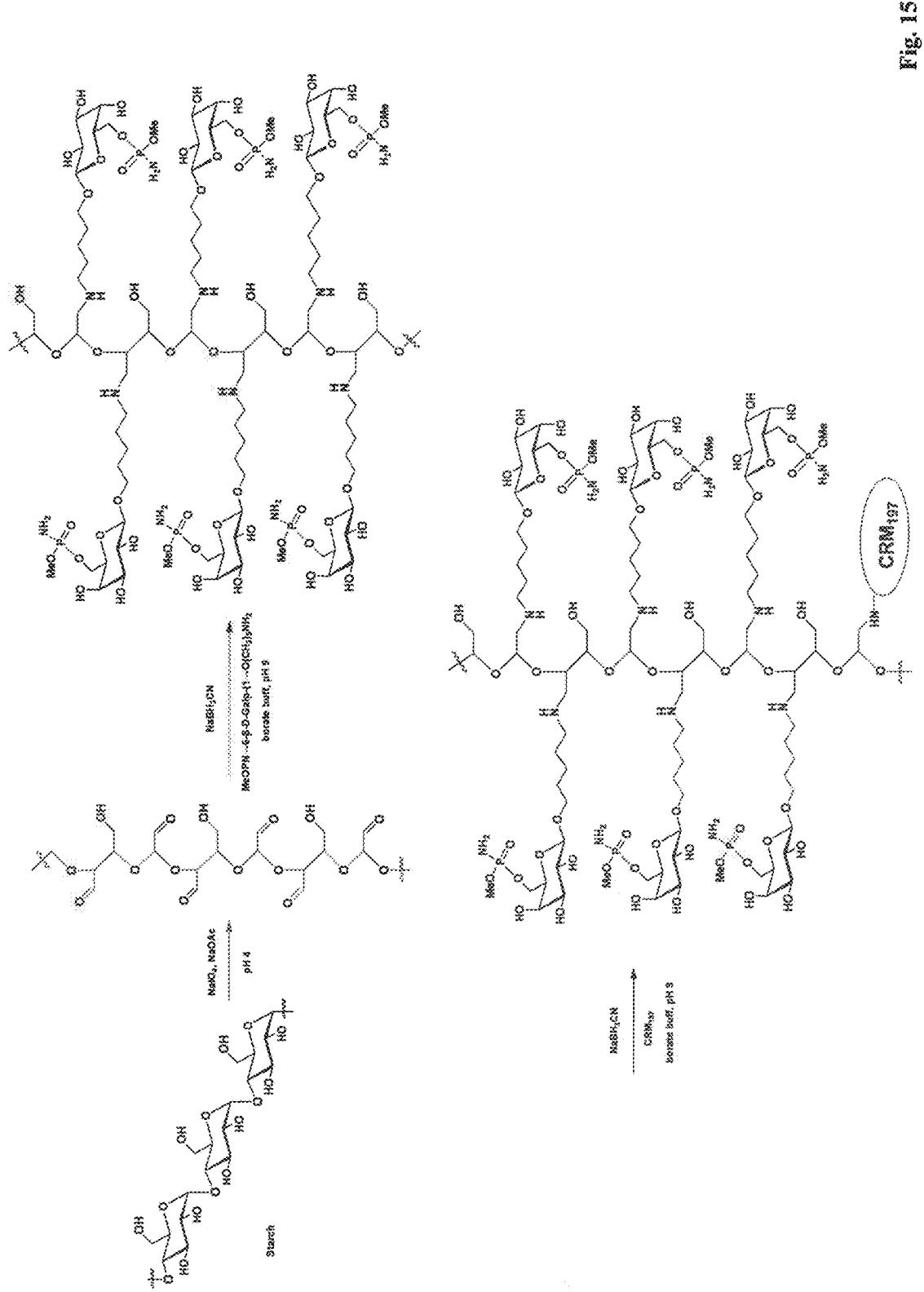
FIG. 15 depicts the synthesis of a synthetic polymeric conjugate of the invention comprising multiple MeOPN-6-Gal monosaccharides chemically associated using a starch backbone which is equipped with a linker and conjugated to the carrier protein, $CRM_{197}$.
Figure 18:
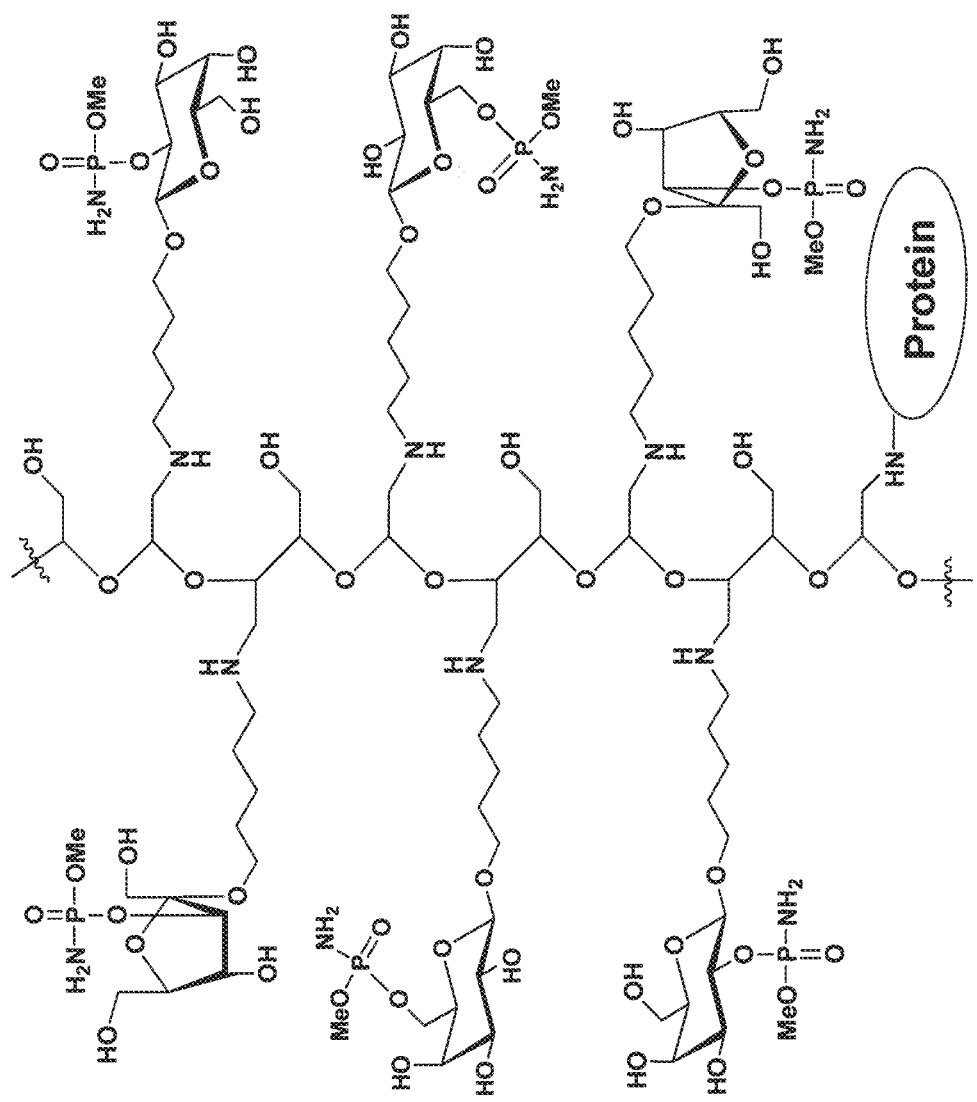
FIG. 18 depicts another synthetic polymeric construct of the invention comprising multiple MeOPN-6-Gal monosaccharides chemically associated with other saccharides using a starch backbone and which is equipped with a linker and conjugated to a carrier protein. Specifically, as depicted, the synthetic polymer comprises multiple MeOPN-6-Gal, MeOPN-2-Gal, and MeOPN-1-Fru monosaccharides.

In view of the foregoing, as provided in the below examples, FIG. 15 depicts a synthetic polymeric construct which comprises more than one MeOPN-6-Gal monosaccharide; FIG. 18 depicts a synthetic polymeric construct which comprises more than one MeOPN-6-Gal monosaccharide and also comprises additional monosaccharides MeOPN-2-Gal and MeOPN-1-Fru. It is contemplated herein that the presence of these additional components in a construct or conjugate of the instant invention will enhance the immunogenicity of the construct or conjugate against *C. jejuni*.

As understood herein, "associated" includes any manner of chemical combination, e.g., the synthetic construct may comprise several synthetic MeOPN-6-Gal monosaccharides chemically joined in a chain as a polymer, or in various combinations with any number of one or more other saccharides. Such construct may be further conjugated to a carrier protein.

As contemplated herein, the methods of the instant invention are directed to inducing an immune response against *C. jejuni* in a subject comprising administering an effective amount of the immunogenic synthetic construct to the subject. In particular embodiments, the construct is administered to the subject in the form of a composition comprising the synthetic construct as an active pharmaceutical ingredient, e.g., a pharmaceutical composition, more particularly, as a vaccine formulation comprising the synthetic construct linked to a carrier protein. Thus, as used herein, an "effective amount" can refer to the amount of the immunogenic synthetic construct alone or in a composition, including in a pharmaceutical composition comprising one or more other active pharmaceutical agents or excipients.

Moreover, as understood herein, an "effective amount" refers to an immunologically effective amount of the immunogenic synthetic construct (conjugated or unconjugated) suitable to elicit an immune response in the subject. As discussed above, an "immune response" encompasses triggering a humoral and/or cellular immune response in the subject. As a result, a meaningful clinical benefit to the subject is provided. Such benefit may be, e.g., preventing, ameliorating, treating, inhibiting, and/or reducing one of more pathological conditions associated with campylobacteriosis or related sequelae. Thus, the methods of the present invention can be considered therapeutic methods or preventative or prophylactic methods. In a particular embodiment, it is contemplated herein that the immunogenic synthetic construct and/or conjugate of the instant invention may be administered to a subject and thus prevent diarrhea caused by *C. jejuni* in the subject.

One of skill in the art will appreciate that the administration of the synthetic construct of the instant invention encompasses the use of the constructs and/or the compositions, e.g., vaccine formulations, of the instant invention to generate immunity in a subject if later challenged by infection with *C. jejuni*. It is further understood herein, however, that the synthetic constructs, conjugates, compositions, vaccine formulations and methods of the present invention do not necessarily provide total immunity to *C. jejuni* and/or totally cure or eliminate all disease symptoms.

Suitable effective amounts of the immunogenic synthetic constructs of the instant invention can be readily determined by those of skill in the art and will depend upon the age, weight, species (if non-human) and medical condition of the subject to be treated, and whether the construct is administered in a conjugated or unconjugated form. For example, initial information may be gleaned in laboratory experiments, and an effective amount for humans subsequently determined through conventional dosing trials and routine experimentation. As contemplated herein, an effective amount of the construct or conjugate for vaccination against *C. jejuni* infection may be from between about 1 µg or less to about 100 µg or more per kg body weight. As a general guide, a suitable amount of a construct or conjugate of the invention can be an amount between from about 0.1 µg to about 10 mg per dosage amount with or without an adjuvant. Moreover, immunization comprising administering one or more boosting doses may be performed using between from about 0.1 µg to about 10 mg per dose with or without adjuvant.

It is contemplated herein that the constructs and compositions of the instant invention may be administered to a subject by a variety of routes according to conventional methods, including but not limited to parenteral (e.g., by intracisternal injection and infusion techniques), intradermal, transmembranal, transdermal (including topical), intramuscular, intraperitoneal, intravenous, intra-arterial, intralesional, subcutaneous, oral, and intranasal (e.g., inhalation) routes of administration. Administration can also be by continuous infusion or bolus injection.

In addition, the compositions of the instant invention can be administered in a variety of dosage forms. These include, e.g., liquid preparations and suspensions, including, preparations for parenteral, subcutaneous, intradermal, intramuscular, intraperitoneal or intravenous administration (e.g., injectable administration), such as sterile isotonic aqueous solutions, suspensions, emulsions or viscous compositions that may be buffered to a selected pH. In a particular embodiment, it is contemplated herein that the constructs and compositions of the instant invention are administered to a subject as an injectable, including but not limited to injectable compositions for delivery by intramuscular, intravenous, subcutaneous, or transdermal injection. Such compositions may be formulated using a variety of pharmaceutical excipients, carriers or diluents familiar to one of skill in the art.

In another particular embodiment, the synthetic immunogenic construct and compositions of the instant invention may be administered orally. Oral formulations for administration according to the methods of the present invention may include a variety of dosage forms, e.g., solutions, powders, suspensions, tablets, pills, capsules, caplets, sustained release formulations, or preparations which are time-released or which have a liquid filling, e.g., gelatin covered liquid, whereby the gelatin is dissolved in the stomach for delivery to the gut. Such formulations may include a variety of pharmaceutically acceptable excipients described herein, including but not limited to mannitol, lactose, starch, magnesium stearate, sodium saccharine, cellulose, and magnesium carbonate.

In a particular embodiment, it is contemplated herein that a composition for oral administration may be a liquid formulation. Such formulations may comprise a pharmaceutically acceptable thickening agent which can create a composition with enhanced viscosity which facilitates mucosal delivery of the immunogen, e.g., by providing extended contact with the lining of the stomach. Such viscous compositions may be made by one of skill in the art employing conventional methods and employing pharmaceutical excipients and reagents, e.g., methylcellulose, xanthan gum, carboxymethyl cellulose, hydroxypropyl cellulose, and carbomer.

Other dosage forms suitable for nasal or respiratory (mucosal) administration, e.g., in the form of a squeeze spray dispenser, pump dispenser or aerosol dispenser, are contemplated herein. Dosage forms suitable for rectal or vaginal delivery are also contemplated herein. The constructs, conjugates, and compositions of the instant invention may also be lyophilized and may be delivered to a subject with or without rehydration using conventional methods.

As understood herein, the methods of the instant invention comprise administering the immunogenic synthetic construct to a subject according to various regimens, i.e., in an amount and in a manner and for a time sufficient to provide a clinically meaningful benefit to the subject. Suitable administration regimens for use with the instant invention may be determined by one of skill in the art according to conventional methods. For example, it is contemplated herein that an effective amount may be administered to a subject as a single dose, a series of multiple doses administered over a period of days, or a single dose followed by a boosting dose thereafter, e.g., several years later. The term "dose" or "dosage" as used herein refers to physically discrete units suitable for administration to a subject, each dosage containing a predetermined quantity of the synthetic construct and/or conjugate as the active pharmaceutical ingredient calculated to produce a desired response.

The administrative regimen, e.g., the quantity to be administered, the number of treatments, and effective amount per unit dose, etc. will depend on the judgment of the practitioner and are peculiar to each subject. Factors to be considered in this regard include physical and clinical state of the subject, route of administration, intended goal of treatment, as well as the potency, stability, and toxicity of the particular construct, conjugate or composition. As understood by one of skill in the art, a "boosting dose" may comprise the same dosage amount as the initial dosage, or a different dosage amount. Indeed, when a series of immunizations is administered in order to produce a desired immune response in the subject, one of skill in the art will appreciate that in that case, an "effective amount" may encompass more than one administered dosage amount.

As contemplated herein, the compositions of the instant invention, and particularly pharmaceutical compositions and vaccines of the instant invention, are preferably sterile and contain an amount of the construct and/or conjugate vaccine in a unit of weight or volume suitable for administration to a subject. The volume of the composition administered to a subject (dosage unit) will depend on the method of administration and is discernible by one of skill in the art. For example, in the case of an injectable, the volume administered typically may be between 0.1 and 1.0 ml, preferably approximately 0.5 ml.

As understood herein, a "pharmaceutical composition" of the instant invention comprises an immunogenic synthetic construct (unconjugated or conjugated to a carrier protein or combination thereof) in combination with one or more pharmaceutically acceptable excipients, carriers, or diluents. The term "pharmaceutically acceptable" is used to refer to a non-toxic material that is compatible with a biological system such as a cell, cell culture, tissue, or organism.

Examples of pharmaceutically acceptable excipients, carriers and diluents are familiar to one of skill in the art and can be found, e.g., in *Remington's Pharmaceutical Sciences* (latest edition), Mack Publishing Company, Easton, Pa. For example, pharmaceutically acceptable excipients include, but are not limited to, wetting or emulsifying agents, pH buffering substances, binders, stabilizers, preservatives, bulking agents, adsorbents, disinfectants, detergents, sugar alcohols, gelling or viscosity enhancing additives, flavoring agents, and colors. Pharmaceutically acceptable carriers include macromolecules such as proteins, polysaccharides, polylactic acids, polyglycolic acids, polymeric amino acids, amino acid copolymers, trehalose, lipid aggregates (such as oil droplets or liposomes), and inactive virus particles. Pharmaceutically acceptable diluents include, but are not limited to, water, saline, and glycerol.

As understood by one of skill in the art, the type and amount of pharmaceutically acceptable additional components included in the pharmaceutical compositions of the instant invention may vary, e.g., depending upon the desired route of administration and desired physical state, solubility, stability, and rate of in vivo release of the composition. For example, for administration by intravenous, cutaneous, subcutaneous, or other injection, a vaccine formulation is typically in the form of a pyrogen-free, parenterally acceptable aqueous solution of suitable pH and stability, and may contain an isotonic vehicle as well as pharmaceutical acceptable stabilizers, preservatives, buffers, antioxidants, or other additives familiar to one of skill in the art.

In a particular embodiment, pharmaceutical compositions in the form of a vaccine formulation comprising the immunogenic synthetic construct and/or conjugate of the instant invention, alone or in combination with other active agents and/or pharmaceutically acceptable excipients, are contemplated for administration to a subject as provided herein. Both monovalent vaccines (e.g., designed to immunize against a single antigen or single microorganism), and polyvalent vaccines (e.g., designed to immunize against two or more strains of the same microorganism, or against two or more microorganisms) are contemplated herein. In one embodiment, a vaccine formulation of the instant invention is a polyvalent formulation. In a particular embodiment, the vaccine formulations of the instant invention may be a polyvalent formulation against one or more strains of *C. jejuni*, including but not limited to, serotypes HS 23/36, HS1, HS2, HS3, HS4, and HS5/31. It is also contemplated herein that a polyvalent formulation of the instant invention may be directed against one or more strains of *C. jejuni* and/or other bacterial strain including those which have MeOPN-containing capsules.

The formulation of the vaccines of the present invention can be accomplished using art recognized methods. For example, in addition to an immunologically effective amount of the construct or conjugate vaccine, a "vaccine formulation" of the instant invention may further comprise one or more non-immunogenic components, e.g., one or more pharmaceutically acceptable excipients, carriers, diluents, stabilizers, preservatives, buffers, and disinfectants as discussed above. To this end, one of skill in the art will appreciate that the development of a robust and stable vaccine formulation will ideally employ various excipients and formulation parameters that will provide stability to the antigen and thus prevent aggregation, loss of protein structure, and/or chemical degradation such as oxidation and deamidation. One of skill in the art using routine experimentation and conventional methods can determine the particular pH, buffers, and stabilizers that are well suited for the development of robust and stable vaccine formulations of the instant invention. See, e.g., Morefield, G. (2011) *The APPS Journal*, 13: 191-200.

In addition, the pharmaceutical compositions, and particularly the vaccine formulations of the instant invention, may further comprise one or more adjuvants. As understood by one of skill in the art, an adjuvant is a substance that aids a subject's immune response to an antigen. An adjuvant can be used to increase the immunogenic efficacy of a vaccine, and may also have the ability to increase the stability of a vaccine formulation. Thus, faster and longer lasting immune responses may be possible in vivo through the addition of an adjuvant to a vaccine formulation. Adjuvants suitable for use with the compositions of the instant invention are familiar to one of skill in the art and are available from a variety of commercial vendors. These include, for example, glycolipids; chemokines; compounds that induce the production of cytokines and chemokines; interferons; inert carriers, such as alum, bentonite, latex, and acrylic particles; pluronic block polymers; depot formers; surface active materials, such as saponin, lysolecithin, retinal, liposomes, and pluronic polymer formulations; macrophage stimulators, such as bacterial lipopolysaccharide; alternate pathway complement activators, such as insulin, zymosan, endotoxin, and levamisole; non-ionic surfactants; poly(oxyethylene)-poly(oxypropylene) tri-block copolymers; trehalose dimycolate (TDM); cell wall skeleton (CWS); complete Freund's adjuvant; incomplete Freund's adjuvant; macrophage colony stimulating factor (M-CSF); tumor necrosis factor (TNF); 3-O-deacylated MPL; CpG oligonucleotides; polyoxyethylene ethers, polyoxyethylene esters, aluminum, Poly[di(carboxylatophenoxy)phosphazene] (PCPP), monophosphoryl lipid A, QS-21, cholera toxin and formyl methionyl peptide.

In one embodiment, the adjuvant may be selected from the group consisting of antigen delivery systems (e.g. aluminum compounds or liposomes), immunopotentiators (e.g. toll-like receptor ligands), or a combination thereof (e.g., AS01 or AS04.) These substances are familiar to one of skill in the art. In a particular embodiment, an adjuvant for use in the compositions and methods of the instant invention is selected from the group consisting of toll-like receptor ligands, aluminum phosphate, aluminum hydroxide, monophosphoryl lipid A, liposomes, and derivatives and combinations thereof. See, e.g., Alving, C. et al., 2012, *Expert Rev Vaccines* 11, 733-44; Alving, C. et al. (2012) *Curr Opin Immunol* 24, 310-5; Alving C. and Rao, M, (2008) *Vaccine* 26, 3036-3045; U.S. Pat. Nos. 6,090,406; 5,916,588.

In addition to the immunogenic synthetic construct and/or conjugate, the compositions of the instant invention may further comprise one or more other active pharmaceutical ingredient, including but not limited to, additional immunoregulatory agents. As understood herein, an immunoregulatory agent is a substance that can induce, potentiate, activate or otherwise stimulate the immune system of the subject. These immunoregulatory agents include, for example, substances selected from the group consisting of antigens of one or more strains of *C. jejuni*, antigens of ETEC, *Shigella* lipopolysaccharide structures, and unconjugated carrier proteins. (See, e.g., US 2015/0258201 A1.)

In addition, the compositions and vaccines of the instant invention may be administered alone or in combination with other vaccines, and/or other therapeutic or immunoregulatory agents. Such additional vaccines and agents may be administered to a subject in any manner, e.g., before, after, or concurrently with the immunogenic synthetic constructs and compositions of the instant invention.

The invention also provides a kit comprising the immunogenic synthetic constructs and/or compositions of the instant invention. In a particular embodiment, the kit may comprise the conjugate vaccine and instructions for administering the conjugate vaccine to a subject. The kit can optionally also contain one or more other therapeutic or immunoregulatory agents. The kit can optionally contain one or more diagnostic tools and instructions for use. For example, a composition comprising two or more vaccines can be included, or separate pharmaceutical compositions containing different vaccines or therapeutic agents. The kit can also contain separate doses of the conjugate vaccine for serial or sequential administration. The kit can contain suitable delivery devices, e.g., syringes, inhalation devices, and the like, along with instructions for administrating the compositions. The kit can optionally contain instructions for storage, reconstitution (if applicable), and administration of any or all therapeutic agents included. The kits can include a plurality of containers reflecting the number of administrations to be given to a subject. If the kit contains a first and second container, then a plurality of these can be present.

Although the invention herein has been described with reference to particular embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

EXAMPLES

Example 1

Figure 21:
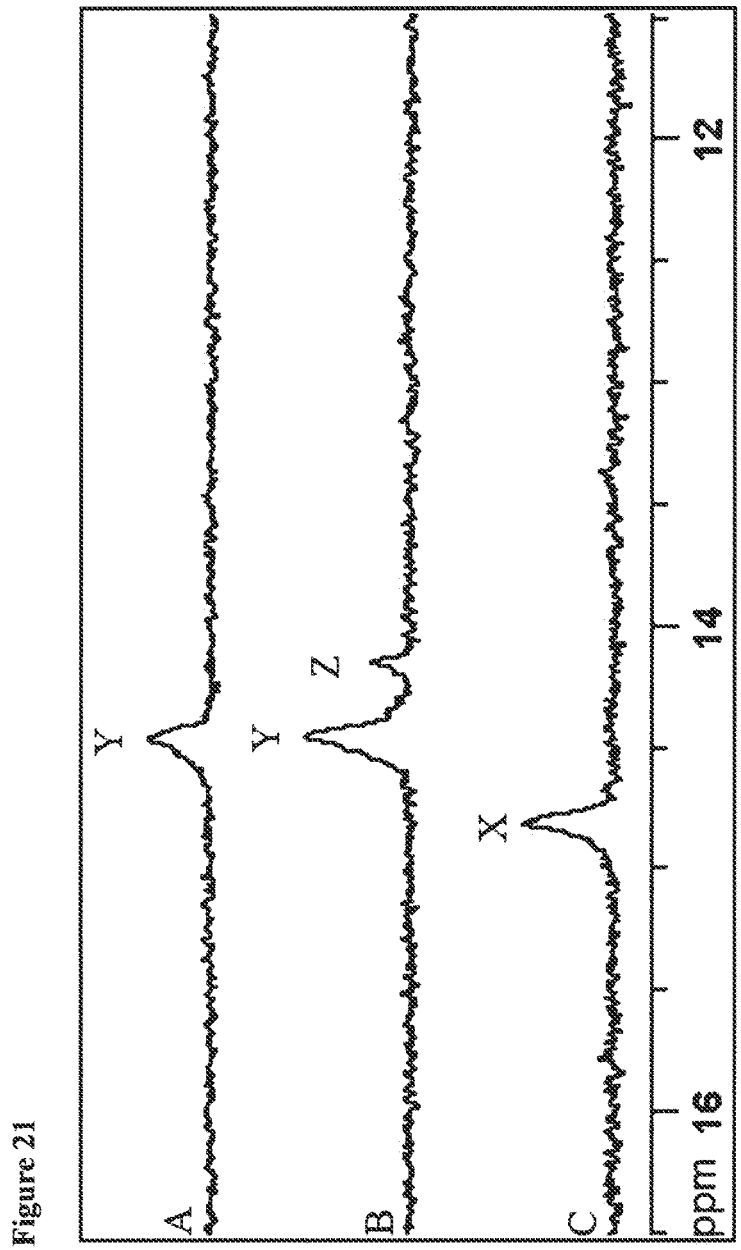
FIG. 21 depicts a 1D $^{31}P$ NMR spectra showing the three distinct MeOPN-associated resonances (X, Y and Z) discussed in this work. A. CPS of C. jejuni 81-176 wild-type that contains only one MeOPN units (peak Y). B. CPS of C. jejuni 81-176 wild-type that contains two MeOPN units (peak Y and Z). C. CPS of C. jejuni CJJ81176_1435 (3636) that contains a new MeOPN CPS modification (peak X).
Figure 22:
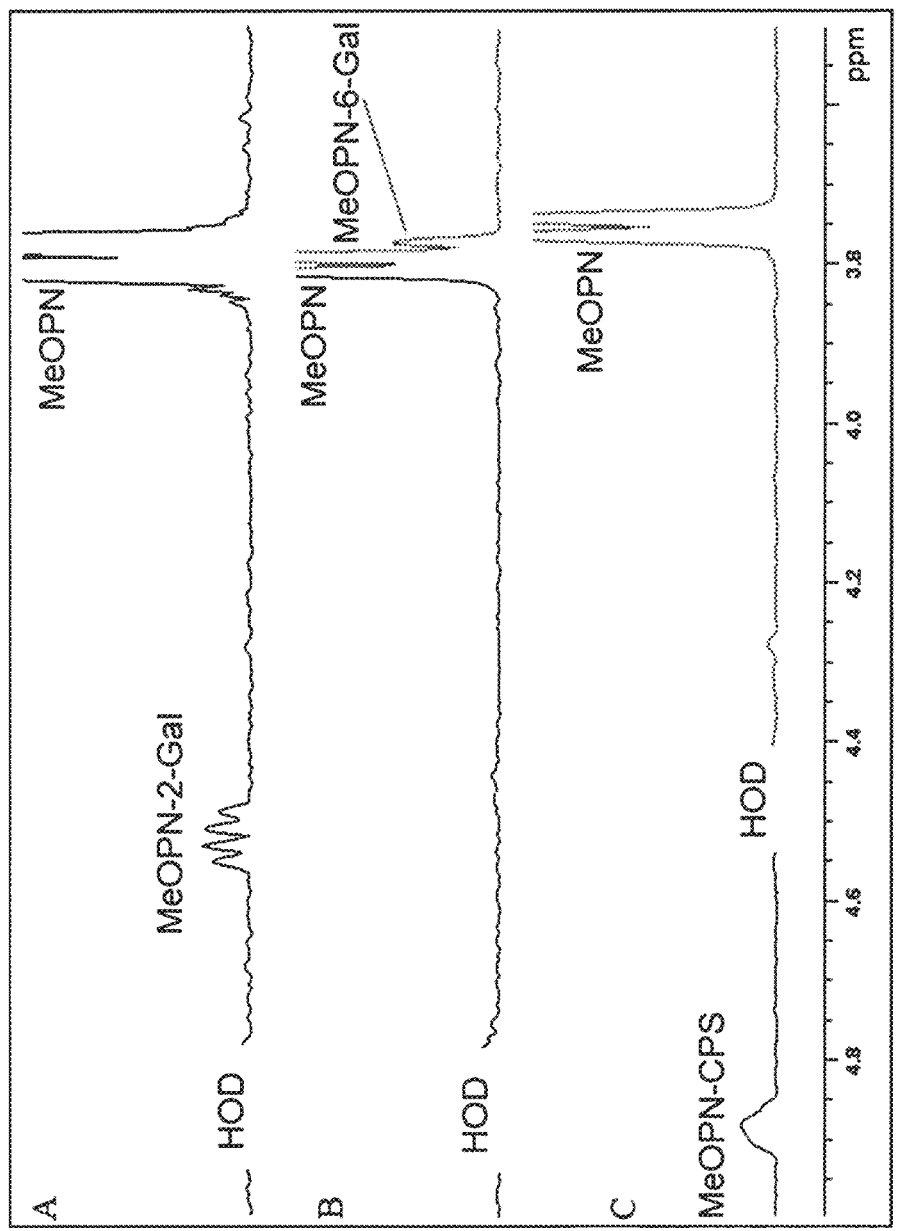
FIG. 22 depicts a 1D slices from a 2D 1H-31P Heteronuclear Multiple Bond Correlation NMR experiment. A. CPS of C. jejuni 81-176 wild-type showing the through bond correlation between MeOPN and 2-position of galactose. B. CPS of C. jejuni CJJ81176_1435 (3477) showing the through bond correlation between MeOPN and 6-position of galactose. C. CPS of C. jejuni CJJ81176_1420 (3636) showing the through bond correlation between MeOPN and an unidentified CPS position. HOD represents the position of water peak in each experiment.

Synthesis of p-methoxyphenyl and Aminopentyl Glycosides of the MeOPN→6-Gal Construct: MeOPN→6-α-D-Galp-(1→OMP and MeOPN→6-β-D-Galp-(1→O(CH$_2$)$_5$NH$_2$ Previously, using conventional methods and mass spectrometry, we detected a non-stoichiometric MeOPN unit at the 2 position of galactose (MeOPN-2-Gal) in *C. jejuni* 81-176 CPS, with a $^{31}$P resonance similar to that depicted in FIG. 21A (Peak Y) (Kanipes M I, et al. (2006.) *J. Bacteriol.* 188:3273-3279.). We continued this MeOPN-2-Gal linkage by NMR (FIG. 22A) through the detection of a cross-peak between the $^{31}$P resonance Y ($\delta_P$ 14.45) of MeOPN and H-2 ($\delta_H$ 4.52) of the galactose unit in a $^1$H-$^{31}$P correlation experiment. In some 81-176 CPS preparations, albeit of lower intensity, the $^{31}$P NMR spectrum displayed an additional resonance at $\delta_P$ 14.15 (designated peak Z) (FIG. 21B.) A similar peak was also observed in another 81-176 CPS preparation (a mutant in gene CJJ81176_1420) that exhibited a cross-peak between the phosphorus of MeOPN and H-6 resonances of some of the CPS galactose units, which resonated very near the methyl resonances of MeOPN ($\delta_H$ 3.75 to 3.81) (FIG. 22B.) The NMR data suggested that peak Z in 81-176 corresponded to a non-stoichiometric placement of MeOPN at position 6 of galactose (MeOPN-6-Gal.). These data and additional genetic studies are described in greater detail in Example 8 below.

In order to test the potential of a prototype synthetic monosaccharide anti-*C. jejuni* vaccine, p-methoxyphenyl and aminopentyl glycosides of MeOPN→6-Gal constructs, i.e., MeOPN→6-α-D-Galp-(1→OMP and MeOPN→6-β-D-Galp-(1→O(CH$_2$)$_5$NH$_2$, respectively, were synthesized. Specifically, as provided below and as depicted in FIG. 2 and FIG. 3, MeOPN→6-α-D-Galp construct may be synthesized as the p-methoxyphenyl (OMP) glycoside, MeOPN→6-α-D-Galp-(1→OMP (FIG. 2, Scheme 1) and then equipped with an aminopentyl linker at C-1 (as the β anomer) MeOPN→6-β-D-Galp-(1→O(CH$_2$)$_5$NH$_2$ for conjugation to a carrier protein (FIG. 3, Scheme 2.)

Figure 3:
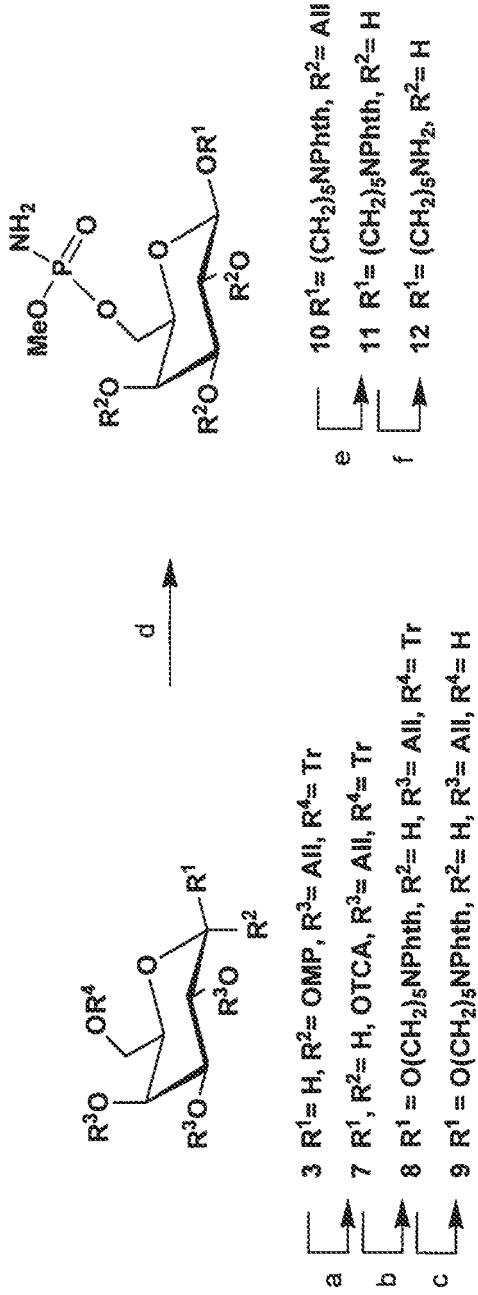
FIG. 3 depicts synthesis of the aminopentyl glycoside of the MeOPN→6-Gal construct (O-Me-phosphoramidate galactoside), MeOPN→6-β-D-Galp-(1→O(CH₂)₅NH₂ ("Scheme 2".) The reagents and conditions employed in the steps indicated therein are as follows: (a) CAN, $CH_3CN$, $H_2O$, 0° C.; then $CCl_3CN$, $K_2CO_3$, $CH_2Cl_2$, 57% over 2 steps; (b) HO(CH₂)₅NPhth, TMSOTf, $CH_2Cl_2$, 65%; (c) 80% AcOH, 80° C., 78%; (d) $PCl_2(O)OMe$, $Et_3N$, $CH_2Cl_2$, then $NH_{3(g)}$, 27%; (e) $PdCl_2$, MeOH, 75%, (f) $H_2NNH_2$, EtOH, 82%. CAN, cerium ammonium nitrate; TMSOTt; trimethylsilyl trifluoromethanesulfonate; Tr, trityl; All, allyl; OMP, 4-methoxyphenyl group; OTCA, trichloroacetimidate.

Summary Synthesis of
MeOPN→6-α-D-Galp-(1→OMP (FIG. 2, Scheme 1)

Since MeOPN can be readily removed in mild acidic media, a suitable synthetic strategy circumventing such conditions was needed. As a starting compound, 4-methoxyphenyl-α-D-galactopyranoside was synthesized according to published methods. (See, Comfort, et al., *Biochem.* 46:3319-3330 (2007).) Briefly, 4-methoxyphenyl-α-D-galactopyranoside was synthesized from D-galactose by acetylation, glycosidation with 4-methoxyphenol, followed by Zemplén deacetylation according to published methods. (Montgomery et al. (1942) *J. Am. Chem. Soc.* 64, 690-694).

Starting from 4-methoxyphenyl-α-D-galactopyranoside (compound 1), a trityl group was selectively introduced to the 6-position. Originally, benzoylation was performed on compound 2, but the extensive migration observed during the introduction of MeOPN required the elucidation of a more suitable protecting group. Allyl groups were thus selected to protect the C-2, C-3 and C-4 positions which were resistant to migration. The allyl groups were later deprotected with catalytic hydrogenolysis, yielding compound 3, which proved to be compatible with the MeOPN modification. Next, the trityl group was removed giving compound 4 exposing 6-OH for modification.

The strategy for the introduction of MeOPN is similar to a published reaction. (See Mara et al, *Bioorg. Med. Chem. Lett.* 6180-6183 (2011.) Compound 4 was treated with commercially available methyl dichlorophosphate in the presence of triethyl amine, followed by ammonolysis. Due to the dual chiral nature of the newly introduced MeOPN, product 5 was collected as a mixture of two diastereoisomers. $^{31}$P NMR was able to confirm that product 5 was indeed a 1:1 mixture of two diastereoisomers, revealing two phosphorus signals at 10.5 ppm. $^1$H NMR also revealed two sets of signals with two anomeric and two OCH$_3$ signals (data not shown.)

Figure 13:
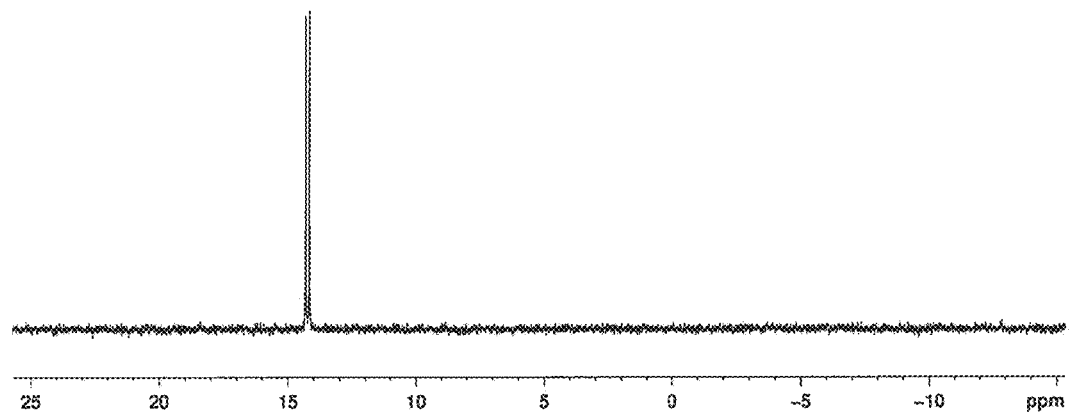
FIG. 13 depicts $^{31}P$ NMR (A) and $^1H$ NMR (B) spectra of MeOPN→6-α-D-Galp-(1→OMP performed using conventional methods.
Figure 13:
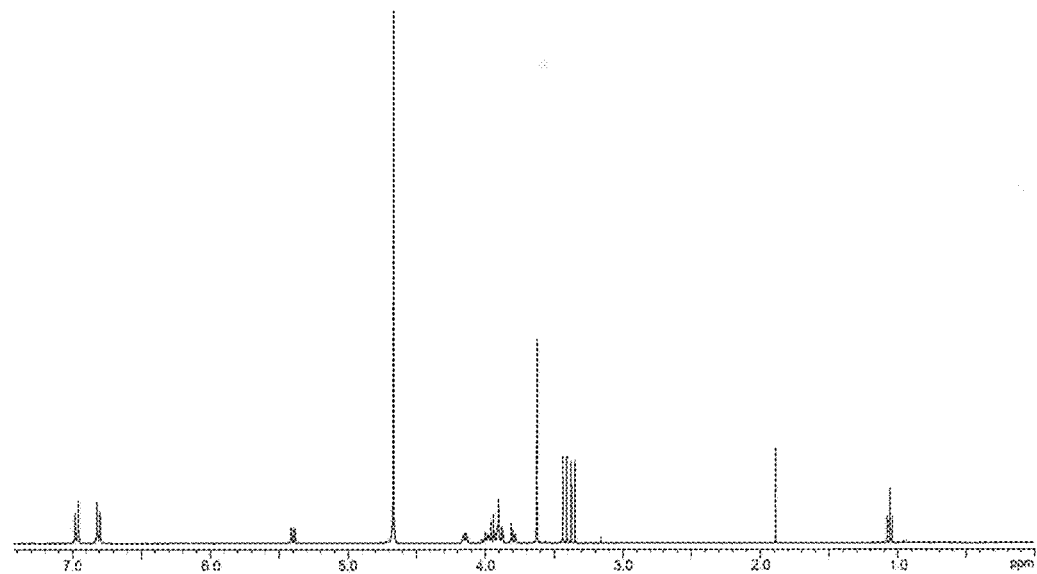

The reaction yielded a mixture of side products, the most abundant being the replacement of the O-methyl group by a second NH$_2$. Removal of the allyl group with palladium (II) chloride generated product 6. Similar to compound 5, a mixture of diastereoisomers was observed by $^1$H and $^{31}$P NMR (FIG. 13). A 2D $^1$H-$^{31}$P HMBC NMR experiment was able to confirm that the MeOPN was introduced to the O-6 position, showing correlation signals between phosphorus with both H-6 signals and OCH$_3$.

Summary Synthesis of MeOPN→6-β-D-Galp-(1→O(CH$_2$)$_5$NH$_2$ (FIG. 3, Scheme 2)

After successfully designing a strategy for the MeOPN modification, the construct was joined to a linker in order to make a vaccine conjugate. First, the 4-methoxyphenyl (OMP) was removed from galactoside (compound 3 in FIG. 2.) The corresponding hemiacetal was converted into the trichloroacetimidate donor (compound 7). The 5-amino-N-phthalimido-pentanyl linker was then introduced with TMSOTf as the activator at 0° C. Compound 8 was collected with 65% in the β and 29% in the α anomer. The removal of trityl group afforded compound 9 with a free hydroxyl group for the introduction of MeOPN. Using the procedure described above, phosphoramidate (compound 10) was collected as a mixture of two diastereoisomers. Allyl and phthalimido protecting groups were subsequently removed giving compound 11 and then compound 12.

Materials and Methods:

The compounds were synthesized using conventional methods and all chemicals were purchased from commercial suppliers and used as received. Molecular sieves were activated by heating with a heating mantle under reduced pressure. Thin layer chromatography (TLC) was carried out on TLC silica gel F$_{254}$. Sugar compounds were visualized by UV light or by charring with 10% H$_2$SO$_4$ in ethanol. Flash chromatography was performed with silica gel P60, (43-60 µm, 230-400 mesh.) $^1$H NMR and $^{13}$C NMR spectra were recorded with Bruker 400 or 600 MHz spectrometers (Bruker Daltonics Inc, Billerica, Mass.) The proton signal of residual, non-deuterated solvent (δ 7.24 ppm for CHCl$_3$) was used as internal reference for $^1$H spectra. For $^{13}$C spectra, the chemical shifts are reported relative to the solvent (δ 77.1 ppm for CDCl$_3$.) Chemical shifts are reported in parts per million (ppm.) Coupling constants are reported in Hertz (Hz.) The following abbreviations are used to indicate the multiplicities: s, singlet; d, doublet; t, triplet; m, multiplet. Optical rotations were measured on a Rudolph Research Autopol III automatic polarimeter (Rudolph Research Analytical, Hackettstown, N.J.) and concentration (c) is expressed in g/100 ml. High-resolution mass spectra for the synthetic compounds were recorded by electron spray ionization mass spectroscopy (time of flight analyzer.)

4-Methoxyphenyl 6-O-trityl-α-D-galactopyranoside (Compound 2)

To a solution of compound 1 (2.7 g, 9.3 mmol) dissolved in pyridine (40 mL), trityl chloride (3.1 g, 11 mmol) was added and the reaction mixture was stirred at 60° C. for 3 days. The reaction mixture was then concentrated and purified with flash chromatography (1:1 EtOAc-hexanes) to yield compound 2 (4.7 g, 95%.) $^1$H NMR (400 MHz, CDCl$_3$): δ 7.44-7.20 (m, 15H, Ar—H); 7.11-6.83 (m, 4H, MeOC$_6$H$_4$); 5.51 (d, 1H, J=3.6 Hz, H-1); 4.05-3.93 (m, 4H, H-2, H-3, H-4, H-5); 3.79 (s, 3H, OCH$_3$); 3.54-3.32 (m, 2H, H-6.) $^{13}$C NMR (100 MHz, CDCl$_3$): δ 155.3, 151.2, 150.6, 144.3, 143.8, 143.7, 143.6, 129.1, 128.6, 128.0, 127.9, 127.8, 127.5, 127.3, 127.1, 127.0, 118.5, 117.9, 114.6, 114.5, 114.4 (Ar); 98.4 (C-1); 87.0, 71.2, 70.0, 69.3 (C-2, C-3, C-4, C-5); 63.6 (C-6); 55.6 ($CH_3$.) HRMS (ESI): Calcd. For $C_{32}H_{32}O_7$ [M+Na]$^+$: 551.2046, found: 551.2021.

4-Methoxyphenyl 2,3,4-tri-O-allyl-6-O-trityl-α-D-galactopyranoside (Compound 3)

A solution of compound 2 (4.7 g, 8.8 mmol) dissolved in DMF (60 mL) with allyl bromide (4.6 mL, 53 mmol) was cooled to 0° C. Sodium hydride, 60% dispersion in mineral oil (1.2 g, 29 mmol) was added and the reaction mixture was stirred for 1 h at 0° C. The reaction was then quenched with MeOH (10 mL), poured into ice-cold water (100 mL) and extracted with EtOAc (3×100 mL.) The organic layer was dried over $Na_2SO_4$ and concentrated. Purification by flash chromatography eluting with 1:7 EtOAc-hexanes gave compound 3 (5.1 g, 89%.) $[\alpha]_D^{25}$=+132.6° (c+0.1, $CHCl_3$); $^1$H NMR (400 MHz, $CDCl_3$): δ 7.38-7.18 (m, 15H, Ar—H); 7.10-6.75 (m, 4H, $MeOC_6H_4$); 6.00-5.53 (m, 3H, $CH_2$—CH=$CH_2$); 5.42 (d, 1H, J=3.2 Hz, H-1); 5.33-4.98 (m, 6H, $CH_2$—CH=$CH_2$); 4.37-3.72 (m, 13H, $CH_2$—CH=$CH_2$, H-2, H-3, H-4, H-5, $OCH_3$); 3.38 (m, 1H, H-6a); 3.01 (m, H-6b.) $^{13}$C NMR (100 MHz, $CDCl_3$): δ 155.0, 151.0, 143.9 (Ar); 135.2, 135.1, 135.0 ($CH_2$—CH=$CH_2$); 128.6, 127.8, 127.0, 119.0, 117.4, 117.3, 116.4, 114.4 ($CH_2$—CH=$CH_2$, Ar); 97.5 (C-1); 86.8; 78.2 (C-2); 77.4 (C-3); 76.1 (C-5); 73.9, 72.5, 71.9 ($CH_2$—CH=$CH_2$); 70.4 (C-3) 63.3 (C-6); 55.6 ($OCH_3$.) HRMS (ESI): Calcd. For $C_{41}H_{44}O_7$ [M+Na]$^+$: 671.2985, found: 671.2970.

4-Methoxyphenyl 2,3,4-tri-O-allyl-α-D-galactopyranoside (Compound 4)

A solution of compound 3 (300 mg, 0.46 mmol) in 80% aqueous AcOH (5 mL) was stirred at 80° C. for 1.5 h. The reaction mixture was concentrated before purification by flash chromatography (1:6 EtOAc-hexanes) giving compound 4 (147 mg, 78%.) $^1$H NMR (400 MHz, $CDCl_3$): δ 7.02-6.78 (m, 4H, $MeOC_6H_4$); 5.95-5.89 (m, 3H, $CH_2$—CH=$CH_2$); 5.50 (d, 1H, J=3.5 Hz, H-1); 5.35-5.12 (m, 6H, $CH_2$—CH=$CH_2$); 4.42 (dd, 1H, $J_1$=3.2 Hz, $J_2$=9.3 Hz, H-3); 4.27-3.89 (m, 10H, $CH_2$—CH=$CH_2$, H-2, H-4, H-5, OH); 3.81 (m, 1H, H-6a); 3.74 (s, 3H, $OCH_3$); 3.70 (m, 1H, H-6b.) $^{13}$C NMR (100 MHz, $CDCl_3$): δ 155.1, 150.9 (Ar); 135.0, 134.9 ($CH_2$—CH=$CH_2$); 118.6, 118.0, 117.4, 116.6, 114.5 ($CH_2$—CH=$CH_2$, Ar); 97.5 (C-1); 78.2, 75.9, 74.0, 72.6, 72.0, 71.0 ($CH_2$—CH=$CH_2$, C-2, C-3, C-4, C-5); 62.7 (C-6); 55.6 ($OCH_3$.) HRMS (ESI): Calcd. For $C_{22}H_{30}O_7$ [M+Na]$^+$: 429.1890, found: 429.1891.

4-Methoxyphenyl 2,3,4-tri-O-allyl-6-O-methyl-phosphramidate-α-D-galactopyranoside (Compound 5)

To a solution of compound 4 (65 mg, 0.16 mmol) and methyl dichlorophosphate (150 μL, 1.3 mmol) dissolved in $CH_2Cl_2$ (3 mL) with molecular sieves, $Et_3N$ (175 μL, 1.3 mmol) was added drop-wise. The reaction mixture was stirred at room temperature for 5 hours. Upon completion of the reaction as judged by TLC, ammonia gas was injected into the reaction mixture through a needle. After 10 min, the reaction mixture was filtered and concentrated. Purification with column chromatography (1:1 EtOAc-hexanes) yielded compound 5 (15 mg, 19%.) $^1$H NMR (400 MHz, $CDCl_3$): δ 7.04-6.77 (m, 4H, $MeOC_6H_4$); 5.99-5.85 (m, 3H, $CH_2$—CH=$CH_2$); 5.48 (2d, 1H, J=3.6 Hz, H-1); 5.36-5.10 (m, 6H, $CH_2$—CH=$CH_2$); 4.41 (m, 1H, H-3); 4.29-4.10 (m, 8H, $CH_2$—CH=$CH_2$, H-2, H-4); 3.95-3.86 (m, 3H, H-5, H-6); 3.73 (s, 3H, $OCH_3$); 3.57 (2d, 3H, J=11.4 Hz, $OCH_3$); 2.75, 2.56 (2d, 2H, $NH_2$.) $^{13}$C NMR. (100 MHz, $CDCl_3$): δ 155.2, 155.0, 150.9 (Ar); 135.0, 134.9 ($CH_2$—CH=$CH_2$); 128.9, 128.3, 118.8, 118.5, 117.7, 117.5, 117.4, 116.6, 114.5, 114.4 ($CH_2$—CH=$CH_2$, Ar); 97.6, 97.2 (C-1); 78.1, 75.8, 74.4, 74.0, 72.7, 71.9, 70.5, 70.4, 70.0, 69.9, 68.5, 65.5, ($CH_2$—CH=$CH_2$, C-2, C-3, C-4, C-5, C-6); 55.7, 53.3, 53.2 ($OCH_3$.) HRMS (ESI): Calcd. For $C_{23}H_{34}NO_9P$ [M+H]$^+$: 500.2050, found: 500.2035.

4-Methoxyphenyl 6-O-methyl-phosphoramidate-α-D-galactopyranoside (Compound 6)

To a solution of compound 5 (17.0 mg) dissolved in MeOH (1 mL), $PdCl_2$ (5.0 mg) was added and the reaction mixture was stirred at room temperature for 3 h. The reaction mixture was then filtered and concentrated. Purification with column chromatography (pure EtOAc) yielded compound 6 (5.1 mg, 39%.) $^1$H NMR (400 MHz, $D_2O$): δ 6.98-6.80 (m, 4H, $MeOC_6H_4$); 5.39 (2d, 1H, J=3.6 Hz, H-1); 4.13 (m, 1H, H-3); 4.01-3.85 (m, 4H, H-4, H-5, H-6); 3.78 (m, 1H, H-2); 3.63 ($OCH_3$); 3.41 (2d, 3H, J=11.4 Hz, $OCH_3$.) $^{13}$C NMR (100 MHz, $D_2O$): δ 154.6, 150.0, 149.9, 119.3, 119.1, 114.9 (Ar); 98.1, 97.9 (C-1); 70.3, 70.2, 70.0, 69.1, 68.8, 67.8, 65.8 (C-2, C-3, C-4, C-5, C-6); 55.6 ($OCH_3$); 53.6, 53.5, 53.4 ($OCH_3$.) HRMS (ESI): Calcd. For $C14H23NO9P$ [M+H]$^+$ cal. 380.1111; found 380.1110.

2,3,4-Tri-O-allyl-6-O-trityl-α,β-D-galactopyranosyl trichloroacetimidate (Compound 7)

To a solution of compound 3 (5.0 g, 7.7 mmol) dissolved in $CH_3CN$ (480 mL) and $H_2O$ (120 mL), cerium ammonium nitrate (12.8 g, 23 mmol) was added and the reaction mixture was stirred for 20 min at 0° C. The mixture was then diluted with brine (200 mL) and extracted with EtOAc (3×300 mL.) The organic layer was washed with saturated aq. $Na_2CO_3$ and water, dried over $Na_2SO_4$, concentrated and purified with column chromatography (1:6 EtOAc-hexanes.) The resulting hemiacetal (3.3 g, 6.1 mmol) was dissolved in anhydrous $CH_2Cl_2$ (120 ml) and $CCl_3CN$ (310 μL, 30 mmol) and $K_2CO_3$ (420 mg, 30 mmol) were added. The reaction mixture was stirred at room temperature overnight before it was filtered through Celite® and concentrated. Purification with flash chromatography (1:4 EtOAc-hexanes with 1% $Et_3N$ by volume) gave compound 7 as an α,β-mixture (3.6 g, 57% over 2 steps) (compounds 7A and 7B.)

7A: $^1$H NMR (400 MHz, $CDCl_3$): δ 8.52 (s, 1H, NH); 7.42-7.18 (m, 15H, Ar—H); 6.46 (d, 1H, J=3.6 Hz, H-1); 6.00-5.61 (m, 3H, $CH_2$—CH=$CH_2$); 5.39-4.98 (m, 6H, $CH_2$—CH=$CH_2$); 4.32-3.84 (m, 10H, $CH_2$—CH=$CH_2$, H-2, H-3, H-4, H-5); 3.35 (m, 1H, H-6a); 3.09 (m, 1H, H-6b); $^{13}$C NMR (100 MHz, $CDCl_3$): δ 161.3, 160.8, 143.9, 143.7, 135.2, 135.0, 134.9, 134.8, 134.1, 133.8, 128.8, 128.6, 127.8, 127.1, 127.0 (Ar, $CH_2$—CH=$CH_2$); 117.9, 117.4, 117.3, 116.7, 116.5 ($CH_2$—CH=$CH_2$); 104.0 (C-1); 86.8 (C-3); 86.7 (C-2); 83.8 (C-3); 82.6; 76.7 (C-4); 75.3, 74.1, 72.5, 72.2, 71.8, 71.0 ($CH_2$—CH=$CH_2$, C-5); 61.9 (C-6.) HRMS (ESI): Calcd. For $C_{36}H_{38}Cl_3NO_6$ [M+Na]$^+$: 708.1663, found: 708.1673.

7B: $^1$H NMR (400 MHz, $CDCl_3$): δ 8.59 (s, 1H, NH); 7.41-7.18 (m, 15H, Ar—H); 5.90 (m, 2H, $CH_2$—CH=$CH_2$); 5.62 (m, 2H, H-1, $CH_2$—CH=$CH_2$); 5.35-5.01 (m, 6H, $CH_2$—CH=$CH_2$); 4.31-3.83 (m, 6H $CH_2$—

CH=CH$_2$); 3.83 (m, 1H, H-5); 3.76 (dd, 1H, J$_1$=8.2 Hz, J$_2$=9.7 Hz, H-3); 3.62 (t, 1H, J=5.9 Hz, H-2); 3.48-3.39 (m, 2H, H-4, H-6a); 3.12 (dd, 1H, J$_1$=7.2 Hz, J$_2$=9.3 Hz, H-6b.) $^{13}$C NMR (100 MHz, CDCl$_3$): δ 161.5, 143.8 (Ar); 135.4, 134.9, 134.8 (CH$_2$—CH=CH$_2$); 128.7, 128.6, 128.0, 127.9, 127.1 (Ar); 117.3, 117.0, 116.8 (CH$_2$—CH=CH$_2$); 98.5 (C-1); 86.8 (C-2); 81.6 (C-3); 77.8 (C-5); 74.6 (C-3) 74.2, 73.8, 73.3, 72.0 (CH$_2$—CH=CH$_2$, C4); 62.4 (C-6.) HRMS (ESI): Calcd. For C$_{36}$H$_{38}$Cl$_3$NO$_6$ [M+Na]$^+$; 708.1663, found: 708.1673.

5-Amino-N-phthalimido-pentanyl2,3,4-tri-O-allyl-6-O-trityl-β-D-galactopyranoside (Compound 8)

Trichloroacetimidate (compound 7, both anomers) (1.1 g, 1.6 mmol) and 5-amino-N-phthalimido-pentanol (560 mg, 2.4 mmol) were dissolved in anhydrous CH$_2$Cl$_2$ (25 mL) and the reaction mixture was cooled to 0° C. TMSOTf (15 μL, 0.080 mmol) was added drop-wise and the reaction mixture was stirred for 15 min at 0° C. The reaction was then neutralized with Et$_3$N (15 μL) and concentrated. Purification with flash chromatography (1:8 EtOAc-hexanes) gave compound 8 (783 mg, 65%.) $^1$H NMR (400 MHz, CDCl$_3$): δ 7.80-7.67 (m, 4H, phthalimido protons); 7.41-7.19 (m, 15H, Ar—H); 5.98-5.59 (m, 3H, CH$_2$—CH=CH$_2$); 5.33-4.94 (m, 6H, CH$_2$—CH=CH$_2$); 4.30-3.84 (m, 8H, CH$_2$—CH=CH$_2$, H-1, linker-CHH); 3.77 (d, 1H, J=2.9 Hz, H-5); 3.62 (t, 2H, J=7.3 Hz, linker-CH$_2$); 3.45-3.35 (m, 4H, H-2, H-4, H-6a, linker-CHH); 3.29 (dd, 1H, J$_1$=3.0 Hz, J$_2$=9.8 Hz, H-3); 3.13 (dd, 1H, J$_1$=9.4 Hz, J$_2$=10.1 Hz, H-6b); 1.65 (m, 4H, linker-CH$_2$); 1.40 (m, 2H, linker-CH$_2$.) $^{13}$C NMR (100 MHz, CDCl$_3$): 168.4, 143.8 (Ar); 135.7, 135.3, 135.2 (CH$_2$—CH=CH$_2$); 133.9, 132.1, 128.7, 127.9, 127.1, 123.2 (Ar); 116.8, 116.5 (CH$_2$—CH=CH$_2$); 103.7 (C-1); 86.8; 81.5 (C-1); 79.2 (C-2); 73.9, 73.6, 73.4, 73.3 (C-5, C-4, CH$_2$—CH=CH$_2$); 71.9, 69.4 (linker); 62.5 (C-6); 37.9, 29.2, 28.4, 23.4 (linker.) HRMS (ESI): Calcd. For C$_{47}$H$_{51}$NO$_8$ [M+Na]$^+$: 780.3513, found 780.3489.

5-Amino-N-phthalimido-pentanyl 2,3,4-tri-O-allyl-β-D-galactopyranoside (Compound 9)

A solution of compound 8 (493 mg, 0.65 mmol) dissolved in 80% aqueous AcOH (10 mL) was stirred at 80° C. for 1 h. The reaction mixture was concentrated before purification by flash chromatography (1:1 EtOAc-hexanes) giving compound 9 (260 mg, 78%.) $^1$H NMR (400 MHz, CDCl$_3$): δ 7.81-7.66 (m, 4H, phthalimido protons); 5.92-5.82 (m, 3H, CH$_2$—CH=CH$_2$); 5.30-5.10 (m, 6H, CH$_2$—CH=CH$_2$); 4.37-4.02 (m, 6H, CH$_2$—CH=CH$_2$); 4.22 (d, 1H, J=7.7 Hz, H-1); 3.88 (m, 2H, H-6a, linker-CHH); 3.69-3.60 (m, 4H, H-4, H-6b, linker-CH$_2$); 3.51-3.42 (m, 2H, H-2, linker-CHH); 3.39 (m, 1H, H-5); 3.28 (dd, 1H, J$_1$=3.0 Hz, J$_2$=9.8 Hz, H-3); 2.09 (m, 1H, 6-OH); 1.65 (m, linker-CH$_2$); 1.40 (m, 2H, linker-CH$_2$.) $^{13}$C NMR (100 MHz, CDCl$_3$): δ 168.5 (phthalimido C=O); 135.3, 135.0, 133.9 (CH$_2$—CH=CH$_2$); 132.1, 123.2 (phthalimido); 117.8, 116.7, 116.6 (CH$_2$—CH=CH$_2$); 103.9 (C-1); 81.6 (C-3); 79.1 (C-2); 74.6 (C-5) 74.0 (C-4); 73.7, 73.6 (CH$_2$—CH=CH$_2$); 72.1, 69.6 (linker); 62.5 (C-6); 37.8, 29.2, 28.3, 23.3 (linker.) HRMS (ESI): Calcd. For C$_{28}$H$_{37}$NO$_8$ [M+Na]$^+$: 538.2417, found 538.2403.

5-Amino-N-phthalimido-pentanyl2,3,4-tri-O-allyl-6-O-methylphosphoramidate-β-D-galactopyranoside (Compound 10)

To a solution of compound 9 (400 mg, 0.78 mmol) and methyl dichlorophosphate (0.70 mL, 6.0 mmol) dissolved in CH$_2$Cl$_2$ (15 mL) with molecular sieves, Et$_3$N (0.70 mL, 5.0 mmol) was added drop-wise. The reaction mixture was stirred at room temperature for 12 hours. Upon completion of the reaction as judged by TLC, ammonia gas was injected into the reaction mixture through a needle, After 10 min, the reaction mixture was filtered and concentrated. Purification with column chromatography (9:1 EtOAc-MeOH) yielded compound 10 (129 mg, 27%.) $^1$H NMR (400 MHz, CDCl$_3$): 7.80-7.68 (phthalimido protons); 5.88 (m, 3H, CH$_2$—CH=CH$_2$); 5.30-5.10 (m, 6H, CH$_2$—CH=CH$_2$); 4.23-4.10 (m, 9H, CH$_2$—CH=CH$_2$, H-1, linker-CH$_2$); 3.82 (m, 1H, H-5); 3.71-3.39 (m, 9H, OCH$_3$, H-4, H-2, H-6a, H-6b, linker-CH$_2$); 3.28 (m, 1H, H-3); 2.87 (dd, 2H, J$_1$=5.3 Hz J$_2$=13.0 Hz, NH$_2$); 1.66 (m, 4H, linker-CH$_2$); 1.38 (m, 2H, linker-CH$_2$.) $^{13}$C NMR (100 MHz, CDCl$_3$): δ 168.5 (Ar); 135.4, 135.2, 134.9 (CH$_2$—CH=CH$_2$); 133.9, 132.1, 123.2 (Ar); 117.5, 117.2, 116.8, 116.7, 116.6 (CH$_2$—CH=CH$_2$); 103.8 (C-1); 81.4 (C-3); 78.9 (C-2); 74.0, 73.8, 73.3, 73.2, 73.0, 72.9, 72.1 (CH$_2$—CH=CH$_2$, C-5, C-4); 69.8, 69.7 (C-6) 65.3; 65.0, 64.9 (linker) 53.4, 53.3 (OCH$_3$); 37.9, 29.7, 29.2, 28.3 (linker.) HRMS (ESI): Calcd. For C$_{29}$H$_{41}$N$_2$O$_{10}$P [M+H]$^+$: 609.2578, found 609.2585.

5-Amino-N-phthalimido-pentanyl6-O-methylphosphramidate-β-D-galactopyranoside (Compound 11)

To a solution of compound 10 (95 mg, 0.16 μmol) dissolved in MeOH (4 mL), PdCl$_2$ (20 mg) was added and the reaction mixture was stirred at room temperature for 4 h. The reaction mixture was then filtered and concentrated. Purification with column chromatography (9:1 EtOAc-MeOH) gave compound 11 (57 mg, 75%.) $^1$H NMR (400 MHz, D$_2$O): δ 7.64 (m, 4H, phthalimido protons); 4.23 (d, 1H, J=8.0 Hz, H-1); 4.01 (m, 2H, H-6); 3.78-3.70 (m, 3H, H-4, H-5, linker-CHH)); 3.59-3.45 (m, 7H, OCH$_3$, linker-CH$_2$ linker-CHH, H-3); 3.33 (dd, 1H, J$_1$=8.0 Hz, J$_2$=9.8 Hz, H-2); 1.51 (m, 4H, linker-CH$_2$); 1.22 (m, 2H, linker-CH$_2$.) $^{13}$C NMR (100 MHz, D$_2$O): 170.9, 134.5, 133.9, 131.3, 126.0, 123.1 (Ar); 102.6 (C-1); 73.2 (C-5); 72.5 (C-3); 71.9 (C-2); 70.3, 70.2 (linker); 68.1 (C-4); 65.4 (C-6); 53.6 (OCH$_3$); 48.7; 37.6 (linker); 28.2; 27.2, 22.3 (linker.) HRMS (ESI): Calcd. For C$_{20}$H$_{29}$N$_2$O$_{10}$P [M+H]$^+$: 489.1639, found 489.1624.

5-Amino-pentanyl 6-O-methylphosphramidate-β-D-galactopyranoside (Compound 12)

To a solution of compound 11 (23 mg, 0.047 μmol) dissolved in 95% EtOH (1 mL), hydrazine monohydrate (16 μL, 0.33 μmol) was added and the reaction mixture was stirred at room temperature overnight. The reaction mixture was then concentrated and purification with column chromatography (3:1 EtOAc-MeOH) gave compound 12 (14 mg, 82%.) $^1$H NMR (400 MHz, D$_2$O): δ 4.27 (d, 1H, J=7.1 Hz, H-1); 4.03 (m, 2H, linker-CH$_2$); 3.81-3.75 (m, 3H, H-4, H-5, H-6a); 3.61-3.48 (m, 5H, OCH$_3$, H-3, H-6b); 3.36 (dd, 1H, J$_1$=7.9, J$_2$=9.9 Hz, H-2); 2.82 (t, 2H, J=7.5 Hz, linker-CH$_2$); 1.52 (m, 4H, linker-CH$_2$); 1.30 (m, 2H, linker-CH$_2$.) $^{13}$C NMR (100 MHz, D$_2$O): 102.6 (C-1); 73.2 (C-5); 72.5 (C-3); 70.5 (C-2); 70.1 (C-6); 68.1 (C-4); 60.0 (linker); 48.7 (OCH$_3$); 39.2, 28.0, 26.3, 22.0, 21.9 (linker.) HRMS (ESI): Calcd. For C$_{12}$H$_{27}$N$_2$O$_8$P [M+H]$^+$: 359.1584, found 359.1587.

Figure 4:
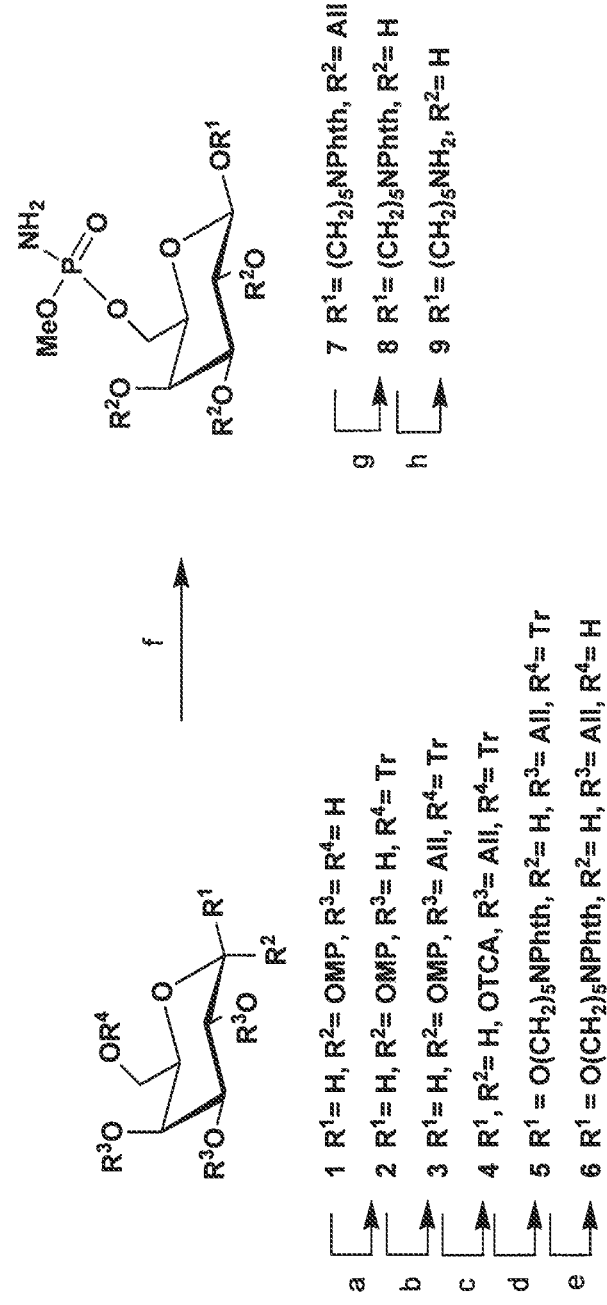
FIG. 4 depicts another scheme for the synthesis of the aminopentyl glycoside of the MeOPN→6-Gal construct (O-Me-phosphoramidate galactoside), MeOPN→6-β-D-Galp-(1→O(CH₂)₅NH₂ ("Scheme 2a".) The reagents and conditions employed in the steps indicated therein are as follows: (a) TrCl, pyridine, 95%; (b) AllBr, NaH, DMF, 0° C., 89%; (c) CAN, $CH_3CN$, $H_2O$, 0° C.; then $CCl_3CN$, $K_2CO_3$, $CH_2Cl_2$, 57% over 2 steps; (d) HO(CH₂)₅NPhth, TMSOTf, $CH_2Cl_2$, 65%; (e) 80% AcOH, 80° C., 78%; (f) $PCl_2O_2Me_2$, $Et_3N$, $CH_2Cl_2$, then $NH_3$ (g), 27%; (g) $PdCl_2$, MeOH, 75%, (h) $H_2NNH_2$, EtOH, 82%. CAN, cerium ammonium nitrate; TMSOTf, trimethylsilyl trifluoromethanesulfonate; Tr, trityl; All, allyl; OMP, 4-methoxyphenyl group; OTCA, trichloroacetimidate.

The synthesis of the structure MeOPN→6-β-D-Galp-(1→O(CH$_2$)$_5$NH$_2$ can also be depicted as set forth in FIG. 4, Scheme 2a, and is summarized below:

Starting from a previously reported compound (Comfort, et al., Biochem, 46: 3319-3330 (2007)), 4-methoxyphenyl-α-D-galactopyranoside (see Scheme 2a, compound 1), trityl group was selectively introduced to C-6. Originally, benzoylation was performed on compound 2 (Scheme 2a, compound 2), however, extensive migration observed during the introduction of MeOPN lead to the elucidation of a more suitable protecting group. Therefore, allyl groups were selected to protect the C-2, C-3 and C-4 positions which were resistant to migration. Allyl groups were later deprotected with catalytic hydrogenolysis which proved to be compatible with the MeOPN modification.

After allyl groups were installed, an amino-pentanyl linker was introduced to the anomeric position as a site for conjugation. Starting from galactoside (Scheme 2a, compound 3), 4-methoxyphenyl group (OMP) was first removed with cerium ammonium nitrate (CAN.) The corresponding hemiacetal was then converted into trichloroacetimidate donor (see Scheme 2a, compound 4.) 5-Amino-N-phthalimido-pentanyl linker was then introduced with TMSOTf as activator at 0° C. Compound 5 was collected with 65% as the β anomer and 29% as the α anomer. The removal of trityl group gave compound 6 with a free 6-hydroxyl group for modification.

The strategy for the introduction of MeOPN group is similar to a reaction proposed by C. Mara et al, Bioorg. Med. Chem. Lett. 6180-6183 (2011.) Compound 6 was treated with commercially available methyl dichlorophosphate in the presence of triethyl amine, followed by ammonolysis. Due to the chirality nature of the newly introduced MeOPN (R and S), compound 7 was collected as a mixture of two diastereoisomers. $^1$H NMR was able to confirm that compound 7 was indeed a 1:1 mixture of two diastereoisomers, revealing two sets of signals throughout the spectrum, such can be seen for anomeric and O-Me signals. The reaction yielded a mixture of side products, the most abundant being the O-Me group being replaced by a second $NH_2$, accounting for the poor yield of this reaction.

Allyl and phthalimido protecting groups were removed with palladium (II) chloride and hydrazine respectively, generating compound 8 and compound 9. Similar to compound 7, a mixture of diastereoisomers is apparent in NMR. Although not optically pure, the $^{31}$P NMR result agrees with native MeOPN-containing polysaccharides, having a phosphorus signals around 14 ppm. $^{31}$H-$^{31}$P HMBC NMR experiment was able to confirm that the MeOPN was introduced to the O-6 position, showing correlation signal with O-Me as well as the H-6 signals (data not shown.)

The details of the above synthesis of MeOPN→6-β-D-Galp-(1→$OCH_2$)$_5NH_2$ is provided below and in Scheme 2a:

4-Methoxyphenyl 6-O-trityl-α-D-galactopyranoside (Scheme 2a, Compound 2)

To a solution of compound 1 (2.7 g, 9.3 mmol) dissolved in pyridine (40 mL), trityl chloride (3.1 g, 11 mmol) was added and the reaction mixture was stirred at 60° C. for 3 days. The reaction mixture was then concentrated and purified with flash chromatography (1:1 EtOAc-hexanes) to yield compound 2 (4.7 g, 95%.) $[α]_D^{25}$=+91.2° (c=0.21, $CHCl_3$); $^1$H NMR (400 MHz, $CDCl_3$): δ 7.44-7.20 (m, 15H, Ar—H); 7.11-6.83 (m, 4H, $MeOC_6H_4$); 5.51 (d, 1H, J=3.6 Hz, H-1); 4.05-3.93 (m, 4H, H-2, H-3, H-4, H-5); 3.79 (s, 3H, $OCH_3$); 3.54-3.32 (m, 2H, H-6.) $^{13}$C NMR (100 MHz, $CDCl_3$): δ 155.3, 151.2, 150.6, 144.3, 143.8, 143.7, 143.6, 129.1, 128.6, 128.0, 127.9, 127.8, 127.5, 127.3, 127.1, 127.0, 118.5, 117.9, 114.6, 114.5, 114.4 (Ar); 98.4 (C-1); 87.0, 71.2, 70.0, 69.3 (C-2, C-3, C-4, C-5); 63.6 (C-6); 55.6 ($CH_3$.) HRMS (ESI): Calcd. For $C_{32}H_{32}O_7$ $[M+Na]^+$: 551.2046, found: 551.2021.

4-Methoxyphenyl 2,3,4-tri-O-allyl-6-O-trityl-α-D-galactopyranoside (Scheme 2a, Compound 3)

A solution of compound 2 (4.7 g, 8.8 mmol) dissolved in DMF (60 mL) with allyl bromide (4.6 mL, 53 mmol) was cooled to 0° C. Sodium hydride, 60% dispersion in mineral oil (1.2 g, 29 mmol) was added and the reaction mixture was stirred for 1 h at 0° C. The reaction was then quenched with MeOH (10 mL), poured into ice-cold water (100 mL) and extracted with EtOAc (3×100 mL) The organic layer was dried over $Na_2SO_4$ and concentrated. Purification by flash chromatography eluting with 1:7 EtOAc-hexanes gave compound 3 (see scheme 1, structure 3) (5.1 g, 89%) $^1$H NMR (400 MHz, $CDCl_3$): δ 7.38-7.18 (m, 15H, Ar—H); 7.10-6.75 (m, 4H, $MeOC_6H_4$); 6.00-5.53 (m, 3H, $CH_2$—CH=$CH_2$); 5.42 (d, 1H, J=3.2 Hz, H-1); 5.33-4.98 (m, 6H, $CH_2$—CH=$CH_2$); 4.37-3.72 (m, 13H, $CH_2$—CH=$CH_2$, H-2, H-3, H-4, H-5, $OCR_3$); 3.38 (m, 1H, H-6a); 3.01 (m, 1H, H-6b.) $^{13}$C NMR (100 MHz, $CDCl_3$): δ 155.0, 151.0, 143.9 (Ar); 135.2, 135.1, 135.0 ($CH_2$—CH=$CH_2$); 128.6, 127.8, 127.0, 119.0, 117.4, 117.3, 116.4, 114.4 ($CH_2$—CH=$CH_2$, Ar); 97.5 (C-1); 86.8; 78.2 (C-2); 77.4 (C-4); 76.1 (C-5); 73.9, 72.5, 71.9 ($CH_2$—CH=$CH_2$); 70.4 (C-3) 63.3 (C-6); 55.6 ($OCR_3$.) HRMS (ESI): Calcd. For $C_{41}H_{44}O_7$ $[M+Na]^+$: 671.2985, found: 671.2970.

2,3,4-Tri-O-allyl-6-O-trityl-α,β-D-galactopyranosyl trichloroacetimidate (Scheme 2a, Compound 4)

To a solution of compound 3 (5.0 g, 7.7 mmol) dissolved in $CH_3CN$ (480 mL) and $H_2O$ (120 mL), cerium ammonium nitrate (12.8 g, 23 mmol) was added and the reaction mixture was stirred for 20 min at 0° C. The mixture was then diluted with brine (200 mL) and extracted with EtOAc (3×300 mL.) The organic layer was washed with saturated aq. $Na_2CO_3$ and water, dried over $Na_2SO_4$, concentrated and purified with column chromatography (1:6 EtOAc-hexanes.) The resulting hemiacetal (3.3 g, 6.1 mmol) was dissolved in anhydrous $CH_2Cl_2$ (120 ml) and $CCl_3CN$ (310 µL, 30 mmol) and $K_2CO_3$ (420 mg, 30 mmol) were added. The reaction mixture was stirred at room temperature overnight before it was filtered through Celate® and concentrated. Purification with flash Chromatography (1:4 EtOAc-hexanes with 1% $Et_3N$ by volume) gave compound 4 as an α,β-mixture (3.6 g, 57% over 2 steps.)

5-Amino-N-phthalimido-pentanyl 2,3,4-tri-O-allyl-6-O-trityl-β-D-galactopyranoside (Scheme 2a, Compound 5)

Trichloroacetimidate (compound 4) (1.1 g, 1.6 mmol) and 5-amino-N-phthalimido-pentanol (560 mg, 2.4 mmol) were dissolved in anhydrous $CH_2Cl_2$ (25 mL) and the reaction mixture was cooled to 0° C. TMSOTf (15 µL, 0.080 mmol) was added drop-wise and the reaction mixture was stirred for 15 min at 0° C. The reaction was then neutralized with $Et_3N$ (15 µL) and concentrated. Purification with flash chromatography (1:8 EtOAc-hexanes) gave compound 5 (783 mg, 65%.) $^1$H NMR (400 MHz, $CDCl_3$): δ 7.80-7.67 (m, 4H, phthalimido protons); 7.41-7.19 (m, 15H, Ar—H); 5.98-5.59 (m, 3H, $CH_2$—CH=$CH_2$); 5.33-4.94 (m, 6H, $CH_2$—CH=$CH_2$); 4.30-3.84 (m, 8H, $CH_2$—CH=$CH_2$, H-1, linker-CHH); 3.77 (d, 1H, J=2.9 Hz, H-5); 3.62 (t, 2H, J=7.3 Hz, linker-CH$_2$); 3.45-3.35 (m, 4H, H-2, H-4, H-6a, linker-CHH); 3.29 (dd, 1H, J$_1$=3.0 Hz, J$_2$=9.8 Hz, H-3); 3.13 (dd, 1H, J$_1$=9.4 Hz, J$_2$=10.1 Hz, H-6b); 1.65 (m, 4H, linker-CH$_2$); 1.40 (m, 2H, linker-CH$_2$.) $^{13}$C NMR (100 MHz, CDCl$_3$): 168.4, 143.8 (Ar); 135.7, 135.3, 135.2 (CH$_2$—CH=CH$_2$); 133.9, 132.1, 128.7, 127.9, 127.1, 123.2 (Ar); 116.8, 116.5 (CH$_2$—CH=CH$_2$); 103.7 (C-1); 86.8; 81.5 (C-1); 79.2 (C-2); 73.9, 73.6, 73.4, 73.3 (C-5, C-4, CH$_2$—CH=CH$_2$); 71.9, 69.4 (linker); 62.5 (C-6); 37.9, 29.2, 28.4, 23.4 (linker.) HRMS (ESI): Calcd. For C$_{47}$H$_{51}$NO$_8$ [M+Na]$^+$: 780.3513, found 780.3489.

5-Amino-N-phthalimido-pentanyl 2,3,4-tri-O-allyl-
β-D-galactopyranoside (Scheme 2a, Compound 6)

A solution of compound 5 (493 mg, 0.65 mmol) dissolved in 80% aqueous AcOH (10 mL) was stirred at 80° C. for 1 h. The reaction mixture was concentrated before purification by flash chromatography (1:1 EtOAc-hexanes) giving compound 6 (260 mg, 78%.) $^1$H NMR (400 MHz, CDCl$_3$): δ 7.81-7.66 (m, 4H, phthalimido protons); 5.92-5.82 (m, 3H, CH$_2$—CH=CH$_2$); 5.30-5.10 (m, 6H, CH$_2$—CH=CH$_2$); 4.37-4.02 (m, 6H, CH$_2$—CH=CH$_2$); 4.22 (d, 1H, J=7.7 Hz, H-1); 3.88 (m, 2H, H-6a, linker-CHH); 3.69-3.60 (m, 4H, H-4, H-6b, linker-CH$_2$); 3.51-3.42 (m, 2H, H-2, linker-CHH); 3.39 (m, 1H, H-5); 3.28 (dd, 1H, J$_1$=3.0 Hz, J$_2$=9.8 Hz, H-3); 2.09 (m, 1H, 6-OH); 1.65 (m, 4H, linker-CH$_2$); 1.40 (m, 2H, linker-CH$_2$.) $^{13}$C NMR (100 MHz, CDCl$_3$): δ 168.5 (phthalimido C=O); 135.3, 135.0, 133.9 (CH$_2$—CH=CH$_2$); 132.1, 123.2 (Phthalimido); 117.8, 116.7, 116.6 (CH$_2$—CH=CH$_2$); 103.9 (C-1); 81.6 (C-3); 79.1 (C-2); 74.6 (C-5) 74.0 (C-4); 73.7, 73.6 (CH$_2$—CH=CH$_2$); 72.1, 69.6 (linker); 62.5 (C-6); 37.8, 29.2, 28.3, 23.3 (linker.) HRMS (ESI): Calcd. For C$_{28}$H$_{37}$NO$_8$ [M+Na]$^+$: 538.2417, found 538.2403.

5-Amino-N-phthalimido-pentanyl2,3,4-tri-O-allyl-6-
O-methylphosphoramidate-β-D-galactopyranoside
(Scheme 2a, Compound 7)

To a solution of compound 6 (400 mg, 0.78 mmol) and methyl dichlorophosphate (0.70 mL, 6.0 mmol) dissolved in CH$_2$Cl$_2$ (15 mL) with molecular sieves, Et$_3$N (0.70 mL, 5.0 mmol) was added drop-wise. The reaction mixture was stirred at room temperature for 12 hours. Upon completion of the reaction as judged by TLC, ammonia gas was injected into the reaction mixture through a needle. After 10 min, the reaction mixture was filtered and concentrated. Purification with column chromatography (9:1 EtOAc-MeOH) yielded product 7 (129 mg, 27%.) $^1$H NMR (400 MHz, CDCl$_3$): 7.80-7.68 (phthalimido protons); 5.88 (m, 3H, CH$_2$—CH=CH$_2$); 5.30-5.10 (m, 6H, CH$_2$—CH=CH$_2$); 4.23-4.10 (m, 9H, CH$_2$—CH=CH$_2$, H-1, linker-CH$_2$); 3.82 (m, 1H, H-5); 3.71-3.39 (m, 9H, OCH$_3$, H-4, H-2, H-6a, H-6b, linker-CH$_2$); 3.28 (m, 1H, H-3); 2.87 (dd, 2H, J$_1$=5.3 Hz J$_2$=13.0 Hz, NH$_2$); 1.66 (m, 4H, linker-CH$_2$); 1.38 (m, 2H, linker-CH$_2$.) $^{13}$C NMR (100 MHz, CDCl$_3$): δ 168.5 (Ar); 135.4, 135.2, 134.9 (CH$_2$—CH=CH$_2$); 133.9, 132.1, 123.2 (Ar); 117.5, 117.2, 116.8, 116.7, 116.6 (CH$_2$—CH=CH$_2$); 103.8 (C-1); 81.4 (C-3); 78.9 (C-2); 74.0, 73.8, 73.3, 73.2, 73.0, 72.9, 72.1 (CH$_2$—CH=CH$_2$, C-5, C-4); 69.8, 69.7 (C-6) 65.3; 65.0, 64.9 (linker) 53.4, 53.3 (OCH$_3$); 37.9, 29.7, 29.2, 28.3 (linker.) HRMS (ESI): Calcd. For C$_{29}$H$_{41}$N$_2$O$_{10}$P [M+H]$^+$: 609.2578, found 609.2585.

5-Amino-N-phthalimido-pentanyl6-O-methylphos-
phoramidate-β-D-galactopyranoside (Scheme 2a,
Compound 8)

To a solution of compound 7 (95 mg, 0.16 µmol) dissolved in MeOH (4 mL), PdCl$_2$ (20 mg) was added and the reaction mixture was stirred at room temperature for 4 h. The reaction mixture was then filtered and concentrated. Purification with column chromatography (9:1 EtOAc-MeOH) gave compound 8 (57 mg, 75%.) $^1$H NMR (400 MHz, D$_2$O): δ 7.64 (m, 4H, phthalimido protons); 4.23 (d, 1H, J=8.0 Hz, H-1); 4.01 (m, 2H, H-6); 3.78-3.70 (m, 3H, H-4, H-5, linker-CHH)); 3.59-3.45 (m, 7H, OCH$_3$, linker-CH$_2$ linker-CHH, H-3); 3.33 (dd, 1H, J$_1$=8.0 Hz, J$_2$=9.8 Hz, H-2); 1.51 (m, 4H, linker-CH$_2$); 1.22 (m, 2H, linker-CH$_2$. $^{13}$C NMR (100 MHz, D$_2$O): 170.9, 134.5, 133.9, 131.3, 126.0, 123.1 (Ar); 102.6 (C-1); 73.2 (C-5); 72.5 (C-3); 71.9 (C-2); 70.3, 70.2 (linker); 68.1 (C-4); 65.4 (C-6); 53.6 (OCH$_3$); 48.7; 37.6 (linker); 28.2; 27.2, 22.3 (linker.) HRMS (ESI): Calcd. For C$_{20}$H$_{29}$N$_2$O$_{10}$P [M+H]$^+$: 489.1639, found 489.1624.

5-Amino-pentanyl 6-O-methylphosphoramidate-β-
D-galactopyranoside (Scheme 2a, Compound 9)

To a solution of compound 8 (23 mg, 0.047 µmol) dissolved in 95% EtOH (1 mL), hydrazine monohydrate (16 µL, 0.33 µmol) was added and the reaction mixture was stirred at room temperature overnight. The reaction mixture was then concentrated and purification with column chromatography (3:1 EtOAc-MeOH) gave compound 9 (14 mg, 82%.) $^1$H NMR (400 MHz, D$_2$O): δ 4.27 (d, 1H, J=7.1 Hz, H-1); 4.03 (m, 2H, linker-CH$_2$); 3.81-3.75 (m, 3H, H-4, H-5, H-6a); 3.61-3.48 (m, 5H, OCH$_3$, H-3, H-6b); 3.36 (dd, 1H, J$_1$=7.9, J$_2$=9.9 Hz, H-2); 2.82 (t, 2H, J=7.5 Hz, linker-CH$_2$); 1.52 (m, 4H, linker-CH$_2$); 1.30 (m, 2H, linker-CH$_2$.) $^{13}$C NMR (100 MHz, D$_2$O): δ 102.6 (C-1); 73.2 (C-5); 72.5 (C-3); 70.5 (C-2); 70.1 (C-6); 68.1 (C-4); 60.0 (linker); 48.7 (OCH$_3$); 39.2, 28.0, 26.3, 22.0, 21.9 (linker.) HRMS (ESI): Calcd. For C$_{12}$H$_{27}$N$_2$O$_8$P [M+H]$^+$: 359.1584, found 359.1587.

Example 2

Synthesis of MeOPN→2-β-D-Galp-(1→OMP

Figure 5:
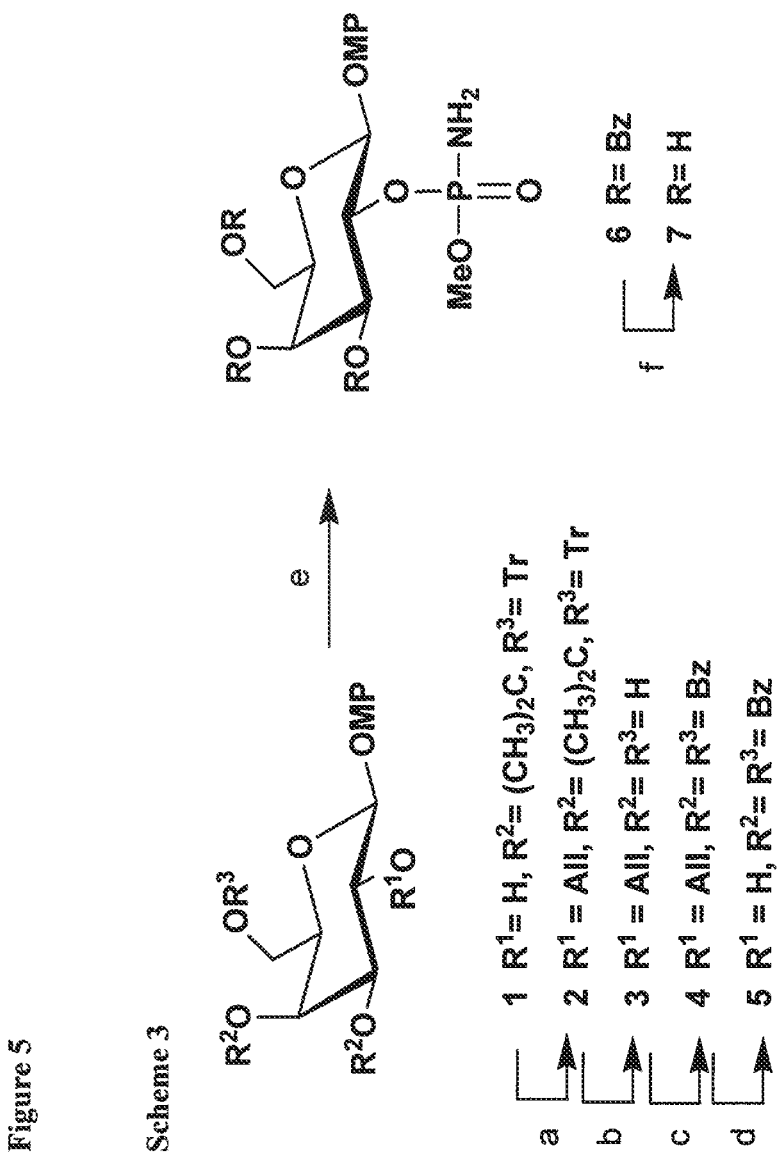
FIG. 5 depicts the synthesis of MeOPN→2-β-D-Galp-(1→OMP ("Scheme 3".) The reagents and conditions employed in the steps indicated therein are as follows: (a) AllBr, NaH, DMF, 0° C., 95%; (b) 80% AcOH, 80° C., 94%; (c) BzCl, pyridine, 97%; (d) $PdCl_2$, MeOH, 92%; (e) $PCl_2(O)OMe$, $Et_3N$, $CH_2Cl_2$, then $NH_{3(g)}$, 26%; (f) NaOMe, MeOH, 73%. All, allyl; Bz, Benzoyl.

Summary Synthesis of
MeOPN→2-β-D-Galp-(1→OMP (FIG. 5, Scheme
3)

Figure 14:
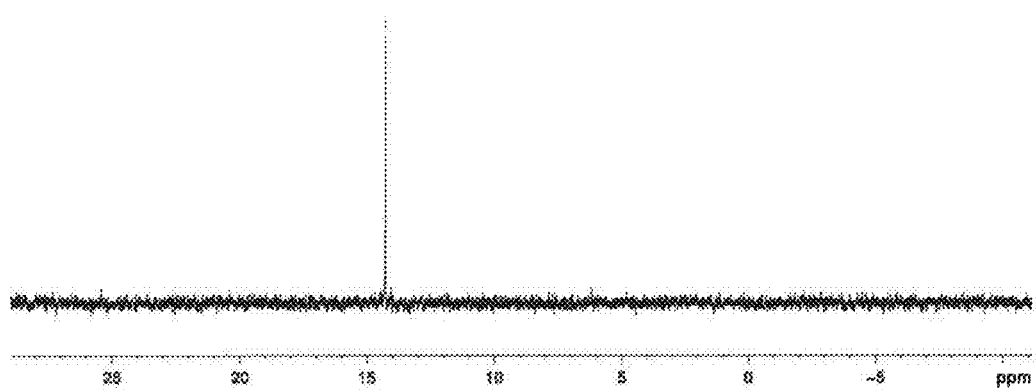
FIG. 14 depicts $^{31}P$ NMR (A) and $^1H$ NMR (B) of 4-Methoxyphenyl 2-O-methyl-phosphoramidyl-β-D-galactopyranoside performed using conventional methods.
Figure 14:
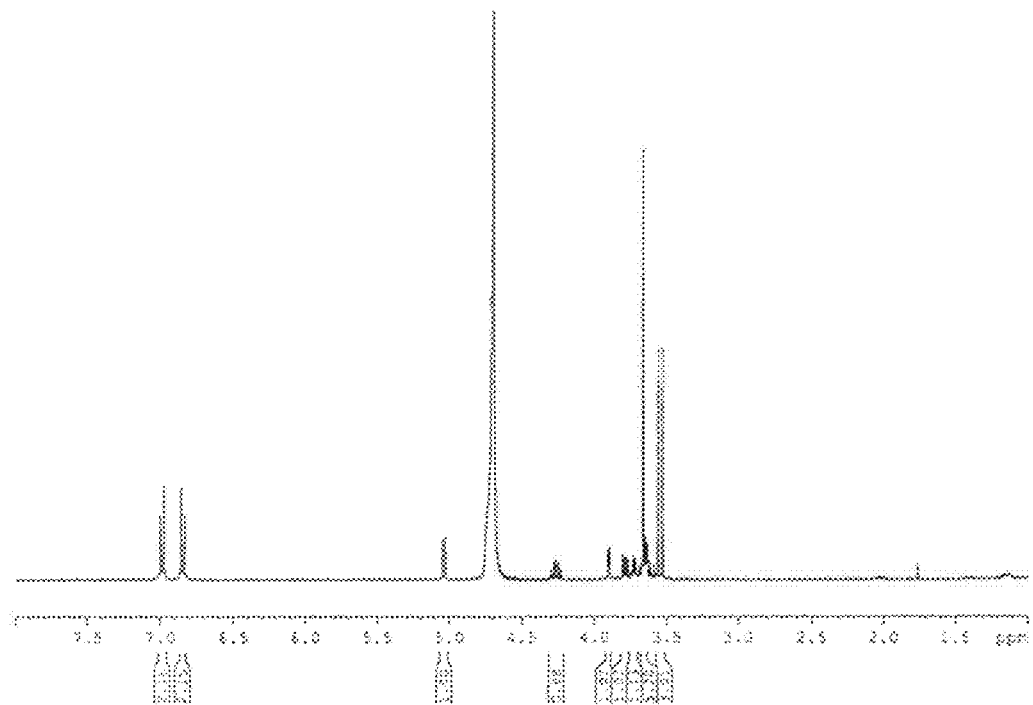

The synthesis of MeOPN→2-β-D-Galp-(1→OMP is depicted in FIG. 5, scheme 3. The synthesis of galactoside (product 7) began with a known compound, 4-methoxyphenyl 3,4-O-isopropylidene-6-O-trityl-β-D-galactopyranoside (product 1), which was prepared from D-galactose following published procedures (Scheme 1.) (Comfort D A, et al., *Biochem* 2007; 46:3319-3330.) To distinguish the C-2 position, O-allylation was performed generating product 2 in excellent yield. Since MeOPN can be removed by acidic media, suitable protecting groups needed to be installed. Thus, O-isopropylidene and O-trityl groups were removed giving product 3, which was then per-benzoylated affording product 4. Next, the allyl group was removed yielding a free 2-OH for modification. The introduction of MeOPN group to product 5 followed a strategy previously developed in our lab, involving first a phosphorylation with commercially available methyl dichlorophosphate followed by ammonolysis. (Jiao, Y. et al., *Carbohydr. Res.* (2015) doi: 10.1016/j.carres.2015.09.012). The $^{31}$P NMR spectrum of product 5 revealed two phosphorus signals of roughly 1:1 ratio due to the formation of two diastereoisomers. Product 6 was debenzoylated furnishing O-Me-phosphoramidate galactoside product 7. Interestingly, we were able to purify one of the diasteroisomers using flash chromatography. $^{31}$P NMR spectrum of the diastereoisomer 7* revealed a single signal at 14.27 ppm (see FIG. 14.)

Materials and Methods:

Conventional methods were used to synthesize the compounds, and all chemicals were purchased from commercial suppliers and used as received. Molecular sieves were activated by heating with a heating mantle under reduced pressure. Thin layer chromatography (TLC) was carried out on TLC silica gel F$_{254}$. Sugar compounds were visualized by UV light or by charring with 10% H$_2$SO$_4$ in ethanol. Flash chromatography was performed with silica gel P60, (43-60 μm, 230-400 mesh.) $^1$H NMR and $^{13}$C NMR spectra were recorded with Bruker 400 or 600 MHz spectrometers (Bruker Daltonics Inc, Billerica, Mass.) The proton signal of residual, non-deuterated solvent (δ 7.24 ppm for CHCl$_3$) was used as internal reference for $^1$H spectra. For $^{13}$C spectra, the chemical shifts are reported relative to the solvent (δ 77.1 ppm for CDCl$_3$.) Chemical shifts are reported in parts per million (ppm.) Coupling constants are reported in Hertz (Hz.) The following abbreviations are used to indicate the multiplicities: s, singlet; d, doublet; t, triplet; m, multiplet. Optical rotations were measured on a Rudolph Research Autopol III automatic polarimeter and concentration (c) is expressed in g/100 ml. High-resolution mass spectra for the synthetic compounds were recorded by electron spray ionization mass spectroscopy (time of flight analyzer.)

4-Methoxyphenyl 2-O-allyl-3,4-O-isopropylidene-6-O-trityl-β-D-galactopyranoside (Product 2)

A solution of product 1 (0.68 g, 1.2 mmol) dissolved in DMF (18 mL) with allyl bromide (0.16 mL, 1.8 mmol) was cooled to 0° C. Sodium hydride, 60% dispersion in mineral oil (57 mg, 1.4 mmol) was added and the reaction mixture was stirred for 1 h at 0° C. The reaction was then quenched with MeOH (2 mL), poured into ice-cold water (40 mL) and extracted with CH$_2$Cl$_2$ (3×50 mL.) The organic layer was dried over Na$_2$SO$_4$ and concentrated. Purification by flash chromatography eluting with 1:7 EtOAc-hexanes gave 2 (0.69 g, 95%.) [α]$_D^{25}$=+40.2° (c=0.05, CHCl$_3$); $^1$H NMR (400 MHz, CDCl$_3$): δ 7.46-7.19 (m, 15H, Ar); 7.10-6.75 (m, 4H, MeOC$_6$H$_4$); 5.92 (m, 1H, CH$_2$—CH=CH$_2$); 5.34-5.19 (m, 2H, CH$_2$—CH=CH$_2$); 4.67 (d, 1H, J=8.1 Hz, H-1); 4.36 (m, 2H, CH$_2$—CH=CH$_2$); 4.08 (m, 2H, H-3, H-4); 3.73 (s, 3H, OCH$_3$); 3.61-3.53 (m, 3H, H-2, H-5, H-6a); 3.34 (m, 1H, H-6b); 1.47 (s, 3H, CH$_3$); 1.29 (s, 3H, CH$_3$.) $^{13}$C NMR (100 MHz, CDCl$_3$): δ 155.2, 151.5, 144.0, 143.9 (Ar); 134.9 (CH$_2$—CH=CH$_2$); 128.8, 127.9, 127.8, 127.0, 126.9, 118.6, 118.3, 117.7, 117.4, 114.5, 114.4, 110.2, 109.3 (CH$_2$—CH=CH$_2$, Ar); 102.2 (C-1); 86.8 (CMe$_2$) 79.4 (C-2); 79.2; (C-3); 73.8 (C-4); 72.9 (CH$_2$—CH=CH$_2$); 72.6 (C-5); 63.0 (C-6); 55.6 (OCH$_3$); 27.9, 26.3 (CH$_3$.) HRMS (ESI): Calcd. For C$_{38}$H$_{40}$NaO$_7$ [M+Na]$^+$: 631.2672, found: 631.2670.

4-Methoxyphenyl 2-O-allyl-β-D-galactopyranoside (Product 3)

A solution of product 2 (0.69 g, 1.1 mmol) in 80% aqueous AcOH (10 mL) was stirred at 80° C. for 1 h. The reaction mixture was concentrated under reduced pressure. Purification by flash chromatography (1:1 EtOAc-hexanes) gave 3 (0.35 g, 94%.) [α]$_D^{25}$=+90.2° (c=0.2, CHCl$_3$); $^1$H NMR (400 MHz, CDCl$_3$): δ 7.01-7.78 (m, 4H, MeOC$_6$H$_4$); 5.91 (m, 1H, CH$_2$—CH=CH$_2$); 5.19 (m, 2H, CH$_2$—CH=CH$_2$); 4.83 (d, 1H, J=7.5 Hz, H-1); 4.53-4.25 (m, 2H, CH$_2$—CH=CH$_2$); 4.14 (m, 1H, H-5); 3.96 (m, 1H, H-6a); 3.85 (m, 1H, H-6b); 3.76 (s, 3H, OCH$_3$); 3.62 (m, 3H, H-2, H-3, H-4). $^{13}$C NMR (100 MHz, CDCl$_3$): δ 155.4, 151.1 (Ar); 134.5 (CH$_2$—CH=CH$_2$); 118.5, 118.2, 118.0, 114.6, 114.6 (CH$_2$—CH=CH$_2$, Ar); 102.6 (C-1); 78.4 (C-3); 75.9 (C-4); 73.7 (CH$_2$—CH=CH$_2$); 73.0 (C-2); 68.9 (C-5); 62.8 (C-6); 55.7 (OCH$_3$.) HRMS (ESI): Calcd. For C$_{16}$H$_{23}$O$_7$ [M+H]$^+$: 327.1445, found: 327.1422.

4-Methoxyphenyl 2-O-allyl-3,4,6-tri-O-benzoyl-β-D-galactopyranoside (Product 4)

To a solution of 3 (27 mg, 0.83 mmol) in CH$_2$Cl$_2$ (1 mL) and pyridine (65 μL, 8.3 mmol), BzCl (100 μL, 8.3 mmol) was added and the reaction mixture was stirred at room temperature for 18 hours. MeOH (1 mL) was added and the reaction mixture was concentrated under reduced pressure. Purification with flash chromatography (1:3 EtOAc-hexanes) gave product 4 (51 mg, 97%.) [α]$_D^{25}$=+48.6° (c=0.1, CHCl$_3$); $^1$H NMR (400 MHz, D$_2$O): δ 8.07-7.29 (m, 15H, Ar); 7.06-6.71 (m, 4H, MeOC$_6$H$_4$); 5.89 (d, 1H, J=2.7 Hz, H-4); 5.74 (m, 1H, CH$_2$—CH=CH$_2$); 5.42 (dd, 1H, J$_1$=3.5, J$_2$=10.0 Hz, H-3); 5.21-5.01 (m, 3H, CH$_2$—CH=CH$_2$, H-1); 4.57 (m, 1H, H-6a); 4.39-4.06 (m, 5H, CH$_2$—CH=CH$_2$, H-6b, H-5, H-2); 3.73 (s, 3H, OCH$_3$.) $^{13}$C NMR (100 MHz, CDCl$_3$): δ 171.2, 166.0, 165.7, 155.6, 151.2, 134.3, 133.8, 133.5, 133.2, 133.1, 132.9, 130.6, 130.2, 129.8, 129.7, 129.6, 129.4, 128.8, 128.5, 128.4, 118.8, 114.6 (Ar); 117.7 (CH$_2$—CH=CH$_2$); 102.8 (C-1); 78.7 (C-2); 74.0 (C-3); 73.6 (CH$_2$—CH=CH$_2$); 72.2 (C-5); 69.9 (C-4); 63.5 (C-6); 55.6 (CH$_3$.) HRMS (ESI): Calcd. For C$_{37}$H$_{34}$NaO$_{10}$ [M+Na]$^+$: 661.2050, found: 661.2041.

4-Methoxyphenyl 3,4,6-tri-O-benzoyl-β-D-galactopyranoside (Product 5)

To a solution of product 4 (45 mg, 70 μmol) dissolved in MeOH (1 mL), PdCl$_2$ (2 mg) was added and the reaction mixture was stirred at room temperature for 2 h. The reaction mixture was then filtered and concentrated. Purification with column chromatography (1:3 EtOAc-hexanes) gave product 5 (39 mg, 92%.) [α]$_D^{25}$=+78.2° (c=0.1, CHCl$_3$); $^1$H NMR (400 MHz, D$_2$O): δ 8.08-7.28 (m, 15H, Ar); 7.07-6.72 (m, 4H, MeOC$_6$H$_4$); 5.91 (d, 1H, J=3.5 Hz, H-4); 5.45 (dd, 1H, J$_1$=3.5, J$_2$=10.1 Hz, H-3); 5.00 (d, 1H, J=7.8 Hz, H-1); 4.60 (m, 1H, H-6a); 4.44 (m, 1H, H-6b); 4.34 (m, 2H, H-5, H-2); 3.73 (s, 3H, OCH$_3$). $^{13}$C NMR (100 MHz, CDCl$_3$): δ 166.0, 165.5, 155.7, 150.9, 133.7, 133.4, 130.0, 129.9, 129.8, 129.4, 129.2, 129.1, 128.5, 128.4, 118.6, 114.5 (Ar); 102.6 (C-1); 73.2 (C-3); 71.6 (C-5); 69.7 (C-2); 68.1 (C-4); 62.3 (C-6); 55.6 (OCH$_3$.) HRMS (ESI): Calcd. For C$_{34}$H$_{30}$NaO$_{10}$ [M+Na]$^+$: 621.1737, found: 621.1723.

4-Methoxyphenyl 3,4,6-tri-O-benzoyl-2-O-methyl-phosphoramidyl-β-D-galactopyranoside (Product 6)

To a solution of product 5 (18 mg, 0.030 mmol) and methyl dichlorophosphate (70 μL, 0.30 mmol) dissolved in CH$_2$Cl$_2$ (1 mL) with molecular sieves 4 Å, Et$_3$N (85 μL, 0.30 mmol) was added drop-wise. The reaction mixture was stirred at 40° C. for 12 hours. Upon completion of the reaction as judged by TLC, ammonia gas was injected into the reaction mixture through a needle. After 5 min, the reaction mixture was filtered and concentrated. Purification with column chromatography (EtOAc) yielded product 6

(5.4 mg, 26%.) $[\alpha]_D^{25}=+68.5°$ (c=0.05, CHCl$_3$); $^1$H NM (400 MHz, CHCl$_3$); δ 8.06-7.31 (m, 30H, Ar); 7.07-6.72 (m, 8H, MeOC$_6$H$_4$); 5.94 (m, 2H, H-4, H-4*); 5.54 (m, 2H, H-3, H-3*); 5.10 (m, 4H, H-1, H-1*, H-2, H-2*); 4.58 (m, 2H, H-6a, H-6a*); 4.45 (m, 2H, H-6b, H-6b*); 4.35 (m, 2H, H-5, H-5*); 3.73 (s, 3H, OCH$_3$); 3.67 (d, 3H, $^3J_{PH}$=11.6, POCH$_3$); 3.41 (d, 3H, $^3J_{PH}$=11.5, POCH$_3$*); 2.92 (d, 2H, NH$_2$); 2.51 (d, 2H, NH$_2$*) $^{13}$C NMR (100 MHz, CDCl$_3$): δ 166.0, 165.7, 165.6, 165.5, 155.8, 155.7, 150.8, 150.6, 133.8, 133.6, 133.5, 133.4, 130.1, 130.0, 129.9, 129.8, 129.4, 128.9, 128.8, 128.7, 128.6, 128.5, 128.4, 118.6, 114.7, 114.6 (Ar); 101.2, 101.1 (C-1); 73.9, 73.6 (C-2); 72.5, 72.4 (C-3); 71.7 71.5 (C-5); 68.0 (C-4); 62.1 (C-6); 55.6 (OCH$_3$); 53.6, 53.3 (POCH$_3$.) HRMS (ESI): Calcd. For C$_{35}$H$_{35}$NO$_{12}$P [M+H]$^+$: 692.1898, found: 692.1815.

4-Methoxyphenyl 2-O-methyl-phosphoramidyl-β-D-galactopyranoside (Product 7)

Product 7 (2.5 mg, mmol) was dissolved in 0.25 M methanolic MeONa (1 mL) and the mixture was stirred for 1 h at room temperature before it was neutralized with acetic acid and concentrated. Purification by flash chromatography eluting with 1:1 EtOAc-MeOH gave product 7 (1.0 mg, 73%.)

7: δ $^1$H NMR (400 MHz, D$_2$O): δ 6.97-6.83 (m, 8H, MeOC$_6$H$_4$); 5.05 (2d, 2H, H-1, H-1*); 4.28 (m, 2H, H-2, H-2); 3.91 (m, 2H, H-4, H-4*); 3.77-3.72 (m, 4H, H-3, H-3*, H-5, H-5*); 3.67-3.60 (m, 10H, H-6, H-6*, OCH$_3$); 3.59 (d, 3H, $^3J_{PH}$=11.5 Hz, POCH$_3$.) 3.56 (d, 3H, $^3J_{PH}$=11.5 Hz, POCH$_3$*.) $^{13}$C NMR (100 MHz, CDCl$_3$): δ 154.5, 150.7, 117.7, 114.9 (Ar); 99.7 (C-1); 77.0 (C-2); 75.3 (C-5); 71.6 (C-3); 68.6 (C-4); 60.5 (C-6); 55.6 (OCH$_3$); 53.9 (POCH$_3$.)

7*: $[\alpha]_D^{25}$=−11.0° (c=0.01, H$_2$O); $^1$H NMR (400 MHz, D$_2$O): δ 6.97-6.83 (m, 4H, MeOC$_6$H$_4$); 5.05 (d, 1H, J=7.8 Hz, H-1); 4.28 (m, 1H, H-2); 3.91 (d, 1H, J=3.5 Hz, H-4); 3.77 (dd, 1H, J$_1$=3.5 Hz, J$_2$=9.8 Hz, H-3); 3.72 (m, 1H, H-5); 3.67-3.60 (m, 5H, H-6, H-6', OCH$_3$); 3.56 (d, 3H, $^3J_{PH}$=11.5 Hz, POCH$_3$.) $^{13}$C NMR (100 MHz, CDCl$_3$): δ 154.5, 150.7, 117.7, 114.9 (Ar); 99.7 (C-1); 77.0 (C-2); 75.3 (C-5); 71.6 (C-3); 68.6 (C-4); 60.5 (C-6); 55.6 (OCH$_3$); 53.9 (POCH$_3$.) HRMS (ESI): Calcd. For C$_{14}$H$_{23}$NO$_9$P [M+H]$^+$: 380.1111, found: 380.1085.

Example 3

Immunodetection of MeOPN→6-α-D-Galp-(1→OMP and MeOPN→6-β-D-Galp-(1→O(CH$_2$)$_5$NH$_2$ by C. jejuni CPS Conjugate Antisera The synthetic p-methoxyphenyl and aminopentyl glycosides of the MeOPN→6-Gal construct, compounds MeOPN→6-α-D-Gal-(1→OMP and MeOPN→6-β-D-Galp-(1→O(CH$_2$)$_5$NH$_2$, synthesized as described in the above examples were tested for reactivity with antisera previously raised against C. jejuni CPS conjugates of serotypes HS1, HS3, HS4 and HS23/36. Notably, of the listed serotypes, only HS23/36 expresses MeOPN-6-Gal.

Materials and Methods

The synthetic construct MeOPN-6-Gal was adjusted to 1 mg/ml and 2 µl was spotted onto nitrocellulose membranes and allowed to dry. The individual spots were immunodetected with four different polyclonal antisera made against different conventional conjugate vaccines in which different C. jejuni polysaccharide capsules were conjugated to CRM$_{197}$: (1) rabbit serum against an HS23/36 conjugate (final dilution 1:1000 in 20 mM Tris, pH 7.4, 0.425 M NaCl, 0.05% Tween 20 (TBST); Monteiro et al., (2009) Infect. Immun. 77, 1128-1136; U.S. Pat. No. 9,084,809); (2) rabbit serum against an HS4 conjugate (final dilution 1:1000; Monteiro et al., (2009) Infect. Immun. 77, 1128-1136; U.S. Pat. No. 9,084,809); (3) mouse serum against an HS1 conjugate (final dilution 1:500; manuscript in preparation); and (4) mouse serum against an HS3 conjugate (final dilution 1:500; US 2015/0273037.) Secondary antibodies used were either goat anti-rabbit (for HS23/36 and HS4) or goat anti-mouse (HS1 and HS3 (Thermo-Pierce, Rockford, Ill.) Rabbit antibodies were obtained from Harlan Laboratories (Indianapolis, Ind.) and mouse antibodies were generated in house using conventional methods. Immunoblots were developed using a chemiluminescence kit (Pierce Supersignal West Femto Maximum Sensitivity Substrate, ThermoFischer Scientific, Waltham, Mass.) and imaged on a BioRad gel imager. (Bio-Rad Laboratories, Hercules, Calif.) The conjugate with linker was analyzed using similar methods.

Figure 6:
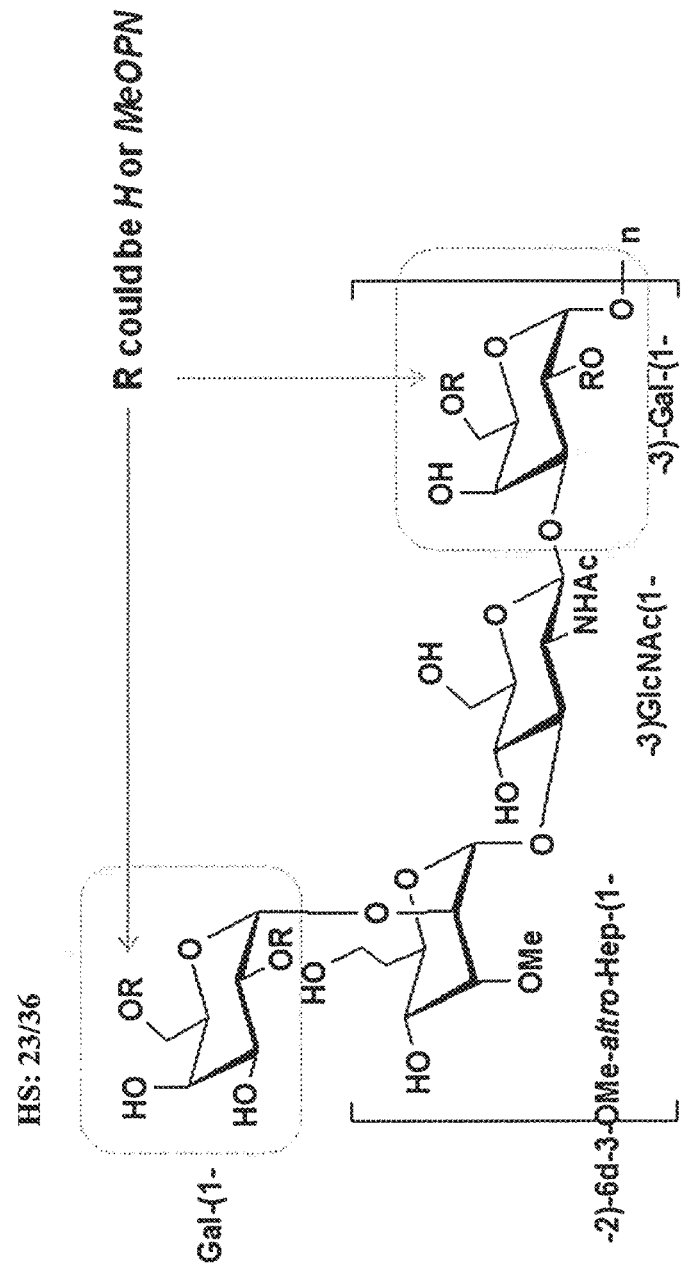
FIG. 6 depicts location of possible MeOPN moieties and capsule cross-reactivity to MeOPN-6-Gal with antibodies to multiple conjugate vaccines.
Figure 6:
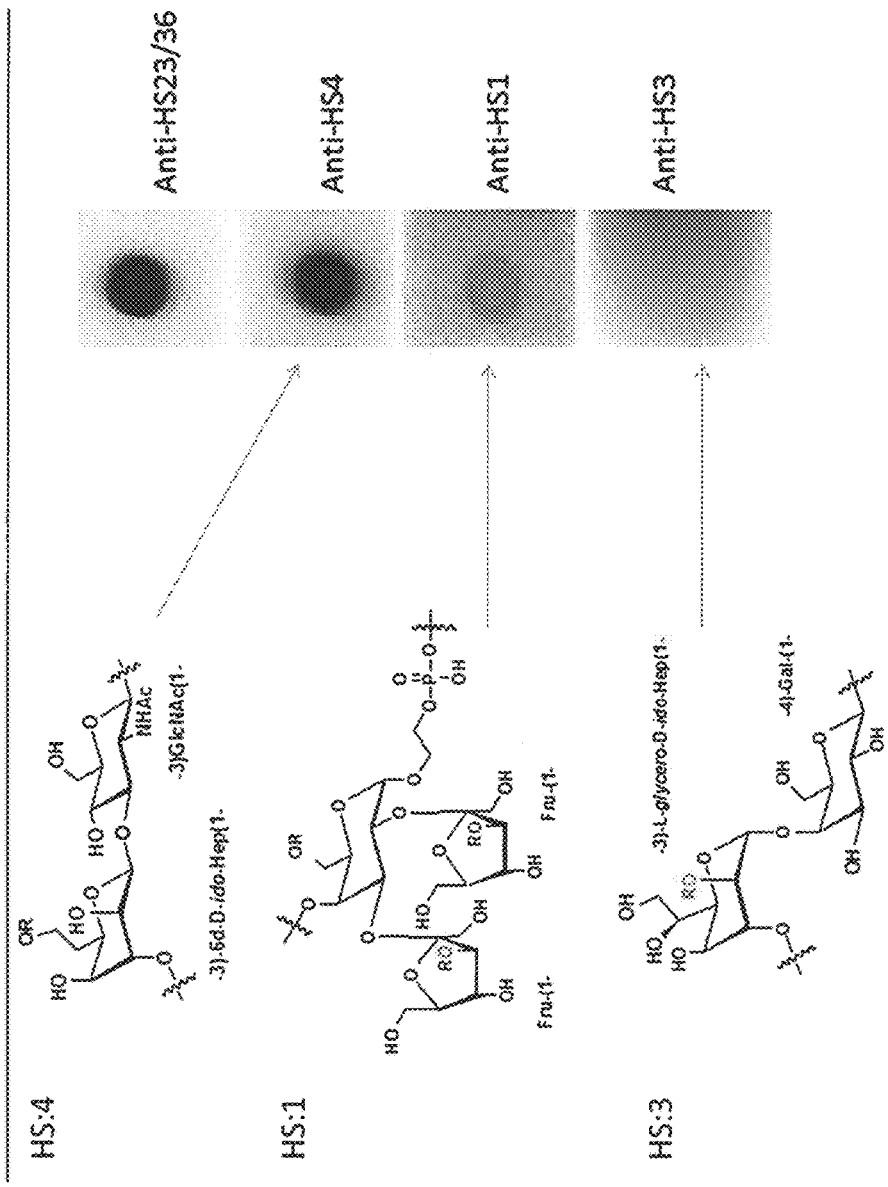

As illustrated in FIG. 6, the monosaccharide construct MeOPN-6-Gal was recognized by antibody against capsule polysaccharide isolated from HS23/36 conjugated to CRM$_{197}$ (CPS with a MeOPN at C-6 of Gal.) Unexpectedly, antibody against polysaccharide from HS4 conjugated to CRM$_{197}$ (CPS with MeOPN at C-7 of ido-heptose) also elicited a response equivalent to anti-HS23/36 CRM$_{197}$ conjugate against MeOPN-6-Gal. Also, anti-HS1-CRM$_{197}$ (CPS with low amounts of MeOPN at C-6 Gal) also reacted to MeOPN-6-Gal, although to a somewhat lesser extent. The HS3 CPS conjugate antisera (CPS with MeOPN at C-2 of ido-heptose) did not react with MeOPN-6-Gal. No reaction was observed between α-D-Gal-(1-OMP (devoid of MeOPN) and HS23/36 CPS conjugate antisera (data not shown.) Thus, the data show that antibodies generated against HS23/36, HS4 and HS1 all react with the synthetic MeOPN-6-Gal antigen. In contrast, these antibodies do not react with heterologous capsules. In other words, there is no detectable reactivity of anti-HS23/36 antibodies with purified HS4 or HS1 capsules.

The strong cross-reactivity with MeOPN-6-Gal exhibited against HS23/36 and HS4 antibody may be explained by the fact that MeOPN-6-Gal share epitopic structures with HS23/36 and HS4 capsule polysaccharides. One explanation may be that the MeOPN group in both HS23/36 and HS4 is to a primary hydroxyl. The cross reaction of MeOPN-6-Gal (HS23/36) with HS4, which contains MeOPN-7-6d-β-D-ido-Heptose, was unexpected, but may be due to the linkage of MeOPN to primary hydroxyl positions on both sugars. Indeed, as shown in FIG. 6, antibodies generated against HS23/36, HS4 and HS1 all react with the synthetic MeOPN-6-Gal antigen. In contrast, these antibodies do not react with heterologous capsules. In other words, there is no detectable reactivity of anti-HS23/36 antibodies with purified HS4 or HS1 capsules.

Figure 7:
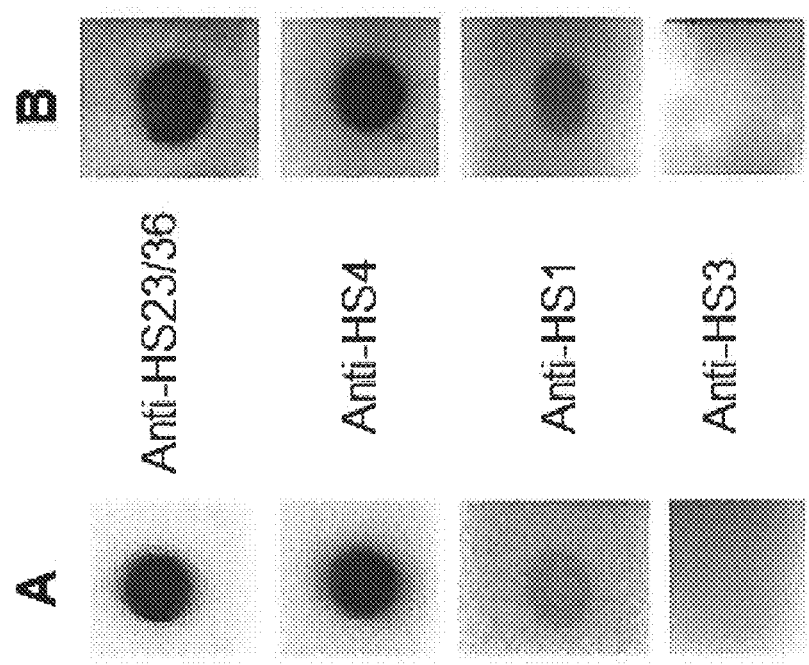
FIG. 7 depicts the immunodetection of MeOPN→6-α-D-Galp-(1→OMP (column A) and MeOPN→6-β-D-Galp-(1→O—(CH₂)₅NH₂ (column B) by C. jejuni CPS conjugate antisera of serotypes HS1 (1:500), HS3 (1:500), HS4 (1:2000) and HS23/36 (1:2000) as indicated in the center column. Dilutions were done in TBST (20 mM Tris, pH7.4, 0A25 N NaCl, 0.05% Tween 20.) Data show that antibodies to HS23/36, HS4 and HS1 serotypes of C. jejuni can react with the synthetic MeOPN-6-Gal construct either with or without added linker.

FIG. 7 compares the recognition of constructs MeOPN→6-α-D-Galp-(1→OMP in column A (same data as FIG. 6B) with data in column B using construct MeOPN→6-β-D-Galp-(1→O(CH$_2$)$_5$NH$_2$ using the indicated conjugate antisera. As depicted in FIG. 7, both constructs were strongly recognized by HS23/36 CPS conjugate antisera (whose CPS contains a MeOPN→6-α-D-Gal linkage in non-stoichiometric amounts), by HS4 CPS conjugate antisera (whose CPS has a non-stoichiometric MeOPN→7-6d-ido-Hep linkage), and, albeit with weaker intensity, by HS1 CPS conjugate antisera (that contains a very low amount of MeOPN→6-α-D-Gal.) As discussed above, the detection of synthetic MeOPN→6-D-Gal by HS23/36, HS4, and HS1 CPS conjugate antisera points to the fact that these polyclonal preparations contain specific antibodies for MeOPN units at primary positions. The HS3 CPS conjugate antisera (with MeOPN at C-2 of 6d-ido-Hep in CPS) did not react with either synthetic constructs MeOPN→6-α-D-Galp-(1→OMP or MeOPN→6-β-D-Galp-(1→O(CH$_2$)$_5$NH$_2$ (data not shown.) No reaction was observed between the Gal OMP and aminopentyl glycosides (devoid of MeOPN) and HS23/36 CPS conjugate or whole-cell antisera (data not shown.)

As indicated in FIG. 7, within the limits of detection, no difference in antisera reactivity was observed between MeOPN→6-α-D-Galp-(1→OMP and MeOPN→6-β-D-Galp-(1→O(CH$_2$)$_5$NH$_2$, which suggests that the recognition of MeOPN at the exocyclic C-6 position of Gal was not dependent on the anomeric configuration. That MeOPN→6-Gal was accessible in a conjugate format was confirmed by the reaction of HS23/36 whole-cell sera with a MeOPN→6-Gal CRM$_{197}$ conjugate. These data indicate that the synthetic MeOPN→6-Gal entities (regardless of anomeric configuration) not only react with antisera raised by homologous *C. jejuni* HS23/36 CPS conjugate, but also with those generated by serotypes HS1 and HS4, which also contain a MeOPN at a primary position (see, e.g., FIG. 1.)

Example 4

MeOPN-6-Gal is an Immunodominant Epitope

Until the discovery of a second MeOPN linkage at Gal-O-6 reported herein, MeOPN had only been reported on the O-2 position of galactose. Kanipes et al., (2006) *J Bacteriol.* 188, 3273-3279. The below experiment utilizing a CPS conjugate vaccine demonstrates that the MeOPN linkage at Gal-O-6 is immunodominant over MeOPN-2-Gal.
Materials and Methods Two microliters of a 1 mg/ml solution of synthetic MeOPN-6-Gal (prepared as disclosed above) and two isomers ("A" and "B") of MeOPN-2-Gal (prepared as disclosed herein) were spotted onto a nitrocellulose filters using conventional methods and allowed to dry. The filters were blocked with the blocking agent provided with Supersignal West Femto Maximum Sensitivity Substrate (Thermo-Pierce, Rockford, Ill.) Filters were mixed with primary rabbit polyclonal antibodies made against formalin killed whole cells of *C. jejuni* strain 81-176 (final dilution 1:500 in (20 mM Tris, pH7.4, 0.425 N NaCl, 0.05% Tween 20) (Bacon et al., (2001) *Mol. Microbiol.* 40, 769-777) or rabbit antibody to an HS23/36 polysaccharide-CRM197 conjugate vaccine (final dilution 1:1000) (Monteiro et al., (2009) *Infect. Immun.* 77, 1128-1136.) Filters were reacted with primary antibody overnight and then washed. Secondary antibody was goat anti-rabbit IgG (final dilution, 1:50,000) (Thermo-Pierce, Rockford, Ill.) After washing the filters were detected with Supersignal West Femto Maximum Sensitivity Luminescence Substrate and images were recorded on a BioRad gel imaging system (Bio-Rad Laboratories, Hercules, Calif.)

Figure 8:
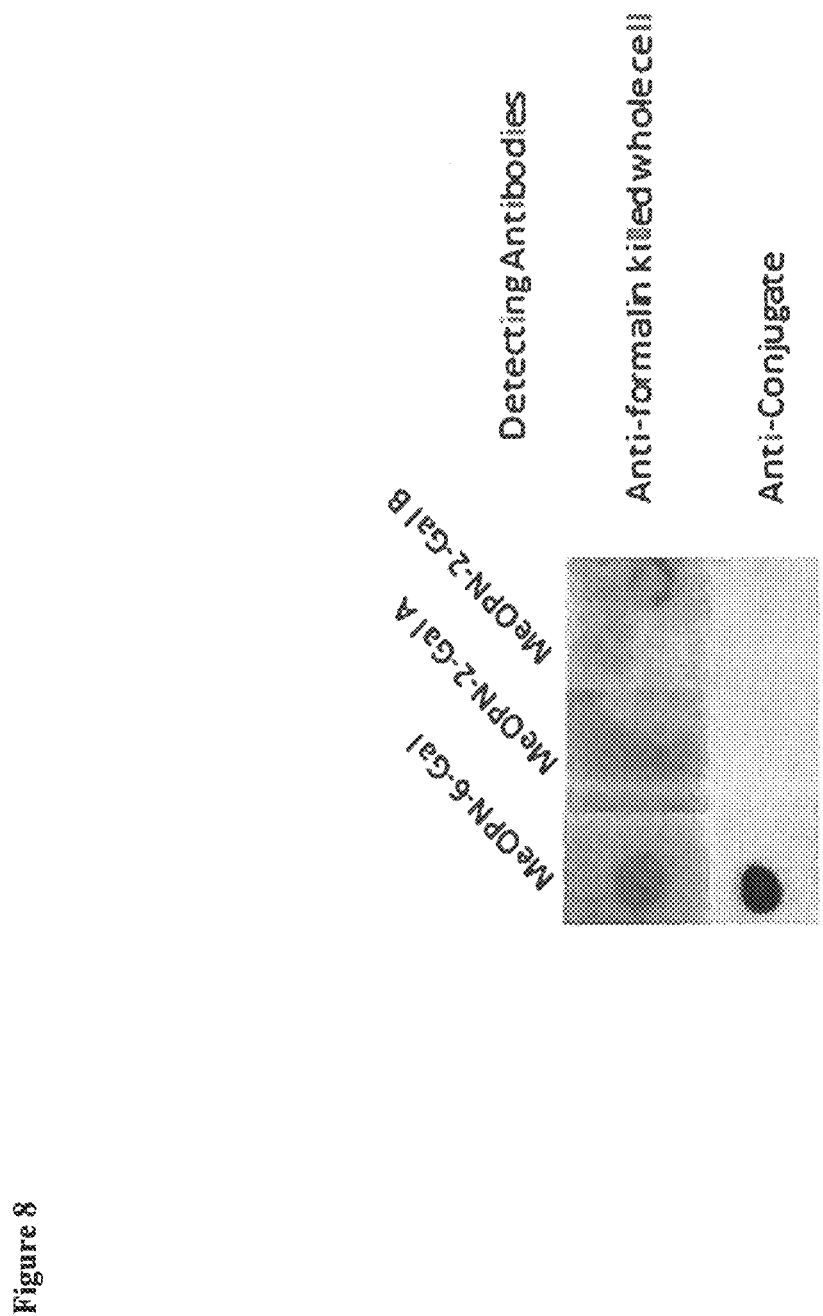
FIG. 8 depicts an immunoblot which demonstrates that rabbit antibodies to an HS23/36 polysaccharide-$CRM_{197}$ conjugate vaccine detected MeOPN-6-Gal, but did not detect isomers of MeOPN-2-Gal. These data clearly indicate the immunogenicity of the MeOPN-6-Gal monosaccharide and the immunodominance of the methyl phosphoramidate at the 6 position of Gal over MeOPN at the 2 position of Gal.

As depicted in FIG. 8, results clearly indicate that the rabbit antibody to an HS23/36 polysaccharide-CRM197 conjugate vaccine detected MeOPN-6-Gal, but did not detect either isomer of MeOPN-2-Gal. Similar results were obtained using the rabbit polyclonal antibodies, although some reactivity was detected against MeOPN-2-Gal B isomer. These data clearly indicate the immunogenicity of the MeOPN-6-Gal monosaccharide, and the immunodominance of the methyl phosphoramidate at the 6 position of Gal over MeOPN at the 2 position of Gal. The immunodominance of MeOPN-6-Gal over MeOPN-2-Gal has also been demonstrated in additional experiments, including studies using various mutant strains of *C. jejuni*, and results suggest that levels of MeOPN-6-Gal can modulate the immune response (see Example 8 below.) These data suggest that, in addition to the chemical synthesis of MeOPN-sugar epitopes as contemplated herein, CPS-based vaccines against *C. jejuni* might be improved by exploiting the immunodominance of MeOPN-modified sugars, e.g., by using strains that overexpress the immunodominant MeOPN-6-Gal epitope for capsule purification and vaccine production.

Example 5

Conjugation of MeOPN→6-β-D-Galp-(1→O(CH$_2$)$_5$NH$_2$ to Protein CRM$_{197}$

Figure 9:
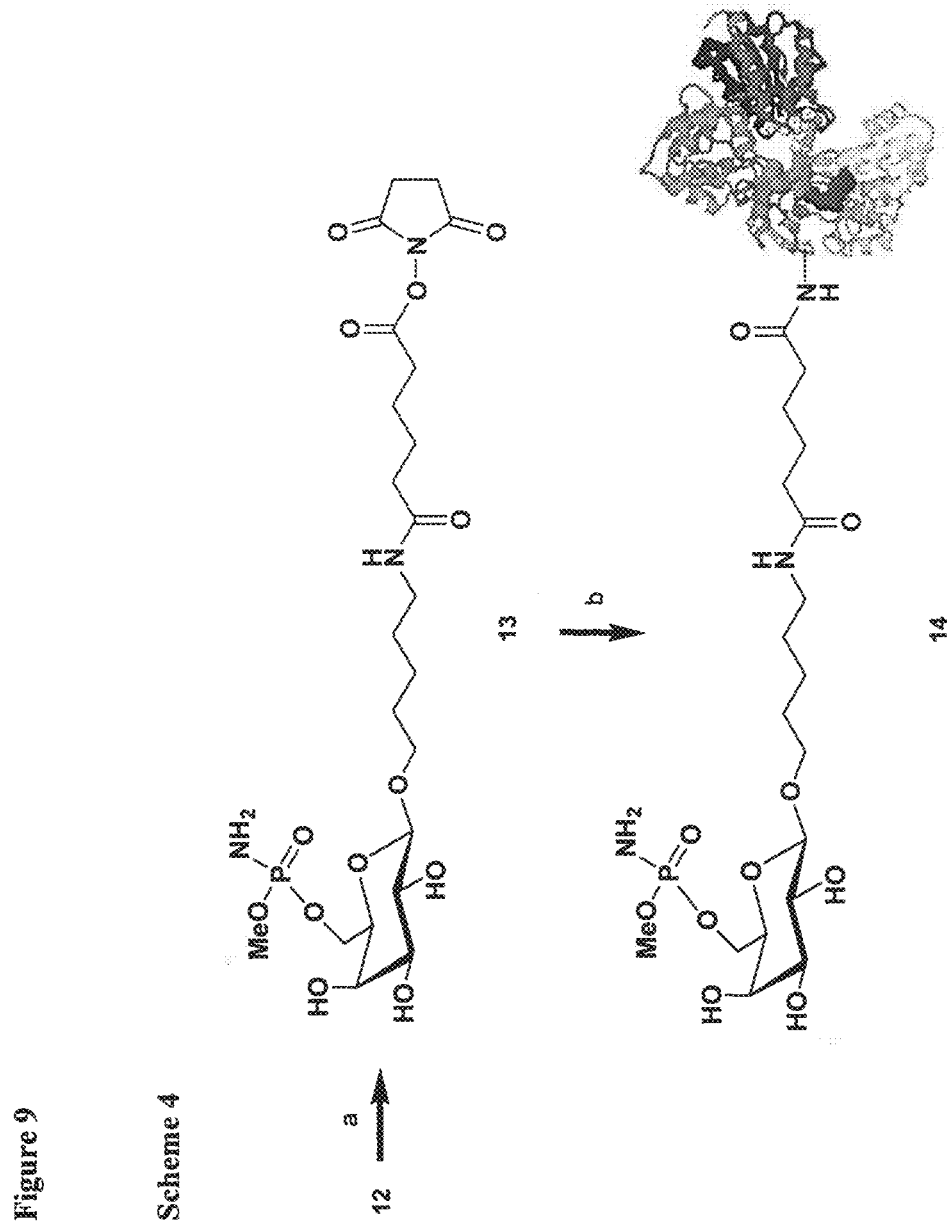
FIG. 9 depicts the conjugation of the linker-equipped galactoside with carrier protein, $CRM_{197}$ ($CRM_{197}$ is depicted as ribbon diagram) ("Scheme 4".) The reagents and conditions employed in the steps indicated therein are as follows: (a) di-N-hydroxy-succinimidyl adipate ester, $Et_3N$ DMSO; (b) $CRM_{197}$, 70 mM NaPi, pH 7.0.

The synthesis of the synthetic construct linked to a protein carrier to form a conjugate is depicted in FIG. 9 (Scheme 4.) The linker equipped galactoside (compound 12 from FIG. 3 or compound 9 from FIG. 4) (4.5 mg) and an excess of adipic acid N-hydroxysuccinimido diester (10 equiv.) was dissolved in DMSO (1 ml.) Triethylamine (60 µl), was added drop-wise and the reaction mixture was stirred at room temperature for 4 h. After concentration under reduced pressure, the residue was extracted with H$_2$O, followed by purification with column chromatography (3:1 EtOAc-Hexane) giving the activated monosaccharide, compound 13. This resulting half ester, (compound 13) was then condensed with the amino groups of the protein CRM$_{197}$ in phosphate buffer (NaPi buffer, pH 7) to yield compound 14. Specifically, conjugation was carried out with the activated monosaccharide with CRM$_{197}$ at a molar ratio of 100:1 (moles of active ester per moles of protein) in 70 mM phosphate buffer pH 7.0. After stirring 3 days at room temperature, the conjugate (compound 14) was dialyzed against running water.

Figure 10:
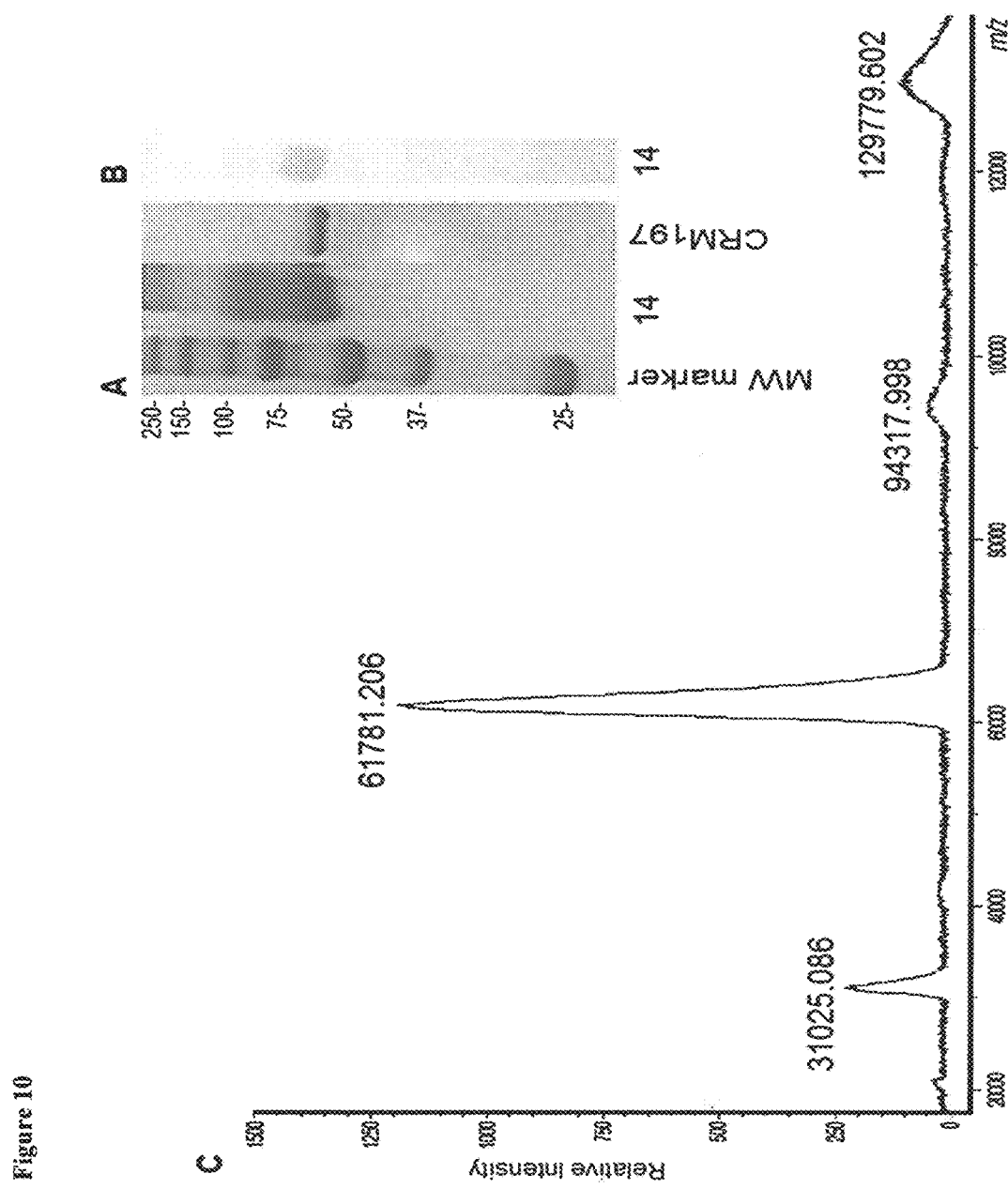
FIG. 10 depicts the analysis and confirmation of conjugation of linker equipped galactoside with carrier protein: (A) Gel electrophoresis of $CRM_{197}$ and MeOPN→6-β-D-Gal $CRM_{197}$ (compound 14); (B) Western blot of MeOPN→6-β-D-Gal $CRM_{197}$ (compound 14) with C. jejuni HS23/36 whole cell antisera; and (C) the MALDI-TOF/MS of MeOPN→6-β-D-Gal $CRM_{197}$ (compound 14.) The MeOPN-6-Gal-$CRM_{197}$ vaccine gave a major peak of mass 61,781.206. The mass for $CRM_{197}$ in a similar MALDI experiment was 57,967 daltons (not shown.) Thus, the mass difference was about 3,814 daltons. Since the mass of MeOPN-6-Gal and the linker is 461 daltons (data not shown), this indicates that approximately 8 MeOPN-6-Gal-linker moieties were added per $CRM_{197}$ molecule.

The conjugation was analyzed and confirmed with SDS-PAGE gel and mALDI-TOF. Specifically, the conjugation of MeOPN→6-β-D-Galp-(1→O(CH$_2$)$_5$NH$_2$ to CRM$_{197}$ was analyzed and confirmed by gel electrophoresis (FIG. 10A) Western blot (FIG. 10B) and mass spectrometry (mALDI-TOF) (FIG. 10C) according to conventional methods.
Materials and Methods The MeOPN-6-Gal construct linked to CRM$_{197}$ was analyzed and characterized by SDS-PAGE and immunoblotting using conventional methods. Samples of the synthetic MeOPN-6-Gal linked to CRM$_{197}$ (2.5 µg and 5 ug by weight) were analyzed on 12.5% SDS-PAGE gels and either stained with GelCode Blue (ThermoFischer Scientific, Waltham, Mass.) or transferred to nitrocellulose and immunodetected with rabbit poly-clonal antibodies to whole cells of *C. jejuni* 81-176 (HS23/36) (Bacon et al., (2001) *Mol. Microbiol.* 40, 769-777.) The stained SDS-PAGE gel indicated that the vaccine conjugate was heterogeneous in size, ranging from slightly larger than unconjugated CRM$_{197}$ to >250 Kd. (FIG. 10A.) Results from immunoblotting indicate that the vaccine conjugate reacted with rabbit polyclonal antibodies to whole cells of *C. jejuni* strain 81-176 indicating cross reaction between the capsule and the conjugate (data not shown.) Due to the fact that the final product (the conjugate) contained diastereoisomers of MeOPN, only half of the MeOPN→6-D-Galp epitopes reflected those in the native CPS. Even so, Western blot analysis with HS23/36 whole cell antisera showed that the conjugate exposed MeOPN→6-D-Gal epitopes that mimic MeOPN stereochemistry and linkage on cell-surface (FIG. 10B.)

The conjugate was also analyzed by MALDI-TOF using conventional methods to more accurately determine masses of the conjugate. Briefly, sinapinic acid (Sigma Aldrich, St. Louis, Mo.) was saturated in 30:70 (v/v) acetonitrile (ACN): 0.1% trifluoroacitic acid (TFA) in water as the matrix. The matrix and sample (1 mg/mL) were pre-mixed in equal volumes, and 1 μL was deposited on a ground steel plate by dry droplet method for analysis. Microflex LRT matrix-assisted laser desorption and ionization time-of flight (MALDI-TOF) mass spectrometer (Bruker Daltonics Inc, Billerica, Mass.) was set at linear mode with positive ion detection to obtain the mass spectra. Results indicate that the MeOPN-6-Gal-CRM$_{197}$ conjugate vaccine gave a major peak of mass 61,781. The mass for CRM197 in a similar MALDI experiment was 57,967 daltons (not shown.) Thus, the mass difference is 3,814 daltons. Since the mass of MeOPN-6-Gal and the linker is 461 daltons (data not shown), this indicates that approximately 8 MeOPN-6-Gal-linker moieties were added per CRM$_{197}$ molecule. No larger form was detected, however, this may be due to the fact that larger molecules are more difficult to detect using the Bruker Daltonics instrument.

Example 6

MeOPN→6-β-D-Gal CRM$_{197}$ Conjugate Antibodies Recognize *C. jejuni* HS23/36 Cell-Surface and have Bactericidal Activity We have previously demonstrated that immunogenic capsule polysaccharide conjugate vaccines ("conventional" vaccines) against *C. jejuni* elicit serum bactericidal antibodies (SBAs) (manuscript in preparation.) In other words, the antibodies generated against the conventional vaccine can bind to the bacterium in the presence of complement and induce bacterial lysis. As discussed in the above examples, MeOPN-6-Gal has been synthesized and shown to react with antibodies to conventional CRM$_{197}$ conjugate vaccines based on both HS23/36 and HS4. A vaccine conjugate composed of MeOPN-6-Gal linked to CRM$_{197}$ with approximately 8 MeOPN-6-Gal moieties per protein was synthesized as provided above and tested for immunogenicity in rabbits.

Materials and Methods

Using conventional methods and commercially available reagents, a rabbit was immunized with four doses of MeOPN-6-Gal linked to CRM$_{197}$ vaccine conjugate (each at 250 ug) with Freund's adjuvant. The final serum was used in an ELISA in which *C. jejuni* 81-176 capsule conjugated to BSA was the detecting antigen. The endpoint titer of the serum was 1:200. The rabbit serum generated against MeOPN-6-Gal was heat-inactivated by heating to 56° C. for 30 minutes to inactivate endogenous complement. As a control, the pre-bleed of the same rabbit (prior to immunization) was also heat inactivated. Sera were serially diluted in a microtiter plate, mixed with *C. jejuni* 81-176 and baby rabbit complement. The plate was incubated at 37° C. under microaerobic conditions. Aliquots from each well were plated onto Mueller Hinton agar plates to enumerate the surviving bacterial cells. The results are reported as the fold-increase in killing between the pre-bleed and the final bleed of the immunized rabbit.

Figure 11:
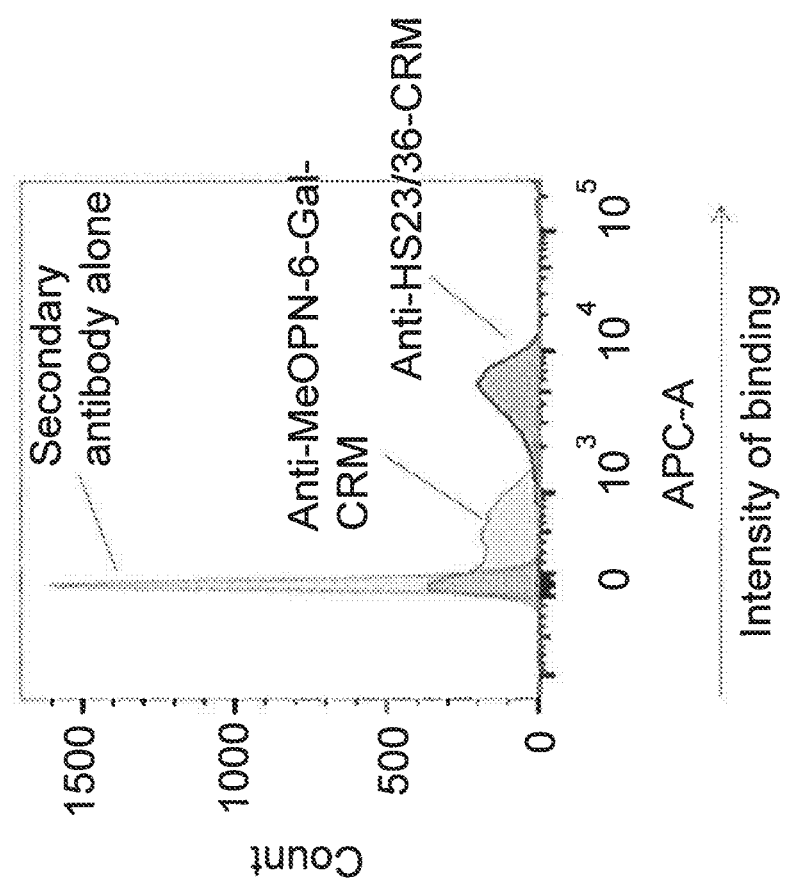
FIG. 11 depicts flow cytometry analysis of C. jejuni HS23/36 cells with antisera raised by HS23/36 CPS conjugate (peak between approx. $10^3$-$10^4$) and synthetic MeOPN→6-β-D-Gal $CRM_{197}$ conjugate 14 (peak between approx. 0 and $-10^3$). Peak at 0 represents binding of secondary antibody alone. APC-A, Allophycocyanin. Data demonstrate that a synthetic conjugate vaccine of the invention is capable of conjuring up antibodies in rabbits specific to the CPS MeOPN→6-D-Gal linkage exposed on the cell-surface of C. jejuni HS23/36 cells.
Figure 12:
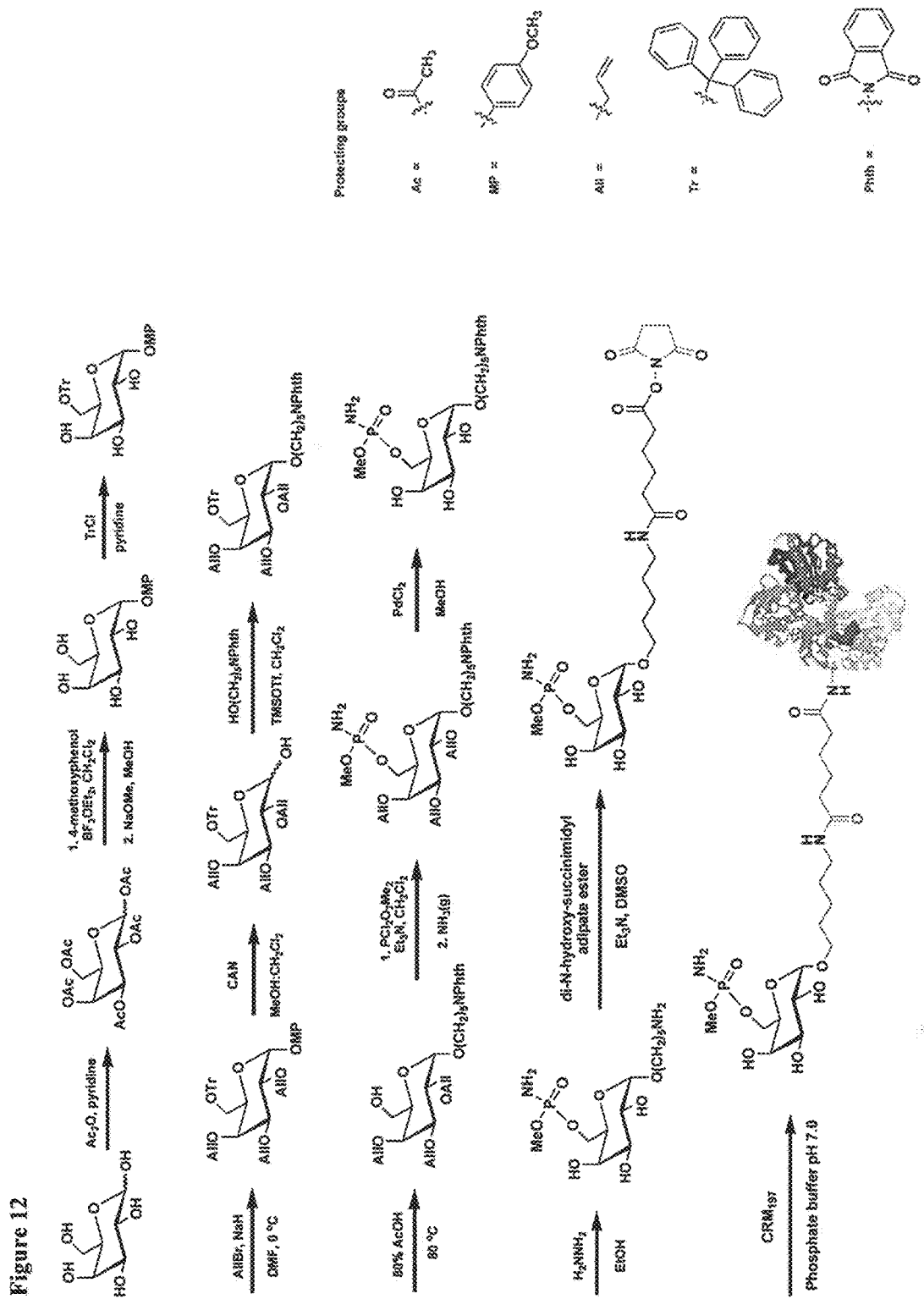
FIG. 12 depicts a summary of the synthesis of the MeOPN-6-Gal monosaccharide construct and conjugation to the carrier protein $CRM_{197}$. Ac, acetyl; MP, Methoxyphenyl; All, allyl; Tr, trityl; Phth, phthalimido.

The results for the rabbit immunized with the MeOPN-6-Gal-CRM$_{197}$ conjugate vaccine indicated a 16-fold increase in serum bacteriocidal activity. Results from flow cytometry are depicted in FIG. 11. Data indicate that the conjugate vaccine (e.g., compound 14 in FIG. 9) is capable of inducing antibodies in rabbits specific to the CPS MeOPN→6-D-Gal linkage exposed on the cell-surface of *C. jejuni* HS23/36 cells. The intensity of binding to *C. jejuni* HS23/36 cells was higher using antibodies raised by the native CPS conjugate. Intensity of binding to *C. jejuni* HS23/36 cells was lesser with the antibodies raised to the synthetic vaccine, and a portion of the cells did not react with MeOPN→6-D-Gal antibodies at all. However, binding of these antibodies to the surface of HS23/36 cells is consistent with the observed rise in SBA titer discussed above.

Example 7

Synthesis of Polymeric Constructs Comprising *Campylobacter jejuni* Synthetic Antigens Immunogenic synthetic constructs comprising one or more synthetic MeOPN-monosaccharides and optionally associated with one or more other saccharides are contemplated herein. Examples of such polymeric constructs which have been synthesized are depicted herein in FIG. 15 and FIG. 18.

Materials and Methods

The multi MeOPN-6-Gal polymeric conjugate of FIG. 15 was synthesized using conventional methods, commercially available reagents, and monosaccharides disclosed herein and in the proceeding examples. Lintner starch (100 mg) was activated with 0.04 M NaIO4 in 0.1 M NaOAc buffer (100 ml) pH 4, at 4° C. for 3 days. After 2 days of dialysis against water, 1000 Da molecular cutoff, the product mixture was centrifuged. The supernatant was lyophilized and further purified on a Bio-Gel P-2 column.

The activated starch (8 mg) was chemically conjugated with MeOPN→6-β-D-Galp-(1→O(CH2)$_5$NH$_2$ (4 mg) in 0.1 M borate buffer (5 ml), pH 9. Sodium cyanoborohydride (40 mg) was added and the reaction mixture was stirred for 1 day at RT and 2 days at 37° C. The conjugate was then dialyzed against running water (1000 Da) for 2 days and then lyophilized.

Figure 16:
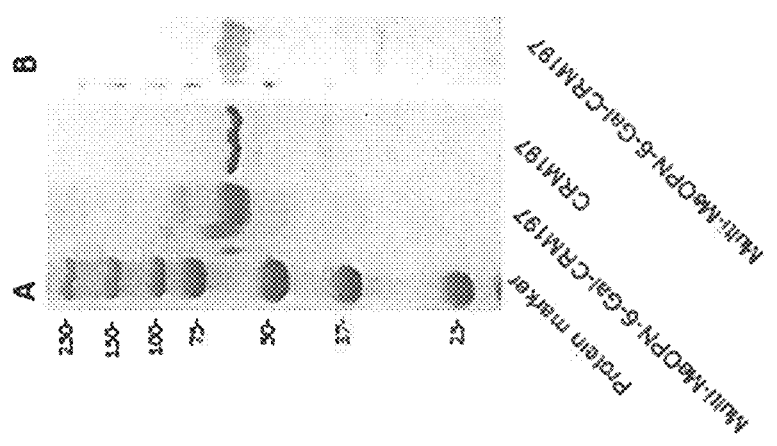
FIG. 16 depicts a 12.5% SDS-PAGE gel (sodium dodecyl sulfate-polyacrylamide gel electrophoresis) (A) and immunoblot (B) of the synthetic polymeric construct of FIG. 15 comprising multiple MeOPN-6-Gal monosaccharides. As indicated, FIG. 16(A) includes lanes for the molecular weight marker, the synthetic construct, and carrier protein alone.
Figure 17:
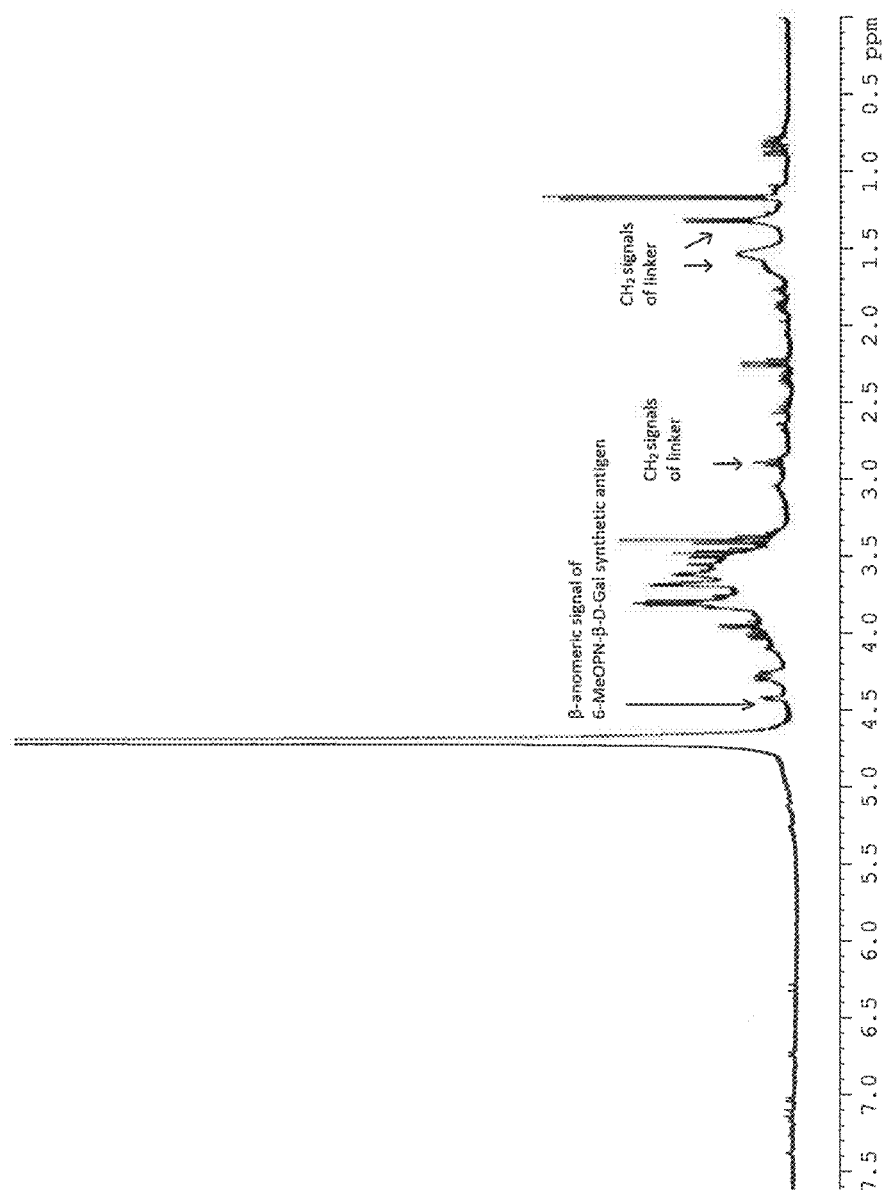
FIG. 17 depicts $^1H$ NMR of the synthetic polymeric construct of FIG. 15 showing the successful attachment of the C. jejuni MeOPN-6-Gal synthetic antigen to the modified (oxidized) starch polymer. X axis is ppm. The arrow at approximately 4.5 ppm indicates the β-anomeric signal of 6 MeOPN-β-D-Gal synthetic antigen; the remaining arrows indicate $CH_2$ signals of the linker.

The starch-sugar conjugation product (4 mg) was conjugated with CRM$_{197}$ (4 mg) in 0.1 M borate buffer (5 ml), pH 9. Sodium cyanoborohydride (40 mg) was added and the reaction mixture was stirred for 1 day at RT and 2 days at 37° C. The conjugate was then dialyzed against running water (1000 Da) for 2 days and then lyophilized. The resulting synthetic conjugate was characterized using Western gel and immunoblotting and 1H NMR as provided in FIGS. 16 and 17, respectively. Briefly, for the immunoblot, the synthetic conjugate was electrophoresed on a 12.5% polyacrylamide gel in duplicate. Part of the gel was stained and the other part was transferred to nitrocellulose using a Transblot Turbo System (BioRad, Hercules, Calif.) and immunodetected with rabbit hyperimmune sera to formalin killed whole cells of *C. jejuni* strain 81-176 (final dilution 1:500 in TBST which is 20 mM Tris, pH 7.4, 0.425 N NaCl, 0.05% Tween 20). The filter was reacted with primary antibody overnight and then washed. Secondary antibody was goat anti-rabbit IgG (final dilution 1:50,000 in TBST). After washing, the filter was detected with Supersignal West Femto Maximum Sensitivity Luminescence Substrate and images were recorded on a BioRad gel imaging system.

The synthetic polymeric conjugate depicted in FIG. 18 was similarly prepared using conventional methods and reagents, and conjugated to a protein carrier. In contrast to the conjugate depicted in FIG. 15, the synthetic construct depicted in FIG. 18 comprises not only multiple MeOPN-6-Gal monosaccharides, but also multiple MeOPN-2-Gal and MeOPN-1-Fru monosaccharides. As described above, the various monosaccharides are chemically associated (conjugated) using a starch backbone. The sugar is chemically equipped with a linker that can serve as a bridge between the sugar and the starch. A carrier protein is affixed to the construct.

Example 8

Phase Variation of Genes Encoding Methyl Phosphoramidate Transferases in *Campylobacter Jejuni* Modulates Capsule Structure and Resistance to Complement-Mediated Killing of *Campylobacter Jejuni*

The genes for biosynthesis of MeOPN are highly conserved among strains of *C. jejuni*, while the genes encoding MeOPN transferases are highly conserved at the 5' end of the gene, but divergent at the 3' end. The conserved 5' ends are also characterized by the presence of homopolymeric G tracts that undergo phase variation (PV) by slip strand mismatch repair during replication [12]. Thus, the population can consist of mixtures of cells with these genes in either "ON" or "OFF" configurations, a trait characteristic of genes encoding multiple surface antigens of *C. jejuni* [12-17]. The high frequency of PV is due to lack of mismatch repair (MMR) enzymes [12, 18].

As discussed above, *C. jejuni* CPSs have been shown to be important for pathogenesis. Non-encapsulated mutants were attenuated in a ferret model of diarrhea) disease and were reduced in their ability to colonize chickens, mice and piglets [19-22], and there are conflicting reports on the role of MeOPN in pathogenesis of a *Galleria mellonella* model of disease [22, 23].

Capsules are a major factor in resistance to complement mediated killing, and, in the case of *C. jejuni* 81-176 (HS23/36), MeOPN is essential for complement resistance. Thus, mutants expressing a polysaccharide CPS lacking MeOPN were as sensitive to complement-mediated killing as a mutant lacking CPS [21, 22]. Polysaccharide CPSs of two serotypes, HS2 and HS23/36, have also been shown to have immunomodulatory effects in vitro [21, 24], and the immunomodulatory effects for 81-176 have been confirmed in vivo in a mouse model [25]. MeOPN has also been shown to serve as a phage receptor [26, 27].

Figure 19:
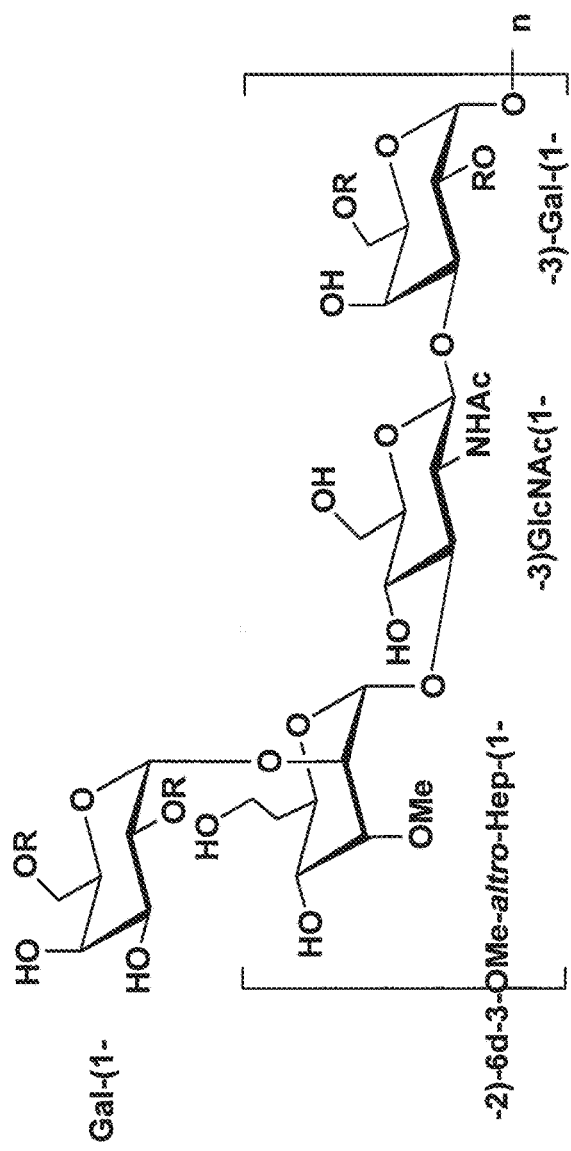
FIG. 19 depicts the structure of two repeats of the 81-176 capsular trisaccharide (A). The position of MeOPN-2-Gal and MeOPN-6-Gal is indicated.
Figure 19:
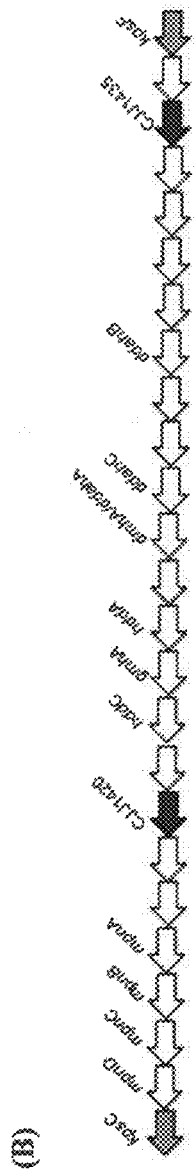

The 81-176 CPS is a repeating trisaccharide of galactose, 3-O-methyl-6-deoxy-altro-heptose, and N-acetyl glucosamine (see FIG. 19A). Strain 81-176 contains genes predicted to encode two putative MeOPN transferases, CJJ81176_1420 and CJJ81176_1435 (FIG. 19B) [22]. MeOPN has been reported on both the 2 position of galactose (MeOPN-2-Gal) and data provided herein demonstrate that an MeOPN moiety is also found on the 6 position of galactose and that anti-conjugate antibodies recognized synthetic MeOPN-6-Gal. Here, we confirm not only that MeOPN-6-Gal and, to a lesser extent, MeOPN-2-Gal, are the immunodominant epitopes on intact CPS recognized by conjugate vaccines, but also that phase variation of the MeOPN epitopes can modulate CPS structure and levels of resistance to complement-mediated killing.

Methods and Materials

Strains and growth conditions: All work was done in the 81-176 strain of *C. jejuni*. Mutants of this strain are listed in Table 1.

TABLE 1

Mutants of 81-176 used in this study.

| Strain no. | Genotype | Strain Background | CJJ1420 genotype | CJJ1435 genotype | Reference |
|---|---|---|---|---|---|
| 3468 | kpsM::aph3 | wildtype | variable | variable | 34 |
| 3469 | kpsM::aph3 (pRY111 + kpsMT) | 3468 | variable | variable | 34 |
| 3390 | mpnC::cat | wildtype | variable | variable | 21 |
| 3391 | mpnC::cat complement | 3390 | variable | variable | 21 |
| 3477 | CJJ1420::aph3 | wildtype | negative | variable | This work |
| 3498 | CJJ1420::aph3, hipO::CJJ1420R* + cat | 3477 | ON | variable | This work |
| 3636 | CJJ1435::cat | wildtype | variable | negative | This work |
| 3637 | CJJ1435::cat, astA::CJJ1435R* + aph3 | 3636 | variable | ON | This work |
| 3479 | CJJ1420::aph3, CJJ1435::cat | 3477 | negative | negative | This work |

*R, homopolymeric tract of Gs that is subjected to phase variation was repaired.

*C. jejuni* was routinely cultivated on Mueller Hinton agar at 37° C. under microaerobic conditions. Media was supplemented with antibiotics as needed. For capsule extraction, cells were grown in porcine brain heart infusion broth or plates (Difco).

Oligonucleotide primers: All oligonucleotide primers used are listed in Table 2 and were synthesized by Life Technologies.

TABLE 2

Primers used in this study.

| Primer name | Sequence | SEQ ID NO. |
|---|---|---|
| pg12.13 | GGAATTCGATGATTATTTTATAGATATTGGTGTGCCTGAGG | 1 |
| pg12.14 | CCCTCGAGGGGATATTACTATCGACTATATCGTAACTATTACAACC | 2 |
| pg12.25 | CCAGCTGAACTTGCTTGGGAGATG | 3 |

TABLE 2-continued

Primers used in this study.

| Primer name | Sequence | SEQ ID NO. |
|---|---|---|
| pg12.26 | GGGATATTACTATCGACTATATCGTAACTATTACAACC | 4 |
| pg10.07 | GTGTGATGTGGTGGTTACGTTGAATTCGGG | 5 |
| pg10.08 | CTCAAATCTATAGTAAGTGGCATGATTAACATGCCAAGC | 6 |
| pg14.67 | CATCCTTATCCTTCATTACTTGATCC | 7 |
| pg14.68 | CGTGGAACATGTTTATTTATCATATGC | 8 |
| pg12.31 | CATGAAAATCCTGAGCTTGGTTTTGATG | 9 |
| pg12.32 | GTATTTTAAAACTAGCTTCGCATAATAAC | 10 |
| pg12.33 | GCGCCCATGGGTTAACGGAGCACTTCCATGACCACCTCTTCC | 11 |
| pg12.34 | GCGCCCATGGTCTAGAAGATCTCCTATTTATGCTGCTTCTTTGCTTCTGG | 12 |
| pg12.29 | CGGGATCCAAAGGAGAAACCCTATGTATAACCCAAACTCAGC | 13 |
| pg12.30 | GGAATTCGTAAAATCCCCTTGTTTCATATTGATTCCTTTCTCTAATTTTAAACAC | 14 |
| pg12.37 | GCTATGATTGAGTTTACAAACAATGGAGGAGGATATATAGCATTATTTAAAAAACTC | 15 |
| pg12.38 | GAGTTTTTAAATAATGCTATATATCCTCCTCCATTGTTTGTAAACTCAATCATAGC | 16 |
| pg14.35 | GGAATTCCTATATTATAAGATAATAACACAATTCGCCTCCTATG | 17 |
| pg14.03 | CGGGATCCAGGAGAAACCCTATGTATAACCCAAACTCAGC | 18 |
| pg14.09 | GCTATGATTGAGTTTACAAACAATGGAGGAGGATATATAGCATTATTTAAAAAACTC | 19 |
| pg14.10 | AGTTTTTTAAATAATGCTATATACCTCCTCCTTTGTTTGTAAACTCAATCATAGC | 20 |

Conjugate vaccine synthesis: Capsular polysaccharide isolation and conjugation to CRM197 (Pfenex) were done as described in Monteiro et al. [30]. The three vaccines were called CCV [30], DB4, and CJCV1.

Rabbit polyclonal antisera: Rabbit hyperimmune polyclonal antibodies were generated against three batches of HS23/36-CRM197 conjugate vaccines, CCV1 [30], DB4, and CJCV1 (Harlan Bioproducts for Science). A rabbit polyclonal serum against formalin fixed whole cells of 81-176 has been reported previously [34].

PCR: All PCR products generated for cloning or sequence analysis were amplified using Phusion high fidelity polymerase (New England Biolabs). All other PCRs used Taq polymerase (Applied Biosystems/Life Technologies).

Mutation of CJJ81176_1420: CJJ81176_1420 was cloned into pCRScript using primers pg12.13 and pg12.14 that introduced EcoR and XhoI sites, respectively. This plasmid was subjected to transposon mutagenesis using Tnp Km (kanamycin resistance or aph3; Epicentre) and individual Km$^r$ transposon insertions were sequenced with primers internal to the transposon to determine the site of insertion. A nonpolar transposon insertion at bp 367 of the 1779 bp gene was used to electroporate 81-176 to Km$^r$ using methods previously described. The putative mutation was confirmed by PCR using primers pg12.25 and pg12.26 that bracket the point of insertion of the kanamycin gene and this mutant was called strain 3477.

Mutation of CJJ81176_1435: CJJ81176_1435 was cloned into pCRScript using primers pg10.07 and pg10.08. The chloramphenicol resistance (cat) cassette from pRY109 [35] was cloned into a unique NcoI site located at bp 747 of the 1813 bp gene. Clones were partially sequenced to determine orientation of the cat cassette and one in which the gene was inserted in the same orientation as CJJ81176_1435 was used to electroporate 81-176 to Cm$^r$. Putative clones were confirmed by PCR using pg14.67 and pg14.68 that bracket the NcoI site of insertion, and the resulting mutant was called strain 3636.

Construction of a double mutant in both putative MeOPN transferases: Strain 3477, CJJ81176_1420::aph3, was electroporated to Cm$^r$ with the same plasmid used to generate strain 3636, thus generating a double mutant, strain 3479 (see Table 1).

Construction of a hipO (hippurate) insertion vector. The hipO gene of 81-176 (CJJ81176_1003) was cloned into pCRScript using primer set pg12.31 and pg12.32. A unique XbaI site was introduced in the center of the hipO gene by inverse PCR with primer sets pg12.33 and pg12.34. This plasmid was called pCPE3490.

Construction of strains expressing repaired alleles of CJJ81176_1420 and CJJ81187_1435: The CJJ1420::aph3 mutant was complemented with a repaired allele as follows. The wildtype CJJ81176_1420 gene was PCR amplified using primers pg12.29 and pg12.30, which introduced BamHI and EcoR1 sites, respectively, and the resulting amplicon was cloned into BamHI and EcoRI digested pCPE108. Plasmid pCPE108 contains the σ28 promoter from flaA cloned between the XbaI and BamHI sites of pBluescript [36]. The phase variable G9 tract within CJJ81176_1420 was repaired by Quick Change (Life Technologies) mutagenesis such that the G9 was changed to GGAGGAGGA using primers pg12.37 and pg12.38. The entire insert was moved as an EcoR1-NotI fragment into pBluescript and a SmaI-ended cat cassette from pRY109 [35] was inserted into the EcoRV site 3' to the repaired CJJ81176_1420 gene. The entire construction (σ28-CJJ81176_1420+cat) was PCR amplified with forward and reverse primers and cloned into the unique XbaI site within the hipO gene in pCPE3490 (described above) that had been blunted. This construction was used to electroporate 3477, the CJJ81-176_1420::cat mutant, to Km$^r$, generating strain 3498.

The CJJ1435::cat mutant was complemented by a similar strategy. Plasmid pCPE108 was modified to contain an aph3 gene at the XhoI site in the polylinker, generating pCPE3583. CJJ81176_1435 was PCR amplified using primers pg14.35 and pg14.03, which introduced BamHI and EcoRI sites, respectively, and cloned into BamHI and EcoR1 digested pCPE3583. The phase variable G9 tract located within the coding region of CJJ81176_1435 was subjected to site-directed mutagenesis as described above using primers pg14.09 and pg14.10. The repaired CJJ81176_1435 gene and the adjacent aph3 gene were PCR amplified using forward and reverse primers and cloned into an EcoRV site on a plasmid containing the astA of strain 81-176, as previously described [36, 37]. This plasmid was used to electroporate the CJJ81176_1435 mutant, 3636, to Km$^r$, generating strain 3637.

CPS immunoblots: Whole cells of *C. jejuni* were digested with proteinase K as previously described [30, 34]. Preparations were electrophoresed on 16% Tris-glycine gels (Invitrogen) and stained with silver (BioRad) to visualize the LOS cores. Equivalent core amounts were electrophoresed on 12.5% SDS-PAGE gels and transferred to nitrocellulose. The whole cell anti-81-176 serum was used at a final dilution of 1:500, and the anti-conjugate antisera were used at a final dilution of 1:100. Immunoblots were developed using chemiluminescence (SuperSignal West Femto Maximum Sensitivity Substrate, ThermoFisher) and recorded on a BioRad Gel Imaging System.

NMR analyses: $^{31}$P NMR spectra were recorded using a Bruker AMX 400 spectrometer. 1D 31P and $^1$H-$^{31}$P 2D experiments were performed using Bruker software. Samples were lyophilized with D2O (99.9%) three times prior to recording the spectra. Orthophosphoric acid (δp 0.0) was used as the external reference for all $^{31}$P experiments.

Anti-CPS ELISAs: To determine the anti-CPS response in hyperimmune rabbits Carbo-BIND plates (Corning, Corning, N.Y.) were coated with 100 μl of oxidized CPS from wildtype, 3390, 3477 or 3636 strains (2 μg/ml in sodium acetate buffer (pH 5.5) for 1 hr at room temperature according to the manufacturer's instructions. Plates were washed with 1× PBS-0.05% Tween-20 (PBST), blocked with 5% fetal calf sera in PBST (5% FCS-PBST) for 1 hr at 37° C. and washed again with PBST. All rabbit hyperimmune sera were serially diluted in 5% FCS-PBST in duplicate and incubated for 1.5 hr at 37° C. After washing, HRP-conjugated goat anti-rabbit IgG (Sigma-Aldrich, St. Louis, Mo.) was diluted in 5% FCS-PBST and added at 100 μl per well for 1 hr at 37° C. before washing. 2,2'-azinobis(3-ethylbenzthiazolinesulfonic acid) (ABTS)-peroxidase substrate (KPL, Gaithersburg, Md.) was used as a detection reagent and the OD405 was measured. The mean OD405 of negative control wells (coating buffer alone)+3 standard deviations was used to determine the endpoint titer.

To determine the levels of MeOPN-6-Gal on the three CPS-CRM197 conjugates, the conjugates were normalized based on total CPS content and serially diluted on MaxiSorp Nunc® plates (Sigma-Aldrich, St. Louis, Mo.) in carbonate coating buffer overnight at 4° C. Plates were washed with PBST and blocked with BSA in PBST for 1 hr at 37° C. To detect MeOPN-6-Gal, plates were washed and DB3 monoclonal was diluted in blocking buffer and incubated for 1 hr at 37° C. Goat anti-mouse IgG-HRP (Thermo-Scientific) was added after washing and incubated for 1 hr at 37° C. Plates were washed and 100 μl of tetramethylene benzidine (TMB, eBioscience, San Diego, Calif.) substrate was added for 10 min before 100 μl 1M H$_2$SO$_4$ was added to stop the reaction. The OD was read at 450 nm.

Generation of hybridomas: Splenocytes from BALB/c mice immunized subcutaneously with CPS81-176-CRM$_{197}$ conjugate three times at 4 week intervals, were fused with SP2/O myeloma cells to generate hybridomas according to [38]. Briefly, splenocytes and SP2/O cells were fused in the presence of polyethylene glycol and mixed with peritoneal macrophages derived from a non-immunized BALB/c mouse in hybridoma media [Iscoves media containing 20% FBS, 2× HAT (200 mM hypoxanthine, 0.8 mM aminopterin, 32 mM thymine), OPI (1 mM oxaloacetate, 0.45 mM pyruvate and 0.2 U/mL insulin), 4 mM glutamine and IL-6 (10 ng/ml). Fused cells were immediately plated on eight 96-well cell culture plates and incubated at 37° C. in a 5% CO2 atmosphere for 2 weeks. Hybridomas were selected by screening culture supernatants from each well by ELISA using BSA conjugates of CPS from both 81-176 and the mpnC mutant as antigenic targets.

Production and purification of monoclonal (mAb) DB3: A single cell hybridoma clone was gradually expanded into 16 T-150 flasks, while weaning down to 2.5% FBS in Iscove's media. Cells were transferred into 2 L roller bottles containing 1 L of serum free media (SFM), and were cultured at 37° C. in 5% CO$_2$ for 4 weeks. The mAb DB3 in SFM was purified over a MEP-HyperCel column according to manufacturer's instructions (Pall life Sciences). Eluted antibodies were dialyzed into TBS (0.05 M Tris/0.15 NaCl, pH 7.6), and protein content was determined by BCA assay. Aliquots were stored at 80° C. for further characterization and use. Isotype was determined using an isotyping kit (Pierce).

Dot blot assay: *C. jejuni* cells were set to an OD$_{600}$=0.5 in PBS, pH 7.4, and spotted in triplicate (2 microliters) onto nitrocellulose and allowed to dry. Membranes were immunodetected using mAb DB3 at a final concentration of 10 ug/ml, followed by anti-rabbit goat IgG-HRP (Sigma-Aldrich) and then chemiluminescence detection, as described above.

Complement killing: Pooled normal human sera (NHS) was purchased from Sigma and a single lot was used for all experiments. Assays were done as described in Maue et al. [21], except that a range of NHS was used. Assays were repeated between 2-9 times for each strain. Statistics were done using Graphpad Prism.

Colony blots with anti-conjugate antibody reactivity: Individual colonies of 81-176 were grown for 48 h MH agar plates. Individual colonies were resuspended in PBS and 2 ul was spotted onto nitrocellulose for immunodetection with DB3 antibody at a final dilution of 10 μg/mL.

Flow cytometry: 81-176 strains were grown for 20 hours on MH agar, and the cells were harvested into 5 mL of PBS and filtered through a 1.2 micron filter. The resulting suspension was adjusted to an OD$_{600}$ 0.1, and one ml was spun down at 12000 g for 2 min. Pellets were resuspended in 0.5 ml 4% formaldehyde and incubated on a rotator for 10 min at room temperature. Cells were centrifuged, washed twice in ice-cold PBST, and resuspended in 100 microliters of a 1:50 dilution of serum from hyperimmune rabbits immunized with a conjugate antibody or DB3 monoclonal antibody at a final concentration of 112 μg/ml and incubated for 30 minutes at 4° C. Suspensions were washed twice with ice cold PBST and then incubated with donkey anti-rabbit IgG AlexaFluor 647 (Biolegend, San Diego, Calif.) for the hyperimmune sera or rat anti-mouse IgG1 PE (Southern-Biotech, Birmingham, Ala.), and incubated for 30 minutes at 4° C. The suspensions were washed twice in ice cold PBST and resuspended in 0.5 ml PBST and read on a Canto FACS. Data were analyzed using FlowJo (TreeStar, Ashland, Oreg.).

Vaccines DB4 and CJCV1 were produced by Dalton Pharma, Toronto.

Results

Figure 20:
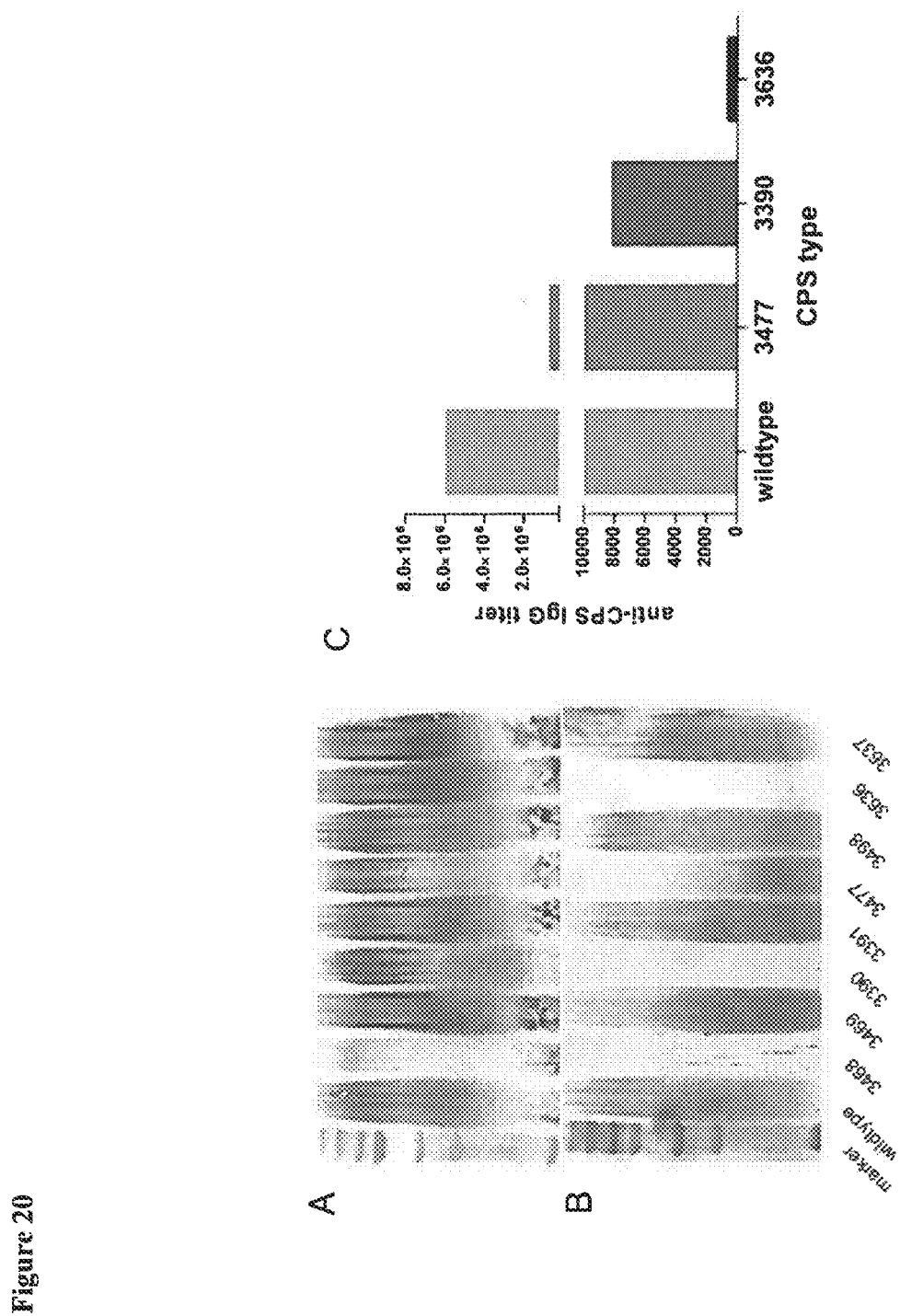
FIG. 20 depicts an immune response of anti-conjugate antibodies. A. Immunoblot with rabbit hyperimmune antiserum to formalin-killed whole cells of C. jejuni 81-176. B. Immunoblot with rabbit hyperimmune antiserum to an 81-176-CRM197 conjugate vaccine (CJCV1). Lanes are: Marker, Precision Plus Protein Standards; wildtype 81-176; strain 3468, a kpsM, non-encapsulated mutant, ([34]); strain 3469, the complement of kpsM, strain 3390, the mpnC mutant lacking the ability to synthesize MeOPN ([21]); strain 3391, the complement of mpnC; strain 3477, the mutant in CJJ81176_1420; strain 3498, the complement of the CJJ81176_1420 mutant; strain 3636, the mutant in CJJ81176_1435; strain 3637, the complement of the CJJ81176_1435 mutant. C. Immune response of anti-conjugate antibodies to purified CPS polysaccharide as measured by ELISA. Strain numbers of the mutants used are indicated and explained in Table 1.

MeOPN is an immunodominant capsular epitope recognized by anti-conjugate antibodies. Proteinase K digested whole cells of *C. jejuni* 81-176 and mutants were immunodetected with rabbit polyclonal antibodies to formalin killed whole cells of 81-176 (FIG. 20A, [34]) and to an 81-176-CRM197 conjugate vaccine, CJCV1 (FIG. 20B). FIG. 20A shows that the whole cell antiserum reacted with the wild-type capsule, but not an unencapsulated mutant, kpsM, strain 3468 [34]. When kpsM was complemented in trans (strain 3469) [34], reactivity was restored. FIG. 20A also shows that the whole cell serum reacted with the mpnC mutant (strain 3390) that expresses CPS lacking MeOPN, and its complement, strain 3391 [21]. In comparison, the rabbit polyclonal serum to the CPS conjugate vaccine, (CJCV1; FIG. 2B) reacted with wildtype 81-176, but did not react with either the CPS-void kpsM mutant or the MeOPN-void mpnC mutant. Reactivity was restored when both mutants were complemented (strains 3469 and 3391, respectively). Similar reactivity was seen with rabbit polyclonal antisera to two other batches of 81-176-CRM197 conjugate vaccines.

Reactivity of anti-conjugate antiserum to mutants of each MeOPN transferase. Strain 81-176 contains two putative MeOPN transferase genes, CJJ81176_1420 and CJJ81176_1435 (FIG. 19B). We generated mutations in each gene as described in Materials and Methods, and we compared the ability of antibodies generated to 81-176-CRM$_{197}$ conjugate vaccines to react with mutants in each of the MeOPN transferase genes. FIG. 20A shows that the antiserum to whole cells of 81-176 reacted with proteinase K digested whole cells of both putative transferase mutants, 3477 and 3636, confirming expression of polysaccharide CPS. There was a distinct difference between the reactivities of the anti-whole cell serum and the anti-conjugate serum against the CPS preparation from strain 3477, the CJJ81176_1420 mutant. In the case of the anti-conjugate serum (FIG. 20B), a reaction could only be seen with CPS material of apparent low mass, whereas with whole-cell sera (FIG. 20A) a broader reactivity was observed. The intensity and pattern of the reaction with anti-conjugate sera was restored in the complement, 3498 (FIG. 20B). The antiserum against whole cells reacted with CPS from 3636 (FIG. 20A) and the complement. However, there was no detectable reaction between the anti-conjugate serum and CPS from 3636, the mutant in CJJ81176_1435 (FIG. 20B). Reactivity with anti-conjugate serum was restored in the complement, strain 3637 (FIG. 20B).

Similar results were observed with additional rabbit antisera to two other batches of conjugate vaccines. Collectively, these data indicated that while antibodies generated against formalin-killed whole cells of 81-176 reacted with the polysaccharide chain, antibodies generated against the conjugates were directed primarily to MeOPN-6-Gal and to a lesser extent MeOPN-2-Gal.

The immunodominance of MeOPN in the conjugates was also examined by ELISA. Anti-CJCV1 antibodies were serially diluted and reacted to CPS from wildtype 81-176 or mutants. The results, shown in FIG. 20C, indicated that the reaction of CJCV1 was strongest to the wildtype CPS (titer: 5.9×10$^6$). There was a reaction to CPS purified from 3477, the mutant in CJJ81176_1420, with an endpoint titer lower than wildtype (titer: 6.6×10$^5$). Reaction of CJCV1 sera was reduced to the CPS from both 3636, the mutant in CJJ81176_1435 and to 3390 (mpnC) that lacks all MeOPN (titers: 600 and 8100, respectively). Based on the stronger reactivity of anti-conjugate antibodies to synthetic MeOPN-6-Gal than to MeOPN-2-Gal reported herein, it is likely that the CJJ81176_1435 transferase is responsible for addition of MeOPN to the 6 position of Gal and that the transferase encoded by CJJ81176_1420 is responsible for addition of MeOPN to the 2-position of Gal. This was further studied by NMR, below.

MeOPN modifications on the 81-176 CPS. Previously, using mass spectrometry we detected a non stoichiometric MeOPN unit at the 2 position of galactose (MeOPN-2-Gal) in 81-176 CPS ([31]), with a $^{31}$P resonance similar to that in FIG. 21A (peak Y). Here, we confirmed this MeOPN-2-Gal linkage by NMR (FIG. 22A) through the detection of a cross-peak between the $^{31}$P resonance Y ($\delta_P$ 14.45) of MeOPN and H-2 ($\delta_H$ 4.52) of the galactose unit in a $^1$H-$^{31}$P correlation experiment.

In some 81-176 CPS preparations, albeit of lower intensity, the $^{31}$P NMR spectrum displayed an additional resonance (FIG. 21B) at $\delta_P$ 14.15 (designated peak Z). A similar peak was also observed in the 31P NMR of mutant in CJJ81176_1420, called 3477, which exhibited a cross-peak (FIG. 22B) between the phosphorus of MeOPN and H-6 resonances of some of the CPS galactose units, which resonated very near the methyl resonances of MeOPN ($\delta_H$ 3.75 to 3.81). No significant peak Y was Observed in CPS from 3477. The NMR data suggested that peak Z in 81-176 and 3477 (the mutant in CJJ81176_1420) corresponded to a non-stoichiometric placement of MeOPN at position 6 of galactose (MeOPN-6-Gal), consistent with the data using synthetic MeOPN-6-Gal described herein.

The $^{31}$P NMR spectrum of 3636 (FIG. 21C), mutant in CJJ81176_1435, did not show either peak Y or peak Z, but yielded a previously unseen phosphorus resonance at $\delta_P$ 14.79 (designated peak X). A 2D $^1$H-$^{31}$P NMR experiment showed a connection between peak X and a proton resonance at $\delta_H$ 4.85 (FIG. 22C). The NMR data of the CPS from strain 3636 implied a new activity in the mutant in CJJ81176_1435 that afforded a MeOPN modification not previously observed in 81-176 CPS. This new CPS modification is the subject of an on-going study.

The $^{31}$P NMR spectrum of a mutant in both transferases (strain 3479) showed no MeOPN-related resonances (data not shown).

Figure 23:
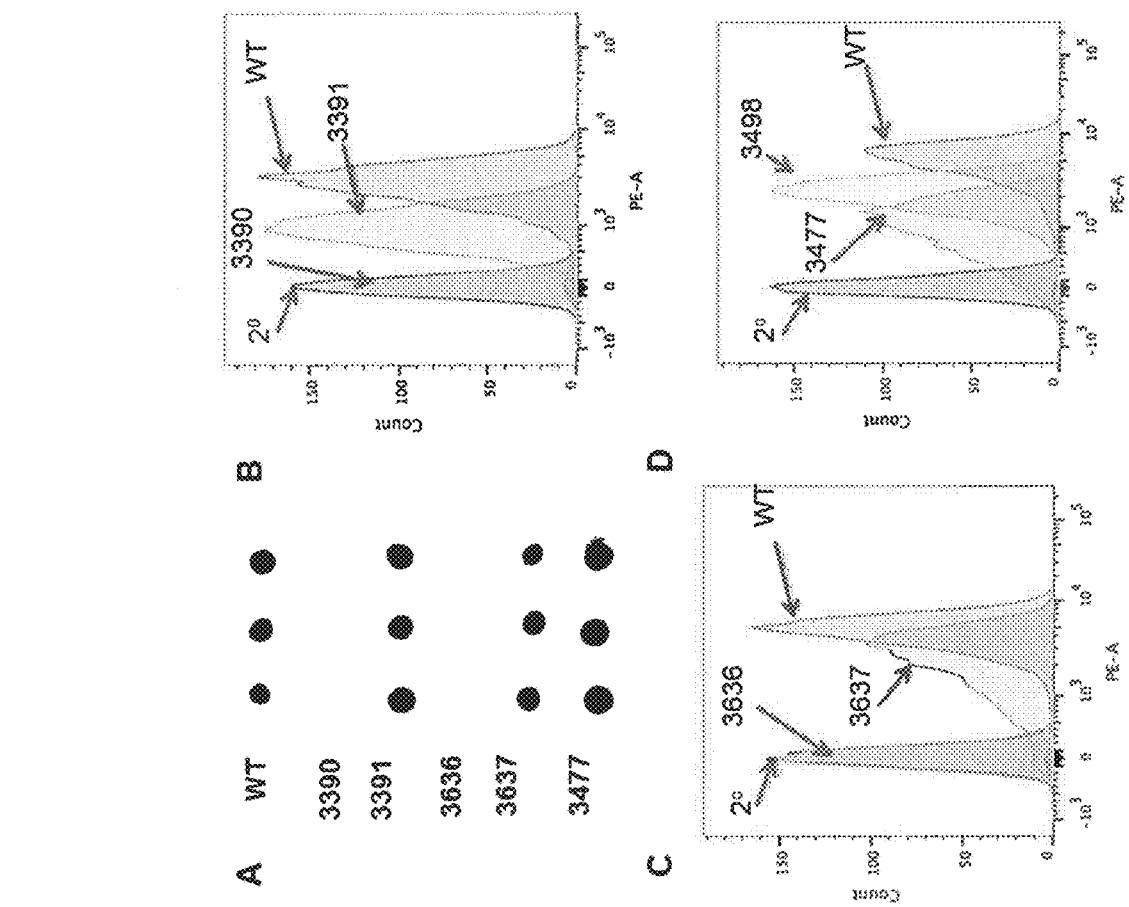
FIG. 23 depicts the characterization of monoclonal DB3. A. Dot blot of whole cells of wildtype 81-176 and various mutants detected with DB3. B. Flow cytometry of wildtype, 3390, and 3391 with DB3. C. Flow cytometry of wildtype, 3636 and 3637 with DB3, D. Flow cytometry of wildtype, 3477, and 3498 with DB3. The peak labeled "2°" in B, C and D shows binding of the secondary antibody alone.

Monoclonal DB3. A mouse monoclonal antibody (isotype IgG1) was isolated from an animal immunized with an 81-176-CRM197 conjugate vaccine. The monoclonal was used in a dot blot with whole cells of wildtype 81-176 and various mutants, as shown in FIG. 23A. The monoclonal did not react with either the mpnC mutant (3390) or the 81176_CJJ1435 mutant (3636), but reactivity was restored when both mutants were complemented (3391 and 3637, respectively). Since DB3 bound to the 81176_CJJ1420 mutant (3477), the specificity of the monoclonal was for the site modified by the transferase encoded by CJJ81176_1435, which is likely MeOPN-6-Gal. Additionally, DB3 failed to react to other MeOPN-containing capsules (HS1, HS2, HS3, HS4, and HS15) [39-44], again confirming the specificity was not to MeOPN alone, but included the sugar linkage (data not shown).

Flow cytometry analyses using DB3. FIG. 23B shows that monoclonal DB3 bound to the surface of wildtype 81-176 as measured by flow cytometry, but did not bind to the mpnC mutant, as expected from the dot blotting studies. Binding was partially restored in strain 3391, the complement of the mpnC mutant. Similarly, DB3 did not bind to 3636, the mutant presumably lacking MeOPN-6-Gal, and binding was partially restored in 3637, the complement (FIG. 23C). However, DB3 binding to 3477, the mutant lacking MeOPN-2-Gal, but retaining MeOPN-6-Gal, was reduced. Binding was enhanced in strain 3498, the complement (FIG. 23D).

Figure 24:
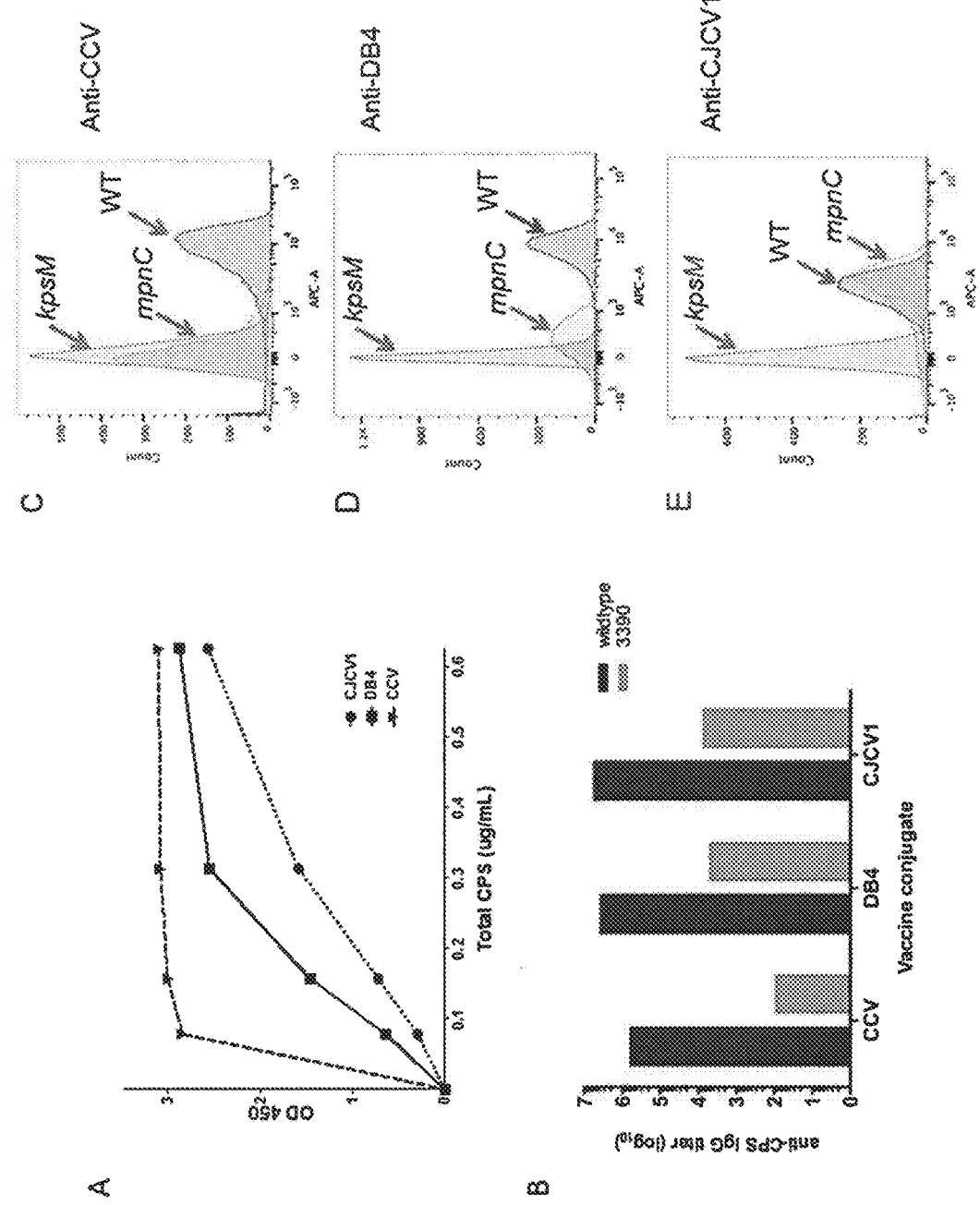
FIG. 24 depicts the variation of MeOPN levels of different batches of conjugate vaccines. A. DB3 ELISA of three different batches of 81-176-CRM197 conjugate vaccines. B. Endpoint titers of rabbit polyclonal hyperimmune sera to capsules purified from wildtype 81-176 (black bars) and the mpnC mutant (3390; gray bars). C-E, Flow cytometry comparing binding of rabbit hyperimmune serum against conjugate CCV (C), DB4 (D) and CJCV1, (E) to wildtype 81-176, 3390, the mpnC mutant and 3469, the kpsM mutant.

Levels of MeOPN-6-Gal on conjugate vaccines modulate the immune response. When DB3 was used in an ELISA to measure the levels of MeOPN-6-Gal on three independently produced conjugate vaccines, differences in binding could be detected (FIG. 24A). CCV, the vaccine shown to protect non-human primates against diarrheal disease [30], showed the highest binding, DB4 was intermediate, and CJCV1 showed the lowest. Endpoint titers were determined by ELISA to capsules purified from wildtype 81-176 and the mpnC mutant for rabbit hyperimmune antisera against each of the three vaccines, as shown in FIG. 24B. Each vaccine elicited high titers of antibodies to the intact wildtype capsule (CCV: $6.6 \times 10^5$, DB4: $4.0 \times 10^6$, CJCV1: $5.9 \times 10^6$), but the titers against the mpnC capsule increased as the amount of MeOPN-6-Gal on each vaccine decreased (CCV: 100, DB4: 5400, CJCV1: 8100). Thus, the anti-polysaccharide response was lowest for CCV, intermediate for DB4 and highest for CJCV1. FIG. 24C-E shows the reactivity of each rabbit hyperimmune sera to the surface of wildtype and the mpnC mutant. CCV, with the highest amount of MeOPN-6-Gal, hound to the surface of wildtype 81-176 and no binding was detected to the mpnC mutant, 3390 (FIG. 24C). Binding was enhanced in the complement, strain 3391. Antibodies to conjugate DB4 bound to the surface of wildtype 81-176 and showed enhanced binding to the mpnC mutant compared to CCV (FIG. 24D). Finally, antibodies to CJCV1 bound equally well to wildtype and the mpnC mutant (FIG. 24E). None of the antibodies bound to the kpsM mutant. Thus, surface binding to the mpnC mutant was enhanced as the levels of MeOPN-6-Gal were reduced in the vaccines.

Figure 25:
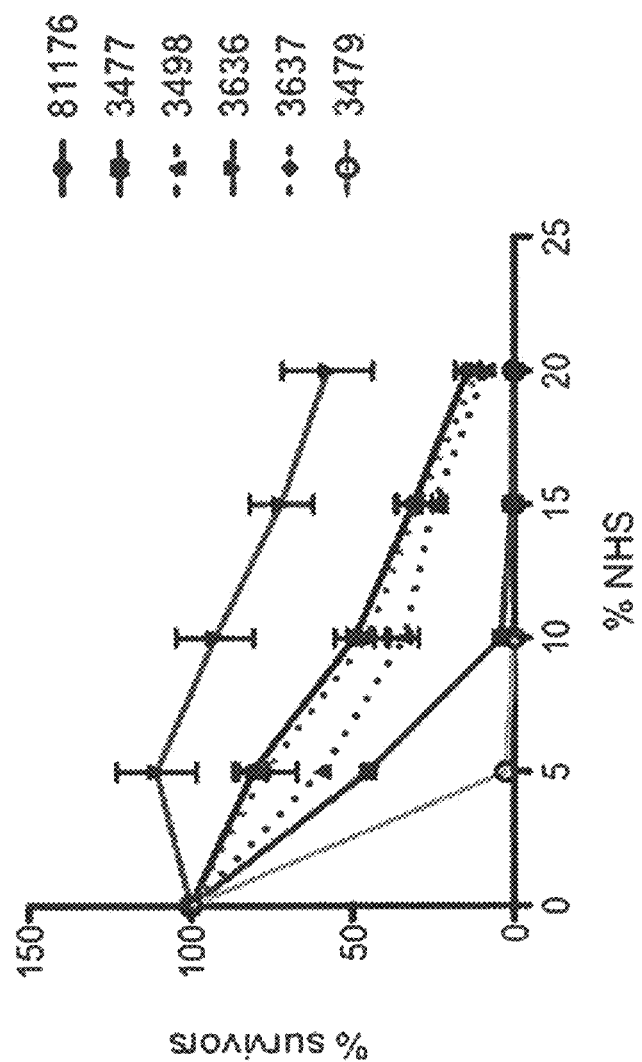
FIG. 25 depicts the resistance of C. jejuni strains to increasing amounts of NHS. Bacteria were exposed to increasing amounts of NHS for 1 h at 37° C. and survivors enumerated by plate counts. Genotypes of the strains are shown in Table 1. Strain 3636 was significantly different from wildtype at all four concentration of NHS ($P<0.05$). Strain 3477 was significantly less serum resistant than wildtype at 5% NHS ($P<0.05$), 10% ($P<0.005$) and 15% ($P<0.05$). There was no significant difference in the complements of the two mutants, 3498 and 3637, with wildtype at any concentration of NHS. The double transferase mutant, 3479, was significantly lower than wildtype at 5% ($P<0.0005$), 10% ($P<0.005$), and 15% NHS ($P<0.05$).

Role of MeOPN in complement resistance. Van Alphen et al. [22, 31] constructed a double mutant in both putative transferase genes and showed that the resulting mutant was sensitive to complement killing, consistent with previous work using the mpnC mutant [21, 22]. We compared serum resistance of 3477, the mutant in CJJ81176_1420, and 3636, the mutant in CJJ81176_1435, and a double mutant lacking both transferases, 3479 (see Table 1) using increasing amounts of NHS. The results, shown in FIG. 25, indicated that at all concentrations of sera, the CJJ81176_1435 mutant, 3636, was significantly more resistant than wildtype, and that the CJJ81176_1420 mutant, 3477, was significantly more sensitive than wildtype 81-176 at concentrations of NHS ranging from 5-15%. When both mutants were complemented with repaired alleles, the levels of serum resistance returned to levels that were not significantly different to that of wildtype. However, mutation of both MeOPN transferases (strain 3479) resulted in enhanced sensitivity over the CJJ81176_1420 mutant (3477), and showed levels of sensitivity similar to that reported previously for another double transferase mutant [22] and for the mpnC mutant [21].

Figure 26:
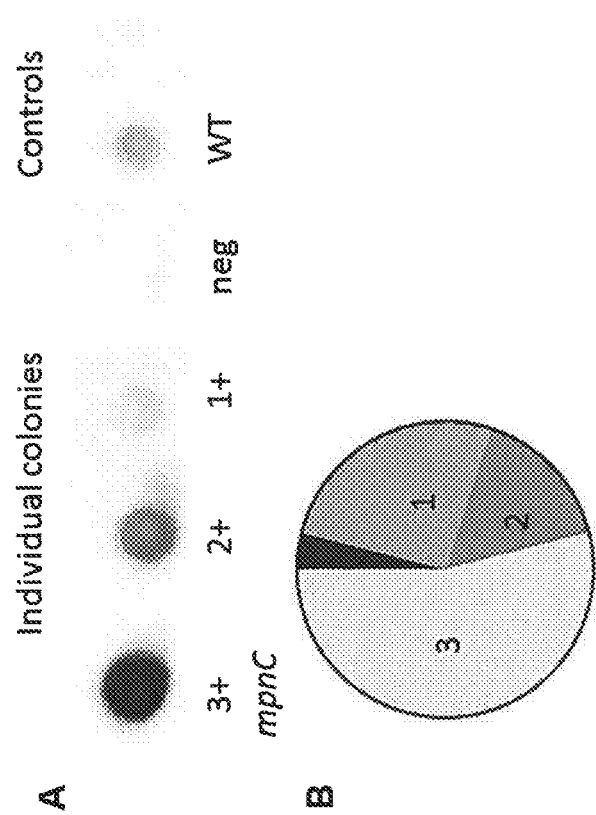
FIG. 26 depicts the phase variation of the CJJ81176_1435 MeOPN transferase. A. Immunoblot of representative single colonies of 81-176 with DB3. The intensity of reactivity is shown by the numerical scoring (3+, 2+, 1+ and negative). WT, the reaction of the population of wildtype 81-176; the negative control is the population of the mpnC mutant, 3390, B. The percentage of colonies within the population showing differing levels of reactivity with DB3. The percentage of colonies that scored as 1+, 2+ and 3+ are shown; the area in black represents colonies that were negative.

Phase variation of MeOPN-6-Gal. Strain 81-176 was plated for single colonies on MH agar and 60 individual colonies were dot blotted with the DB3 monoclonal antibody to measure levels of expression of MeOPN-6-Gal. The results indicated that there was considerable heterogeneity in expression of MeOPN-6-Gal within the population, as shown by the representative colonies in FIG. 26A. Colonies were scored subjectively for intensity, as shown in the figure. Interestingly, the population, labeled as "WT" in FIG. 26A, bound less antibody than most of the single colonies, which is a reflection of the heterogeneity of the population. Collectively, as shown in FIG. 26B, 54% of the single colonies were scored as "3+", 16% as "2+", 26% as "1+" and 4% were negative.

Discussion

Approximately 75% of C. jejuni strains contain genes encoding MeOPN in their CPS locus, but the sugar modified and the sites of modification have been determined in a limited number of CPS types. Most strains contain a single MeOPN transferase, but some, including NCTC 11168 and 81476, contain two transferases and both capsules are modified at two sites [31, 40,] and as disclosed herein. In the presence of both MeOPN transferases in wildtype 81-176, MeOPN is attached to both the 2 and 6 positions of Gal. When CJJ81176_1420 was mutated, MeOPN was attached only to the 6 position, presumably by the MeOPN transferase encoded by CJJ81176_1435. This also indicates that the transferase encoded by CJJ81176_1420 is responsible for addition of MeOPN to 2-Gal. However, when CJJ81176_1435 was mutated, no MeOPN was detected at either the 2 or 6 position of Gal, and there was a new site of attachment at an unknown position. This attachment must be mediated by the transferase encoded by CJJ81176_1420, since the new attachment (peak X in FIG. 21C) was not observed in the double MeOPN transferase mutant 3479. This suggests that the enzyme encoded by CJJ81176_1420 has a relaxed specificity that is dependent on the secondary structure of the polysaccharide chain. Additional studies on the specificities of MeOPN transferases are ongoing in our laboratories.

The MeOPN modifications on the 81-176 CPS are immunodominant in conjugate vaccines, and the response to MeOPN-6-Gal was stronger than that to MeOPN-2-Gal. This is also consistent with the observed reactivity of anti-conjugate antibodies with synthetic MeOPN-6-Gal described herein. The immunodominance of MeOPN-6-Gal may be due to higher levels of this modification on the CPS or it may be that modification on the 6-position of Gal, which is on a primary hydroxyl, is more immunogenic. No antibodies to the polysaccharide chain of the mpnC mutant can be detected by immunoblotting of crude CPS preparations using any of the rabbit hyperimmune sera to conjugate vaccines, although varying levels of anti-polysaccharide antibodies could be detected by the more sensitive techniques of ELISA and flow cytometry. However, the levels of reactivity to the polysaccharide chain increased as the levels of MeOPN-6-Gal decreased, as measured by DB3 binding. In contrast to the response to conjugate vaccines, rabbit hyperimmune serum made against formalin-killed whole cells of 81-176 reacted with the mpnC polysaccharide by immunoblotting. It may be that the cells used as antigen to generate this antiserum expressed less MeOPN than other preparations, or that some MeOPN was lost upon formalin treatment, and thus the cells contained more exposed polysaccharide.

Monoclonal DB3 appears to be specific for the MeOPN-6-Gal epitope as determined by whole cell dot blot, and, consistent with this, bound to the surface of wildtype 81-176, but not to the CJJ81176_1435 or mpnC mutants by flow cytometry. Interestingly, surface binding of DB3 was disrupted by mutation of CJJ81176_1420, suggesting that loss of MeOPN-2-Gal alters the secondary and/or tertiary structure of the CPS and reduces accessibility of DB3 to the surface of the cell. Although no studies have been reported, it is likely that the polysaccharide chain is decorated with MeOPN as it is being synthesized in the cytoplasm. Decoration of sugars with MeOPN is likely to affect changes in folding of the polysaccharide, which, after assembly on the cell surface, could also affect interactions between adjacent polysaccharide chains, thus affecting accessibility of the polysaccharide to antibodies and/or components of the complement cascade. This is consistent with our observations that loss of MeOPN-2-Gal in the CJJ81176_1420 mutant resulted in a significant reduction in resistance to complement mediated killing.

In contrast to the mutation of CJJ81176_1420, mutation of CJJ81176_1435 resulted in enhanced resistance to complement-mediated killing. The $^{31}$P-NMR studies indicated that the CJJ81176_1435 mutant lost both MeOPN-2-

Gal and MeOPN-6-Gal and had gained a new MeOPN modification at an undetermined site. Presumably, this new site of modification provides enhanced protection from the complement cascade. This hypothesis is consistent with the lower endpoint titer seen for the CJJ81176_1435 mutant (3636) compared to the mpnC mutant. Thus, the new MeOPN modification may block accessibility of the anti-CJCV1 antibody to the polysaccharide chain.

Additional studies will be needed to understand the mechanism of these differential sensitivities to complement-mediated killing. However, immunoblotting of individual colonies of wildtype 81-176 with the DB3 monoclonal revealed extensive heterogeneity of MeOPN-6-Gal levels within the population and this, in turn, would suggest that the population can readily adapt to changing environments. Similarly, MeOPN has been shown to be required for binding of several phages, and the ability to vary levels of MeOPN could be critical for survival in several environments [26, 27]. Thus, PV appears to provide a novel mechanism to adjust to these environmental changes, and perhaps to others encountered by this zoonotic pathogen. Similar heterogeneity has been observed not only in surface antigens of C. jejuni [12-17, 34, 46], but also in purine biosynthetic genes that affect the stress response [47, 48]. Collectively, these data support the notion that C. jejuni is a quasi-species that survives by selection of a subset of pre-existing variants within a heterogenous population [47].

The immunodominance of MeOPN in conjugate vaccines appears to be comparable to the immunodominance of O-acetyl groups on the polysaccharide conjugates based on other bacterial pathogens [49-51]. Importantly, there was no detectable reaction of the anti-conjugate sera with CPSs from other serotypes that express MeOPN on different sugars (data not shown), suggesting that the reaction is specific to the Gal linkages found in 81-176, and not to MeOPN per se. Non-stoichiometric modifications to sugars confer considerable heterogeneity to polysaccharide chains and can affect immunogenicity [40, 52]. These data suggest that CPS-based vaccines against C. jejuni might be improved by exploiting this immunodominance of MeOPN-modified sugars. It is contemplated herein that one approach would be to use strains that overexpress the immunodominant epitope for capsule purification and vaccine production. Another alternative approach would be chemical synthesis of the MeOPN-sugar epitopes and conjugation to a carrier protein such as contemplated herein.

Complement mediated killing of C. jejuni has been reported to occur primarily by the classical pathway [22, 53], and the CPS likely functions to shield the cell from naturally occurring antibodies in NHS that cross-react with surface proteins. However, the MeOPN decorations may shield surface proteins and the polysaccharide from cross-reactive antibodies. This is consistent with an earlier observation that NHS contains low levels of antibodies that cross-react with surface proteins of C. jejuni and could induce low levels of complement mediated killing of multiple strains, but that, within 48 h of infection with C. jejuni, patients developed higher-level serum bactericidal titers that were strain specific [53], an observation that may relate to CPS-specific antibody responses. Conjugate vaccines against several other gram-negative pathogens induce bactericidal antibodies that correlate with protection [54-56], and we are exploring this possibility for C. jejuni conjugate vaccines. Although C. jejuni is generally considered to be relatively serum sensitive [57], we have shown here that the organism has the ability to modulate its levels of resistance via PV of the genes encoding the MeOPN transferases, and that the population is composed of cells expressing various levels of these modifications. Thus, the levels of serum resistance measure in vitro for a population may not reflect the levels of resistance that can be achieved in vivo.

Thus, based on the foregoing data, we have demonstrated that the polysaccharide capsule of Campylobacter jejuni strain 81-176 is decorated non-stoichiometrically with methyl phosphoramidate (MeOPN) at the 2 (MeOPN-2-Gal) and 6 positions of galactose (MeOPN-6-Gal), and these are the immunodominant epitopes recognized by antibodies to 81-176 capsule conjugate vaccines. A mouse monoclonal antibody specific for MeOPN-6-Gal bound to the surface of wildtype 81-176, but binding to a mutant lacking MeOPN-2-Gal was reduced, suggesting that loss of MeOPN-2-Gal effects changes in capsule secondary/tertiary structure. Using the MeOPN-6-Gal-specific monoclonal antibody we have shown that the population consists of a heterogenous mixture of cells expressing different levels of MeOPN-6-Gal as a result of phase variation of the MeOPN transferase. A mutant in the MeOPN transferase encoded by CJJ81176_1420, which appears to be responsible for attachment of MeOPN-2-Gal, was significantly more sensitive to complement-mediated killing than wildtype at 5, 10 and 15% normal human serum (NHS). In contrast, the mutant in CJJ81176_1435, the transferase that appears responsible for addition of MeOPN-6-Gal, was significantly more resistant than wildtype at 5, 10, 15 and 20% NHS. In the CJJ81176_1435 mutant, both MeOPN-6-Gal and MeOPN-2-Gal were lost and a new, unidentified site of MeOPN modification was observed that was likely responsible for the enhanced serum resistance in this mutant. Thus, it appears that in the absence of the transferase encoded by CJJ81176_1435, the CJJ81176_1420 transferase was able to modify a secondary site on the capsule. Thus, phase variation of the MeOPN transferases modulates the structure of the capsule and the levels of resistance to complement-mediated killing.

REFERENCES FOR EXAMPLE 8

1. Epps, S V R et al. 2013 Int. S. Environ Res. Public Health 10:6292-6304.
2. Coker, A O et al. 2002 Emerg. Infect. Dis. 8:237-244.
3. Oberhelman, R and Taylor, D N 2000 *Campylobacter* infections in developing countries, pp 139-154. In: I. Nachamkin and M. J. Blaser, *Campylobacter,* 2nd ed., pp. 139-154, ASM Press, Washington, D.C.
4. Kotloff, K L et al. 2013 Lancet 382: 209-222.
5. Platts-Mills, J et al. 2015 Lancet Glob Health 3(9):e564-567. Doi: 10.1016/S2214-109X (15)00151-5.
6. Lee G, et al. 2013 PLOS Neglected Tropical Dis. 7:e2036. Doi:10.13711journal.pntd.002036.
7. Nachamkin, I et al. 2000 *Campylobacter jejuni* infection and the association with Guillain-Barre syndrome. In I. Nachamkin and M. J. Blaser (ed.), *Campylobacter,* 2nd ed. ASM Press, Washington, D.C.
8. Molbak, K and Havelaar, A. Burden of illness of Campylobacteriosis and sequelae. In: I. Nachamkin, Christine Szymanski and M. J. Blaser (ed.), 2008, *Campylobacter*, third edition. (American Society for Microbiology, Washington, D.C.).
9. Karlyshev, A V et al. 2000. Mol. Microbiol. 35:529-541.
10. Penner, J L and Hennesey, J N H 1980 J. Clin. Microbiol. 12:732-737.
11. Guerry, P et al. 2012 Fronteirs Microbiol. 2: article 7. doi: 10.3389/fcimb.2012.00007.
12. Parkhill, J et al. 2000 Nature 403:665-668.

13. Linton, D et al. 2000 Mol. Microbiol. 37:501-514.
14. Guerry, P et al. 2001. Infect. Immun. 70:787-793.
15. Hendrixson, D R 2006. Mol. Microbiol. 61:1646-1659.
16. Thomas, D K et al. 2014 Plos One 9:e88229. Doi: 10.1371/journal.pone.0088229.
17. Jerome, J P et al. 2011 Plos One 6:e16399. doi:10.1371/journal.pone.0016399.
18. Gaasbeek, E J et al. 2009 J. Bacteriol. 191:3785-3793.
19. Bachtiar, B M et al. 2007 FEMS Immunol. Med. Microbiol. 49:149-154.
20. Grant, A J et al. 2005 Appl. Environ. Microbiol. 71:8031-8041.
21. Maue, A C et al. 2013 Infect Immun. 81:665-672.
22. van Alphen L B, et al. 2014 Plos One, 2014. 9:e87051. Doi: 10.1371/journal.pone.0087051.
23. Champion, O L et al. 2010 J. Infect. Dis. 201: 776-782.
24. Rose, A et al. 2011 Med. Microbiol. Immunol. 201:137-144.
25. Stahl, M et al. 2014 PLOS Pathog., 10(7):e1004264. Doi:10.1371/journal.ppat.1004264.
26. Sorensen, M C H et al. 2012 J. Bacteriol. 193:6742-6749.
27. Sorensen, M C H et al. Fronteirs Cell Infect Microbiol. 2:11. Doi:10.3389/fcimb.2012.00011.
28. Lesinski, G B and Westerink, M A. 2001 Curr Drug Targets Disord 1:325-334.
29. Knuf, M et al. 2011 Vaccine 29:4881-4890.
30. Monteiro, M A et al. 2009 Infect. Immun.77:1128-1136.
31. Kanipes, M I et al. 2006 J. Bacteriol. 188:3273-3279.
34. Bacon, D J et al. 2001 Mol. Microbiol. 40:769-777.
35. Yao, R. et al. 1993 Gene 130:127-130.
36. Ewing, C P et al. 2009. J. Bacteriol. 191:7086-7093.
37. Yao, R. and Guerry, P. 1996 J. Bacteriol. 178:3335-3338.
38. Nyame, A K et al. 2003 Exp. Parasitol. 104:1-13.
39. McNally, D. et al. 2005 FEBS J. 272:4407-4422.
40. McNally, D J et al. 2007 J. Biol. Chem. 282: 28566-28576.
41. Karlyshev, A V et al. 2005 Mol. Microbiol. 55:90-103.
42. Aspinall, G O et al. 1995 Eur J. Biochem. 231:570-578.
43. Bertalo, L et al. 2013 Carbohy. Res. 366:45-49.
44. Chen, Y H et al. 2008 Carbohydr. Res. 343:1034-1040.
46. Mohawk, K L et al. 2014 Plos One, 9(e88043.). doi: 10.1371/journal/pone.008043.
47. Cameron, A et al. 2015 mBio 6(5):e00612-15. Doi: 10.1128/mBio.00612-15.
48. Cameron, A et al. 2012 J. Bacteriol. 194:6116-6130.
49. Calix, J. et al. 2011 J. Bacteriol. 193:5271-5278.
50. Szu, S C et al. 1991 Infect Immun. 59:4555-4561.
51. Fattom, A I et al. 1998 Infect. Immun. 66:4588-4592.
52. King, M R et al. 2007 Trends Microbiol. 15:196-202.
53. Pennie, R A, et al. 1986 Infect. Immun. 52:702-106.
54. Gill, C J et al. 2011 Vaccine 30:29-34.
55. Townsend, K et al. 2014 Vaccine 32:5650-5660.
56. Bash, M C et al. 2014 Clin. Vaccine Immunol. 21:755-761.
57. Blaser, M J et al. 1985 J. Infect Dis. 151:227-235.

Example 9

Prophetic Method of Inducing an Immune Response Against *C. jejuni* in a Subject The immunogenic synthetic constructs described in the proceeding examples can be included in an immunogenic formulation (e.g., a vaccine formulation) against *C. jejuni* and administered to a subject for inducing an immune response against *C. jejuni*. Thus, the present example is a prophetic method for the induction of an immune response to *C. jejuni* in a subject, and particularly, a method of inducing an immune response in a subject that provides protective immunity from the gastrointestinal and other debilitating effects associated with *campylobacter* enteritis, is contemplated herein.

As an example, such method could comprise administering an immunogenic composition comprising one or more synthetic constructs of the instant invention, wherein the construct is optionally conjugated to a carrier molecule, preferably to a carrier protein molecule such as $CRM_{197}$. The method may further comprise one or more subsequent steps comprising administering one or more boosting doses of a composition comprising the same immunogen administered in the first step.

As understood by one of skill in the art, optimal methods for inducing protective immunity in humans are preceded by studies in animals such as in mice and monkeys. For each vaccine formulation comprising a synthetic construct of the instant invention, a limited amount of experimentation is required to ascertain the optimal effective dose ranges. For example, in one embodiment, it is contemplated herein that the range of a unit dose of immunogenic synthetic construct may be from about 0.1 µg to 10 mg per dose in a range of buffer solutions. Optionally, subsequent to a priming dose, one or more, e.g., 2 to 4 boosting doses may also be administered with a unit dose range of from about 0.1 µg to 10 mg of immunogen in a buffered aqueous solution.

Thus, a method of inducing an immune response in a subject against *C. jejuni* may comprise the steps of: (a.) administering an immunogenic composition comprising one or more synthetic constructs of the instant invention, wherein the construct is conjugated to a carrier molecule, preferably to a carrier protein molecule, and the composition administered at a dose range of 0.1 µg to 10 mg per dose with or without an adjuvant; and (b) optionally administering a boosting dose of the composition as described in step (a), with or without adjuvant, at a dose range of 0.1 µg to 10 mg per dose.

It is contemplated herein that depending on the route of administration, the vaccine formulation can be administered with or without any of a number of adjuvants such as those described in detail above.

Moreover, as discussed hereinabove, the method may be performed using a synthetic construct that is conjugated to a carrier protein or using an unconjugated synthetic construct. The method may comprise the use of any of a number of carrier molecules discussed above. As an example, $CRM_{197}$ can be used. ETEC proteins may also be used as carrier proteins as discussed above, e.g., as disclosed in US 2015/0258201 A1.

The construct:carrier protein ratio (w/w) may be 1:1, or may be such that more than one construct is linked to a single carrier protein, e.g., from 2:1 to 10:1 or more; particularly, at least 8:1. As one of skill in the art will appreciate, a single carrier molecule may be conjugated to a large number of synthetic constructs, e.g., hundreds or even thousands of constructs per carrier molecule. An appropriate ratio best suited to inducing and/or enhancing an immune response in a subject may be discerned by one of skill in the art without undue experimentation.

Indeed, as contemplated herein, one of skill in the art could optimize the immunogenicity of a synthetic construct for use in the methods of the instant invention by using different combinations of synthetic constructs, including constructs and conjugates comprising more than one MeOPN modified monosaccharide, adjuvants, carrier proteins, additional immunoregulatory agents, and routes of administration. For example, it is contemplated herein that different ETEC proteins may be used in various combinations with the immunogenic synthetic constructs of the instant invention to produce a construct with enhanced immunogenicity, not only to C. jejuni but also to other bacterial pathogens. To this end, the teachings of US2015/0258201 A1 are incorporated by reference herein in its entirety. Moreover, a composition of the instant invention, e.g., pharmaceutical formulations, and particularly vaccine formulations of the instant invention can be administered orally, nasally, subcutaneously, intradermally, transdermally, transcutaneously intramuscularly, or rectally. Methods of administration and dosing regimens best suited to producing an immune response in a subject may be discerned by one of skill in the art using conventional methods and without undue experimentation.

Example 10

Multivalent Vaccine Formulations Against C. jejuni or Other Organisms

Data provided herein demonstrate that antibodies to HS23/36, HS4 and HS1 strains of C. jejuni can react with a synthetic MeOPN-6-Gal construct. Thus, in one embodiment, it is contemplated herein that one of skill in the art, using conventional methods and without undue experimentation, could develop a multivalent vaccine formulation comprising the synthetic MeOPN-6 Gal construct disclosed herein which should cover at least these three major capsule types of C. jejuni.

It is further contemplated herein that additional multivalent formulations comprising one or more immunogenic synthetic constructs of the instant invention could be developed which cover the strains of C. jejuni which account for a majority of worldwide cases of campylobacteriosis. Such formulations might be produced, for example, by synthesizing additional constructs comprising capsular monosaccharides from C. jejuni strains of relevance in this regard and testing such synthetic constructs for immunogenicity (including possible cross reactivity) against such strains of C. jejuni. In a particular embodiment, such synthetic constructs may comprise one or more monosaccharides comprising one or more MeOPN moieties including, e.g., one or more MeOPN-6-Gal moieties and/or one or more MeOPN-2-Gal moieties. A synthetic construct comprising MeOPN-2-Gal is contemplated herein.

A multivalent vaccine formulation of the instant invention may comprise a single synthetic construct designed to cover more than one strain of C. jejuni, and/or may comprise a synthetic construct designed specifically against a single particular strain of C. jejuni. In addition, one of skill in the art will appreciate that synthetic constructs may be produced which are immunogenic not only against more than one strain of C. jejuni, but also against more than one type of bacterium, e.g., ETEC or Shigella, by chemically linking various different antigenic components against these additional bacteria to an immunogenic construct against C. jejuni. See, e.g., US 2015/0258201.

Having described the invention, one of skill in the art will appreciate that many modifications and variations of the present invention are possible in light of the above teachings. It is therefore, to be understood that, within the scope of the appended claims, the invention may be practiced otherwise than as specifically described.

What is claimed is:

1. An immunogenic synthetic construct capable of inducing an immune response against *Campylobacter jejuni* (*C. jejuni*) in a subject, wherein said immunogenic synthetic construct comprises one or more MeOPN-6-Gal monosaccharides and one or more MeOPN-2-Gal monosaccharides.

2. The immunogenic synthetic construct of claim 1 wherein the immunogenic synthetic construct is conjugated to a carrier protein.

3. The immunogenic synthetic construct of claim 2 wherein the carrier protein contains at least one T-cell epitope.

4. The immunogenic synthetic construct of claim 2 wherein the carrier protein is an ETEC protein or $CRM_{197}$.

5. The immunogenic synthetic construct of claim 1 further comprising one or more additional saccharides.

6. The immunogenic synthetic construct of claim 5 wherein the one or more additional saccharides is selected from the group consisting of monosaccharides containing one or more MeOPN moieties, galactose, fructose, glucose, heptose, N-acetyl galactosamine, N-acetyl glucosamine, glucitol, glucose, and modified forms of derivatives thereof.

7. The immunogenic synthetic construct of claim 6 wherein said monosaccharide containing one or more MeOPN moieties is MeOPN-1-Fru.

8. The immunogenic synthetic construct of claim 5 wherein said one or more additional saccharides is selected from the group consisting of CPS repeating blocks, heptose units, and MeOPN linkages of *C. jejuni* serotype complexes HS1, HS3, HS4, and HS23/36.

9. The immunogenic synthetic construct of claim 8 wherein said MeOPN linkages of *C. jejuni* serotype complexes HS1, HS3, HS4, and HS23/36 are selected from the group consisting of

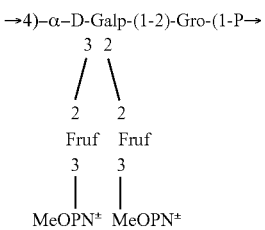

of HS 1;

$$\rightarrow 3)\text{-}\alpha\text{-D-6d-ido-Hepp-(1-4)-D-GlcpNAc-(1}\rightarrow \begin{matrix} \text{MeOPN}^{\pm} \\ | \\ 7 \\ \phantom{x} \\ 2 \\ | \\ \text{MeOPN}^{\pm} \end{matrix}$$

of HS4;

$$\rightarrow 3)\text{-}\beta\text{-D-6d-ido-Hepp-(1-4)-}\alpha\text{-D-Galp-(1}\rightarrow 3)\text{-}\beta\text{-D-ido-Hepp-(1-4)-}\alpha\text{-D-Galp-(1}\rightarrow \text{ of HS3; and}$$

with MeOPN$^{\pm}$ branches at position 2

$$\rightarrow 3)\text{-}\alpha\text{-D-Galp-(1-2)-3-O-Me-D-6d-altro-Hepp-(1-3)-D-GlcpNAc-(1}\rightarrow 3)\text{-}\alpha\text{-D-Galp-(1}\rightarrow$$

with MeOPN$^{\pm}$ at position 6 and 2 of HS23/36.

10. A composition comprising the immunogenic synthetic construct of claim 1.

11. The composition of claim 10 wherein said composition is a pharmaceutical composition.

12. The composition of claim 11 wherein said pharmaceutical composition is a vaccine.

13. The composition of claim 12 wherein said vaccine is a monovalent vaccine or a polyvalent vaccine.

14. The composition of claim 13 wherein said polyvalent vaccine comprises a formulation against one or more strains of *C. jejuni*.

15. The composition of claim 14 wherein said polyvalent vaccine further comprises a formulation against enterotoxigenic *Escherichia coli* (ETEC) or *Shigella*.

16. The composition of claim 14 wherein said one or more strains of *C. jejuni* is selected from the group consisting of *C. jejuni* serotypes HS 23/36, HS 1, HS2, HS3, HS4, and HS5/31.

17. The composition of claim 12 wherein said vaccine further comprises an additional immunoregulatory agent.

18. The composition of claim 17 wherein the additional immunoregulatory agent is selected from the group consisting of antigens of one or more strains of *C. jejuni*, antigens of enterotoxigenic *Escherichia coli* (ETEC), *Shigella* lipopolysaccharide structures, and unconjugated carrier proteins.

19. The composition of claim 12 wherein said vaccine further comprises one or more adjuvants.

20. The composition of claim 19 wherein said adjuvant is selected from the group consisting of toll-like receptor ligands, aluminum phosphate, aluminum hydroxide, monophosphoryl lipid A, liposomes, saponins, QS-21, and derivatives and combinations thereof.

21. A method of inducing an immune response against *C. jejuni* in a subject comprising administering to the subject an effective amount of the immunogenic synthetic construct of claim 1.

22. The method of claim 21 wherein the subject is human.

23. A method of inducing an immune response against *C. jejuni* in a subject comprising administering to the subject an effective amount of the composition of claim 11.

24. The method of claim 23 wherein the subject is human.

25. A method of inducing an immune response against *C. jejuni* in a subject comprising administering to the subject an effective amount of the composition of claim 12.

26. The method of claim 25 wherein said subject is a human.

27. A method of inducing an immune response against *C. jejuni* in a subject comprising administering to the subject an effective amount of the composition of claim 20.

28. The method of claim 27 wherein said subject is a human.

29. A method of inducing an immune response against *C. jejuni* in a subject, said method comprising
 (a.) administering to the subject an effective amount of the immunogenic synthetic construct of claim 1; and
 (b.) optionally administering to the subject one or more boosting doses of the immunogenic synthetic construct administered in step (a).

30. The method of claim 29 wherein the effective amount administered in step (a) is from about 0.1 µg to about 10 mg of the immunogenic synthetic construct.

31. The method of claim 29 wherein said method further comprises administering an adjuvant with the construct in step (a) and/or step (b).

32. The method of claim 31 wherein the adjuvant is selected from the group consisting of toll-like receptor ligands, aluminum phosphate, aluminum hydroxide, monophosphoryl lipid A, liposomes, saponins, QS-21, and derivatives and combinations thereof.

33. A method of inducing an immune response against *C. jejuni* in a subject, said method comprising
 (a). administering to the subject an effective amount of the composition of claim 12; and
 (b). optionally administering to the subject one or more boosting doses of the composition administered in step (a).

34. The method of claim 33 wherein the effective amount administered in step (a) is from about 0.1 µg to about 10 mg of immunogenic synthetic construct.

35. The method of claim 34 wherein said method further comprises administering an adjuvant with the construct in step (a) and/or step (b).

36. The method of claim 35 wherein the adjuvant is selected from the group consisting of toll-like receptor ligands, aluminum phosphate, aluminum hydroxide, monophosphoryl lipid A, liposomes, saponins, QS-21, and derivatives and combinations thereof.

* * * * *